(12) United States Patent
Merriman et al.

(10) Patent No.: US 10,902,939 B2
(45) Date of Patent: *Jan. 26, 2021

(54) METHODS AND SYSTEMS FOR DNA DATA STORAGE

(71) Applicant: Roswell Biotechnologies, Inc., San Diego, CA (US)

(72) Inventors: Barry L. Merriman, San Diego, CA (US); Tim Geiser, San Diego, CA (US); Paul Mola, San Diego, CA (US)

(73) Assignee: Roswell Biotechnologies, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/477,106

(22) PCT Filed: Jan. 10, 2018

(86) PCT No.: PCT/US2018/013140
§ 371 (c)(1),
(2) Date: Jul. 10, 2019

(87) PCT Pub. No.: WO2018/132457
PCT Pub. Date: Jul. 19, 2018

(65) Prior Publication Data
US 2019/0355442 A1    Nov. 21, 2019

Related U.S. Application Data

(60) Provisional application No. 62/444,656, filed on Jan. 10, 2017, provisional application No. 62/547,692, filed on Aug. 18, 2017.

(51) Int. Cl.
*G16B 50/40* (2019.01)
*C12Q 1/6869* (2018.01)
*G01N 27/327* (2006.01)

(52) U.S. Cl.
CPC .......... *G16B 50/40* (2019.02); *C12Q 1/6869* (2013.01); *G01N 27/3271* (2013.01); *G01N 27/3275* (2013.01)

(58) Field of Classification Search
None
See application file for complete search history.

(56) References Cited

U.S. PATENT DOCUMENTS

| | | | |
|---|---|---|---|
| 5,082,627 A | 1/1992 | Stanbro | |
| 5,194,133 A | 3/1993 | Clark et al. | |
| 5,366,140 A | 11/1994 | Koskenmaki et al. | |
| 5,414,588 A | 5/1995 | Barbee, Jr. | |
| 5,486,449 A | 1/1996 | Honso et al. | |
| 5,532,128 A | 7/1996 | Eggers et al. | |
| 5,583,359 A | 12/1996 | Ng et al. | |
| 5,639,507 A | 6/1997 | Galvagni et al. | |
| 5,767,687 A | 6/1998 | Geist | |
| 5,871,918 A | 2/1999 | Thorp et al. | |
| 5,881,184 A | 3/1999 | Guidash | |
| 5,982,018 A | 11/1999 | Wark | |
| 6,051,380 A | 4/2000 | Sosnowski et al. | |
| 6,060,023 A | 5/2000 | Maracas | |
| 6,094,335 A | 7/2000 | Early | |
| 6,110,354 A | 8/2000 | Saban | |
| 6,123,819 A | 9/2000 | Peeters | |
| 6,144,023 A | 11/2000 | Clerc | |
| 6,238,927 B1 | 5/2001 | Abrams et al. | |
| 6,440,662 B1 | 8/2002 | Gerwen et al. | |
| 6,464,889 B1 | 10/2002 | Lee et al. | |
| 6,506,564 B1 | 1/2003 | Mirkin et al. | |
| 6,537,747 B1 | 3/2003 | Mills, Jr. et al. | |
| 6,670,131 B2 | 12/2003 | Hashimoto | |
| 6,673,533 B1 | 1/2004 | Wohlstadter et al. | |
| 6,716,620 B2 | 4/2004 | Bashir et al. | |
| 6,749,731 B2 | 6/2004 | Kobori | |
| 6,762,050 B2 | 7/2004 | Fukushima et al. | |
| 6,764,745 B1 | 7/2004 | Karasawa et al. | |

(Continued)

FOREIGN PATENT DOCUMENTS

| | | |
|---|---|---|
| CN | 101231287 | 7/2008 |
| CN | 102706940 | 10/2012 |

(Continued)

OTHER PUBLICATIONS

Church et al. Next-Generation Digital Information storage in DNA Science vol. 337, p. 1628 and supplementary materials (Year: 2012).*

Ali et al. DNA hybridization detection using less than 10-nm gap silicon nanogap structure Sensors and Actuators A vol. 199, pp. 304-309 (Year: 2013).*

USPTO; Requirement for Restriction dated Nov. 2, 2011 in U.S. Appl. No. 12/667,583.

USPTO; Non-Final Office Action dated Sep. 28, 2018 in U.S. Appl. No. 12/667,583.

USPTO; Final Office Action dated Feb. 19, 2019 in U.S. Appl. No. 12/667,583.

(Continued)

*Primary Examiner* — John S Brusca
(74) *Attorney, Agent, or Firm* — Snell & Wilmer L.L.P.

(57) ABSTRACT

In various embodiments, an information storage system comprises: a writing device for synthesizing a nucleotide sequence that encodes a set of information; and a reading device for interpreting the nucleotide sequence by decoding the interpreted nucleotide sequence into the set of information, wherein the reading device comprises a molecular electronics sensor, the sensor comprising a pair of spaced apart electrodes and a molecular complex attached to each electrode to form a molecular electronics circuit, wherein the molecular complex comprises a bridge molecule and a probe molecule, and wherein the molecular electronics sensor produces distinguishable signals in a measurable electrical parameter of the molecular electronics sensor, when interpreting the nucleotide sequence.

18 Claims, 45 Drawing Sheets

Specification includes a Sequence Listing.

(56) References Cited

U.S. PATENT DOCUMENTS

| | | |
|---|---|---|
| 6,790,341 B1 | 9/2004 | Saban |
| 6,824,974 B2 | 11/2004 | Pisharody et al. |
| 6,861,224 B2 | 3/2005 | Fujita et al. |
| 6,916,614 B1 | 7/2005 | Takenaka et al. |
| 6,958,216 B2 | 10/2005 | Kelley |
| 7,015,046 B2 | 3/2006 | Wohlstadter et al. |
| 7,075,428 B1 | 7/2006 | Oleynik |
| 7,169,272 B2 | 1/2007 | Fritsch et al. |
| 7,183,055 B2 | 2/2007 | Van Der Weide |
| 7,189,435 B2 | 3/2007 | Tuominen et al. |
| 7,202,480 B2 | 4/2007 | Yokoi et al. |
| 7,208,077 B1 | 4/2007 | Albers et al. |
| 7,276,206 B2 | 10/2007 | Augustine et al. |
| 7,399,585 B2 | 7/2008 | Gau |
| 7,432,120 B2 | 10/2008 | Mascolo et al. |
| 7,470,533 B2 | 12/2008 | Xu et al. |
| 7,507,320 B2 | 3/2009 | Hwang et al. |
| 7,531,120 B2 | 5/2009 | Van Rijn et al. |
| 7,579,823 B1 | 8/2009 | Ayliffe |
| 7,691,433 B2 | 4/2010 | Kronholz et al. |
| 7,785,785 B2 | 8/2010 | Pourmand et al. |
| 7,834,344 B2 | 11/2010 | Mascolo et al. |
| 7,851,045 B2 | 12/2010 | Gandon et al. |
| 7,886,601 B2 | 2/2011 | Merassi et al. |
| 7,901,629 B2 | 3/2011 | Calatzis et al. |
| 7,943,394 B2 | 5/2011 | Flandre et al. |
| 8,241,508 B2 | 8/2012 | D'Urso |
| 8,313,633 B2 | 11/2012 | Li et al. |
| 8,351,181 B1 | 1/2013 | Ahn |
| 8,591,816 B2 | 11/2013 | Calatzis et al. |
| 8,652,768 B1 | 2/2014 | Huber et al. |
| 8,753,893 B2 | 6/2014 | Liu et al. |
| 8,927,464 B2 | 1/2015 | Aizenberg et al. |
| 8,940,663 B2 | 1/2015 | Iqbal et al. |
| 9,108,880 B2 | 8/2015 | Jin et al. |
| 9,306,164 B1 | 4/2016 | Chang et al. |
| 9,829,456 B1 | 11/2017 | Merriman et al. |
| 9,956,743 B2 | 5/2018 | Jin et al. |
| 10,036,064 B2 | 7/2018 | Merriman et al. |
| 10,125,420 B2 | 11/2018 | Jin et al. |
| 10,151,722 B2 | 12/2018 | Jin et al. |
| 10,508,296 B2 | 12/2019 | Merriman et al. |
| 10,526,696 B2 | 1/2020 | Jin et al. |
| 10,584,410 B2 | 3/2020 | Jin et al. |
| 10,597,767 B2 | 3/2020 | Merriman et al. |
| 10,712,334 B2 | 7/2020 | Choi et al. |
| 2002/0022223 A1 | 2/2002 | Connolly |
| 2002/0090649 A1 | 7/2002 | Chan et al. |
| 2002/0137083 A1 | 9/2002 | Kobori et al. |
| 2002/0138049 A1 | 9/2002 | Allen et al. |
| 2002/0142150 A1 | 10/2002 | Baumann et al. |
| 2002/0142477 A1 | 10/2002 | Lewis et al. |
| 2002/0172963 A1 | 11/2002 | Kelley et al. |
| 2002/0184939 A1 | 12/2002 | Yadav |
| 2003/0025133 A1 | 2/2003 | Brousseau |
| 2003/0040000 A1 | 2/2003 | Connolly et al. |
| 2003/0064390 A1 | 4/2003 | Schülein et al. |
| 2003/0087296 A1 | 5/2003 | Fujita et al. |
| 2003/0186263 A1 | 10/2003 | Frey et al. |
| 2003/0224387 A1 | 12/2003 | Kunwar et al. |
| 2004/0014106 A1 | 1/2004 | Patno et al. |
| 2004/0023253 A1 | 2/2004 | Kunwar et al. |
| 2004/0038090 A1 | 2/2004 | Faris |
| 2004/0063100 A1 | 4/2004 | Wang |
| 2004/0086929 A1 | 5/2004 | Weide et al. |
| 2004/0096866 A1 | 5/2004 | Hoffman et al. |
| 2004/0012161 A1 | 6/2004 | Chiu |
| 2004/0146863 A1 | 7/2004 | Pisharody et al. |
| 2004/0209355 A1 | 10/2004 | Edman et al. |
| 2004/0209435 A1 | 10/2004 | Patridge et al. |
| 2004/0235016 A1 | 11/2004 | Hamers |
| 2004/0248282 A1 | 12/2004 | Sobha |
| 2005/0029227 A1 | 2/2005 | Chapman |
| 2005/0067086 A1 | 3/2005 | Ito et al. |
| 2005/0074911 A1 | 4/2005 | Kornilovich et al. |
| 2005/0151541 A1 | 7/2005 | Brinz et al. |
| 2005/0172199 A1 | 8/2005 | Miller et al. |
| 2005/0181195 A1 | 8/2005 | Dubrow |
| 2005/0221473 A1 | 10/2005 | Dubin et al. |
| 2005/0227373 A1 | 10/2005 | Flandre et al. |
| 2005/0247573 A1 | 11/2005 | Nakamura et al. |
| 2005/0285275 A1 | 12/2005 | Son |
| 2005/0287548 A1 | 12/2005 | Bao et al. |
| 2005/0287589 A1 | 12/2005 | Connolly |
| 2006/0003482 A1 | 1/2006 | Chinthakindi et al. |
| 2006/0019273 A1 | 1/2006 | Connolly et al. |
| 2006/0024504 A1 | 2/2006 | Nelson et al. |
| 2006/0024508 A1 | 2/2006 | D'Urso et al. |
| 2006/0029808 A1 | 2/2006 | Zhai et al. |
| 2006/0051919 A1 | 3/2006 | Mascolo et al. |
| 2006/0051946 A1 | 3/2006 | Mascolo et al. |
| 2006/0105449 A1 | 5/2006 | Larmer et al. |
| 2006/0105467 A1 | 5/2006 | Niksa et al. |
| 2006/0128239 A1 | 5/2006 | Nun et al. |
| 2006/0147983 A1 | 7/2006 | O'uchi |
| 2006/0154489 A1 | 7/2006 | Tornow |
| 2006/0275853 A1 | 12/2006 | Matthew et al. |
| 2007/0026193 A1 | 2/2007 | Luzinov et al. |
| 2007/0048748 A1 | 3/2007 | Williams et al. |
| 2007/0140902 A1 | 6/2007 | Calatzis et al. |
| 2007/0148815 A1 | 6/2007 | Chao et al. |
| 2007/0184247 A1 | 9/2007 | Simpson et al. |
| 2007/0207487 A1 | 9/2007 | Emig et al. |
| 2007/0231542 A1 | 10/2007 | Deng |
| 2008/0098815 A1 | 5/2008 | Merassi et al. |
| 2008/0199657 A1 | 8/2008 | Capron et al. |
| 2008/0199659 A1 | 8/2008 | Zhao |
| 2009/0011222 A1 | 1/2009 | Xiu et al. |
| 2009/0017571 A1 | 1/2009 | Nuckolls |
| 2009/0020428 A1 | 1/2009 | Levitan |
| 2009/0027036 A1 | 1/2009 | Nuckolls et al. |
| 2009/0062684 A1 | 3/2009 | Gregersen et al. |
| 2009/0152109 A1 | 6/2009 | Whitehead et al. |
| 2009/0162927 A1 | 6/2009 | Naaman et al. |
| 2009/0170716 A1 | 7/2009 | Su et al. |
| 2009/0178935 A1 | 7/2009 | Reymond et al. |
| 2009/0295372 A1 | 12/2009 | Krstic et al. |
| 2009/0297913 A1 | 12/2009 | Zhang et al. |
| 2009/0306578 A1 | 12/2009 | Sivan et al. |
| 2009/0324308 A1 | 12/2009 | Law et al. |
| 2010/0038342 A1 | 2/2010 | Lim et al. |
| 2010/0044212 A1 | 2/2010 | Kim et al. |
| 2010/0055397 A1 | 3/2010 | Kurihara et al. |
| 2010/0132771 A1 | 6/2010 | Lu |
| 2010/0142259 A1 | 6/2010 | Drndic et al. |
| 2010/0149530 A1 | 6/2010 | Tomaru |
| 2010/0167938 A1 | 7/2010 | Su et al. |
| 2010/0184062 A1 | 7/2010 | Steinmueller-Nethl et al. |
| 2010/0188109 A1 | 7/2010 | Edel et al. |
| 2010/0194409 A1 | 8/2010 | Gao et al. |
| 2010/0206367 A1 | 8/2010 | Jeong et al. |
| 2010/0280397 A1 | 11/2010 | Feldman et al. |
| 2010/0285275 A1 | 11/2010 | Baca et al. |
| 2010/0285601 A1 | 11/2010 | Kong et al. |
| 2010/0288543 A1 | 11/2010 | Hung et al. |
| 2010/0300899 A1 | 12/2010 | Levine et al. |
| 2011/0056845 A1 | 3/2011 | Stellacci |
| 2011/0076783 A1 | 3/2011 | Liu et al. |
| 2011/0091787 A1 | 4/2011 | McGrath et al. |
| 2011/0160077 A1 | 6/2011 | Chaisson et al. |
| 2011/0166034 A1 | 7/2011 | Kwong et al. |
| 2011/0217763 A1 | 9/2011 | Rasooly et al. |
| 2011/0227558 A1 | 9/2011 | Mannion et al. |
| 2011/0229667 A1 | 9/2011 | Jin et al. |
| 2011/0233075 A1 | 9/2011 | Soleymani et al. |
| 2011/0287956 A1 | 11/2011 | Iqbal et al. |
| 2011/0291673 A1 | 12/2011 | Shibata et al. |
| 2011/0311853 A1 | 12/2011 | Fratti |
| 2011/0312529 A1 | 12/2011 | He et al. |
| 2012/0060905 A1 | 3/2012 | Fogel et al. |
| 2012/0220046 A1 | 8/2012 | Chao |
| 2012/0258870 A1 | 10/2012 | Schwartz et al. |
| 2012/0286332 A1 | 11/2012 | Rothberg et al. |
| 2013/0049158 A1 | 2/2013 | Hong et al. |

(56) References Cited

U.S. PATENT DOCUMENTS

| | | |
|---|---|---|
| 2013/0108956 A1 | 5/2013 | Lu et al. |
| 2013/0109577 A1 | 5/2013 | Korlach et al. |
| 2013/0162276 A1 | 6/2013 | Lee et al. |
| 2013/0183492 A1 | 7/2013 | Lee et al. |
| 2013/0214875 A1 | 8/2013 | Duncan et al. |
| 2013/0239349 A1 | 9/2013 | Knights et al. |
| 2013/0245416 A1 | 9/2013 | Yarmush et al. |
| 2013/0273340 A1 | 10/2013 | Neretina et al. |
| 2013/0281325 A1 | 10/2013 | Elibol et al. |
| 2013/0331299 A1 | 12/2013 | Reda et al. |
| 2014/0001055 A1 | 1/2014 | Elibol et al. |
| 2014/0011013 A1 | 1/2014 | Jin |
| 2014/0018262 A1 | 1/2014 | Reda et al. |
| 2014/0048776 A1 | 2/2014 | Huang et al. |
| 2014/0057283 A1 | 2/2014 | Wang et al. |
| 2014/0061049 A1 | 3/2014 | Lo et al. |
| 2014/0079592 A1 | 3/2014 | Chang et al. |
| 2014/0027775 A1 | 6/2014 | Quick et al. |
| 2014/0170567 A1 | 6/2014 | Sakamoto et al. |
| 2014/0174927 A1 | 6/2014 | Bashir et al. |
| 2014/0197459 A1 | 7/2014 | Kis et al. |
| 2014/0218637 A1 | 8/2014 | Gao et al. |
| 2014/0235493 A1 | 8/2014 | Zang et al. |
| 2014/0253827 A1 | 9/2014 | Gao et al. |
| 2014/0284667 A1 | 9/2014 | Basker et al. |
| 2014/0367749 A1 | 12/2014 | Bai et al. |
| 2014/0377900 A1 | 12/2014 | Yann et al. |
| 2015/0005188 A1 | 1/2015 | Levner et al. |
| 2015/0017655 A1 | 1/2015 | Huang et al. |
| 2015/0049332 A1 | 2/2015 | Sun et al. |
| 2015/0057182 A1 | 2/2015 | Merriman et al. |
| 2015/0068892 A1 | 3/2015 | Ueno et al. |
| 2015/0148264 A1 | 5/2015 | Esfandyarpour et al. |
| 2015/0177150 A1 | 6/2015 | Rothberg et al. |
| 2015/0191709 A1 | 7/2015 | Heron et al. |
| 2015/0263203 A1 | 9/2015 | Lewis et al. |
| 2015/0293025 A1 | 10/2015 | Ninomiya et al. |
| 2015/0294875 A1 | 10/2015 | Khondaker et al. |
| 2015/0344945 A1 | 12/2015 | Mandell et al. |
| 2016/0017416 A1 | 1/2016 | Boyanov et al. |
| 2016/0045378 A1 | 2/2016 | Geloen |
| 2016/0155971 A1 | 6/2016 | Strachan et al. |
| 2016/0187282 A1 | 6/2016 | Gardner et al. |
| 2016/0265047 A1 | 9/2016 | van Rooyen et al. |
| 2016/0284811 A1 | 9/2016 | Yu et al. |
| 2016/0319342 A1 | 11/2016 | Kawai et al. |
| 2016/0377564 A1 | 12/2016 | Carmignani et al. |
| 2017/0023512 A1 | 1/2017 | Cummins et al. |
| 2017/0037462 A1 | 2/2017 | Turner et al. |
| 2017/0043355 A1 | 2/2017 | Fischer |
| 2017/0044605 A1 | 2/2017 | Merriman |
| 2017/0131237 A1 | 5/2017 | Ikeda |
| 2017/0184542 A1 | 6/2017 | Chatelier et al. |
| 2017/0234825 A1 | 8/2017 | Elibol et al. |
| 2017/0240962 A1 | 8/2017 | Merriman |
| 2017/0332918 A1 | 11/2017 | Keane |
| 2018/0014786 A1 | 1/2018 | Keane |
| 2018/0031508 A1 | 2/2018 | Jin |
| 2018/0031509 A1 | 2/2018 | Jin |
| 2018/0045665 A1 | 2/2018 | Jin |
| 2018/0259474 A1 | 9/2018 | Jin |
| 2018/0297321 A1 | 10/2018 | Jin et al. |
| 2018/0305727 A1 | 10/2018 | Merriman |
| 2018/0340220 A1 | 11/2018 | Merriman |
| 2019/0004003 A1 | 1/2019 | Merriman |
| 2019/0033244 A1 | 1/2019 | Jin |
| 2019/0039065 A1 | 2/2019 | Choi |
| 2019/0041355 A1 | 2/2019 | Merriman |
| 2019/0041378 A1 | 2/2019 | Choi |
| 2019/0094175 A1 | 3/2019 | Merriman |
| 2019/0194801 A1 | 6/2019 | Jin et al. |
| 2019/0355442 A1 | 11/2019 | Merriman et al. |
| 2019/0376925 A1 | 12/2019 | Choi et al. |
| 2019/0383770 A1 | 12/2019 | Choi et al. |
| 2020/0157595 A1 | 5/2020 | Merriman et al. |
| 2020/0217813 A1 | 7/2020 | Merriman et al. |

FOREIGN PATENT DOCUMENTS

| | | |
|---|---|---|
| CN | 104685066 | 6/2015 |
| CN | 104703700 | 6/2015 |
| CN | 108027335 | 5/2018 |
| DE | 102012008375 | 10/2012 |
| DE | 102013012145 | 1/2015 |
| EP | 2053383 | 4/2009 |
| EP | 3403079 | 11/2018 |
| EP | 3408219 | 12/2018 |
| EP | 3408220 | 12/2018 |
| EP | 3414784 | 12/2018 |
| EP | 3420580 | 1/2019 |
| GB | 2485559 | 5/2012 |
| JP | 0233981 | 7/1990 |
| JP | 2018-522236 | 8/2018 |
| KR | 20070059880 | 6/2007 |
| KR | 20110104245 | 9/2011 |
| WO | 2002049980 | 6/2002 |
| WO | 2002074985 | 9/2002 |
| WO | 2003042396 | 5/2003 |
| WO | 2004096986 | 11/2004 |
| WO | 2004099307 | 11/2004 |
| WO | 2005108612 | 11/2005 |
| WO | 2007054649 | 5/2007 |
| WO | 2007102960 | 9/2007 |
| WO | 2007126432 | 11/2007 |
| WO | 2007128965 | 11/2007 |
| WO | 2009003208 | 1/2009 |
| WO | 2009035647 | 3/2009 |
| WO | 2010022107 | 2/2010 |
| WO | 2012083249 | 6/2012 |
| WO | 2012087352 | 6/2012 |
| WO | 2012152056 | 11/2012 |
| WO | 2013096851 | 6/2013 |
| WO | 2014182630 | 7/2014 |
| WO | 2015167019 | 11/2015 |
| WO | 2015176990 | 11/2015 |
| WO | 2015188197 | 12/2015 |
| WO | 2016016635 | 2/2016 |
| WO | 2016100635 | 6/2016 |
| WO | 2016100637 | 6/2016 |
| WO | 2016196755 | 12/2016 |
| WO | 2016210386 | 12/2016 |
| WO | 2017041056 | 3/2017 |
| WO | 2017042038 | 3/2017 |
| WO | 2017061129 | 4/2017 |
| WO | 2017123416 | 7/2017 |
| WO | 2017132567 | 8/2017 |
| WO | 2017132586 | 8/2017 |
| WO | 2017139493 | 8/2017 |
| WO | 2017147187 | 8/2017 |
| WO | 2017151680 | 9/2017 |
| WO | 2017184677 | 10/2017 |
| WO | 2018022799 | 2/2018 |
| WO | 2018026855 | 2/2018 |
| WO | 2018098286 | 5/2018 |
| WO | 2018132457 | 7/2018 |
| WO | 2018136148 | 7/2018 |
| WO | 2018200687 | 11/2018 |
| WO | 2018208505 | 11/2018 |

OTHER PUBLICATIONS

USPTO; Non-Final Office Action dated Aug. 19, 2019 in U.S. Appl. No. 12/667,583.

USPTO; Requirement for Restriction dated Dec. 1, 2016 in U.S. Appl. No. 13/996,477.

USPTO; Non-Final Office Action dated May 5, 2017 in U.S. Appl. No. 13/996,477.

USPTO; Final Office Action dated Oct. 4, 2017 in U.S. Appl. No. 13/996,477.

USPTO; Notice of Allowance dated Jan. 3, 2018 in U.S. Appl. No. 13/996,477.

(56) References Cited

OTHER PUBLICATIONS

USPTO; Final Office Action date Dec. 30, 2016 in U.S. Appl. No. 15/050,270.
USPTO; Advisory Action dated Mar. 14, 2017 in U.S. Appl. No. 15/050,270.
USPTO; Non-Final Office Action dated Sep. 29, 2017 in U.S. Appl. No. 15/050,270.
USPTO; Final Office Action dated Jul. 10, 2018 in U.S. Appl. No. 15/050,270.
USPTO; Advisory Action dated Sep. 26, 2018 in U.S. Appl. No. 15/050,270.
USPTO; Non-Final Office Action dated Feb. 26, 2019 in U.S. Appl. No. 15/050,270.
USPTO; Final Office Action dated Jul. 10, 2019 in U.S. Appl. No. 15/050,270.
USPTO; Notice of Allowance dated Jan. 6, 2020 in U.S. Appl. No. 15/050,270.
USPTO; Non-Final Office Action dated Oct. 19, 2016 in U.S. Appl. No. 15/220,307.
USPTO; Notice of Allowance dated Jul. 28, 2017 in U.S. Appl. No. 15/220,307.
USPTO; Requirement for Restriction dated Jan. 17, 2017 in U.S. Appl. No. 15/336,557.
USPTO; Non-Final Office Action dated May 16, 2017 in U.S. Appl. No. 15/336,557.
USPTO; Final Office Action dated Mar. 8, 2018 in U.S. Appl. No. 15/336,557.
USPTO; Notice of Allowance dated May 25, 2018 in U.S. Appl. No. 15/336,557.
USPTO; Non-Final Office Action dated Feb. 9, 2018 in U.S. Appl. No. 15/728,400.
USPTO; Final Office Action dated Jul. 10, 2018 in U.S. Appl. No. 15/728,400.
USPTO; Advisory Action dated Oct. 12, 2018 in U.S. Appl. No. 15/728,400.
USPTO; Advisory Action dated Nov. 14, 2018 in U.S. Appl. No. 15/728,400.
USPTO; Notice of Allowance dated Dec. 6, 2018 in U.S. Appl. No. 15/728,400.
USPTO; Non-Final Office Action dated Feb. 23, 2018 in U.S. Appl. No. 15/728,412.
USPTO; Notice of Allowance dated Sep. 12, 2018 in U.S. Appl. No. 15/728,412.
USPTO; Final Office Action dated Jun. 13, 2018 in U.S. Appl. No. 15/728,412.
USPTO; Non-Final Office Action dated Feb. 23, 2018 in U.S. Appl. No. 15/796,080.
USPTO; Final Office Action dated Jun. 14, 2018 in U.S. Appl. No. 15/796,080.
USPTO; Advisory Action dated Sep. 4, 2018 in U.S. Appl. No. 15/796,080.
USPTO; Notice of Allowance dated Oct. 11, 2018 in U.S. Appl. No. 15/796,080.
USPTO; Non-Final Office Action dated Mar. 7, 2019 in U.S. Appl. No. 15/944,356.
USPTO; Non-Final Office Action dated Sep. 4, 2018 in U.S. Appl. No. 15/979,135.
USPTO; Non-Final Office Action dated Nov. 30, 2018 in U.S. Appl. No. 15/979,135.
USPTO; Final Office Action dated Mar. 1, 2019 in U.S. Appl. No. 15/979,135.
USPTO; Advisory Action dated May 22, 2019 in U.S. Appl. No. 15/979,135.
USPTO; Non-Final Office Action dated Jun. 25, 2019 in U.S. Appl. No. 15/979,135.
USPTO; Notice of Allowance dated Dec. 11, 2019 in U.S. Appl. No. 15/979,135.
USPTO; Non-Final Office Action dated Aug. 22, 2019 in the U.S. Appl. No. 16/011,065.
USPTO; Final Office Action dated Mar. 6, 2020 in U.S. Appl. No. 16/011,065.
USPTO; Requirement for Restriction dated Oct. 15, 2018 in U.S. Appl. No. 16/015,028.
USPTO; Non-Final Office Action dated Dec. 26, 2018 in U.S. Appl. No. 16/015,028.
USPTO; Final Office Action dated Apr. 15, 2019 in U.S. Appl. No. 16/015,028.
USPTO; Non-Final Office Action dated Jul. 30, 2019 in the U.S. Appl. No. 16/015,028.
USPTO; Notice of Allowance dated Nov. 8, 2019 in U.S. Appl. No. 16/015,028.
USPTO; Requirement for Restriction dated Dec. 17, 2018 in U.S. Appl. No. 16/015,049.
USPTO; Non-Final Office Action dated Mar. 6, 2019 in U.S. Appl. No. 16/015,049.
USPTO; Final Office Action dated Jun. 19, 2019 in U.S. Appl. No. 16/015,049.
USPTO; Non-Final Office Action dated Nov. 5, 2019 in U.S. Appl. No. 16/015,049.
USPTO; Notice of Allowance dated Feb. 20, 2020 in U.S. Appl. No. 16/015,049.
USPTO; Non-Final Office Action dated Apr. 13, 2020 in U.S. Appl. No. 16/070,133.
USPTO; Restriction Requirement dated Sep. 19, 2019 in U.S. Appl. No. 16/073,706.
USPTO; Non-Final Office Action dated Oct. 24, 2019 in U.S. Appl. No. 16/073,706.
USPTO; Non-Final Office Action dated Jan. 10, 2020 in U.S. Appl. No. 16/076,673.
USPTO; Non-Final Office Action dated Feb. 1, 2019 in U.S. Appl. No. 16/152,190.
USPTO; Notice of Allowance dated May 30, 2019, in U.S. Appl. No. 16/152,190.
USPTO; Restriction Requirement dated May 29, 2019 in U.S. Appl. No. 16/250,929.
USPTO; Notice of Allowance dated Oct. 23, 2019 in U.S. Appl. No. 16/250,929.
USPTO; Restriction Requirement dated Apr. 8, 2020 in U.S. Appl. No. 16/479,257.
PCT; International Search Report and Written Opinion dated Nov. 29, 2012 in Application No. PCT/US2011/001995.
PCT; International Search Report and Written Opinion dated Apr. 13, 2018 in Application No. PCT/US2018/013140.
PCT; International Search Report and Written Opinion dated Jan. 27, 2017 in Application No. PCT/US2017/015437.
PCT; International Search Report and Written Opinion dated Jan. 27, 2017 in Application No. PCT/US2017/015465.
PCT; International Search Report and Written Opinion dated Jul. 26, 2017 in Application No. PCT/US2017/017231.
PCT; International Search Report and Written Opinion dated May 25, 2017 in Application No. PCT/US2017/018950.
PCT; International Search Report and Written Opinion dated Jul. 20, 2018 in Application No. PCT/US2018/029382.
PCT; International Search Report and Written Opinion dated Jul. 20, 2018 in Application No. PCT/US2018/029393.
PCT; International Search Report and Written Opinion dated Sep. 27, 2016 in Application No. PCT/US2016/039446.
PCT; International Search Report and Written Opinion dated Nov. 22, 2017 in Application No. PCT/US2017/044023.
PCT; International Search Report and Written Opinion dated Dec. 26, 2017 in Application No. PCT/US2017/044965.
PCT; International Search Report and Written Opinion dated Nov. 9, 2018 in Application No. PCT/US2018/048873.
PCT; International Search Report and Written Opinion dated Apr. 8, 2010 in Application No. PCT/US2009/054235.
PCT; International Search Report and Written Opinion dated Jan. 18, 2019 in Application No. PCT/US2018/055264.
PCT; International Search Report and Written Opinion dated Mar. 12, 2018 in Application No. PCT/US2017/063025.
PCT; International Search Report and Written Opinion dated Mar. 7, 2018 in Application No. PCT/US2017/063105.

(56) References Cited

OTHER PUBLICATIONS

PCT; International Search Report and Written Opinion dated Apr. 18. 2017 in Application No. PCT/US2016/068922.
CN; Notice of the First Office Action dated Sep. 2, 2019 in Chinese Application No. 201680049272.8.
CN; Notice of the First Office Action dated Sep. 30, 2019 in Chinese Application No. 201780020478.2.
EP; European Search Report dated Jan. 30, 2019 in Application No. 16815467.2.
EP; European Search Report dated Aug. 2, 2019 in Application No. 16885434.7.
EP; European Search Report dated Jan. 29, 2020 in Application No. 17745013.7.
EP; European Search Report dated Aug. 2, 2019 in Application No. 17745026.9.
EP; European Search Report dated Jan. 29, 2020 in Application No. 17750776.1.
EP; European Search Report dated Oct. 24, 2019 in Application No. 17757146.0.
EP; European Search Report dated Mar. 6, 2020 in Application No. 17835231.6.
EP; European Search Report dated Feb. 7, 2020 in Application No. 17837566.3.
Ahn et al., "Electrical Immunosensor Based on a Submicron-Gap Interdigitated Electrode and Gold Enhancement," Biosensors and Bioelectronics, vol. 26, pp. 4690-4696, (2011).
Alayo et al., "Gold Interdigitated Nanoelectrodes as a Sensitive Analytical Tool for Selective Detection of Electroactive Species via Redox Cycling," Microchim Acta, vol. 183, pp. 1633-1639, (2016).
Antibody Structure Downloaded from https://absoluteantibody.com/antibody-resources/antibody-overview/antibody-structure/ (Mar. 1, 2019).
Bai et al., "Review: Gas Sensors Based on Conducting Polymers," Sensors, vol. 7, pp. 267-307, (2007).
Bailey et al., "DNA-Encoded Antibody Libraries: A Unified Platform for Multiplexed Cell Sorting and Detection of Genes and Proteins," Journal of American Chemical Society, vol. 129, pp. 1959-1967, (2007).
Bechelany et al. "Synthesis Mechanisms of Organized Nanoparticles: Influence of Annealing Temperature and Atmosphere," Crystal Growth and Design, vol. 10, pp. 587-596 (Oct. 21, 2010).
Berdat et al., "Label-Free Detection of DNA with Interdigitated Micro-Electrodes in a Fluidic Cell," Lab on a Chip, vol. 8, pp. 302-308, (2008).
Bhura, "3D Interdigitated Electrode Array (IDEA) Biosensor for Detection of Serum Biomarker," Master Thesis, Portland State University, 68 Pages, (2011).
Blossey, R., "Self-Cleaning Surfaces-Virtual Realities," Nature Materials, vol. 2(5), pp. 301-306, (May 2006).
Bonilla et al., "Electrical Readout of Protein Microarrays on Regular Glass Slides," Analytical Chemistry, vol. 83, pp. 1726-1731, (2011).
Botsialas et al., "A Miniaturized Chemocapacitor System for the Detection of Volatile Organic Compounds," Sensors and Actuators B, Chemical, vol. 177, pp. 776-784, (2013).
Branagan et al "Enhanced Mass Transport of Electroactive Species to Annular Nanoband Electrodes Embedded in Nanocapillary Array Membranes," Journal of the American Chemical Society, vol. 134, pp. 8617-8624, (2012).
Braun et al., "DNA-Templated Assembly and Electrode Attachment of a Conducting Silver Wire," Letters to Nature, vol. 391(6669), pp. 775-778, (Feb. 1998).
Briglin et al., "Exploitation of Spatiotemporal Information and Geometric Optimization of Signal/Noise Performance Using Arrays of Carbon Black-Polymer Composite Vapor Detectors," Sensors and Actuators B, vol. 82, pp. 54-74, (2002).
Cassie, A.B.D. et al., "Wettability of Porous Surfaces," Transitions of the Faraday Society, vol. 40, pp. 546-551, (Jan. 1944) (Abstract Only).

Cerofolini et al., "A Hybrid Approach to Nanoelectronics: A Hybrid Approach to Nanoelectrics," Nanotechnology, Institute of Physics Publishing, GB, vol. 16, No. 8, pp. 1040-1047 (2005).
Chen, X. et al., "Electrical Nanogap Devices for Biosensing," Materials Today, vol. 13, pp. 28-41, (Nov. 2010).
Chen et al., "Electrochemical Approach for Fabricating Nanogap Electrodes with Well Controllable Separation," Applied Physics Letters, vol. 86, pp. 123105.1-123105.3, (2005).
Chen et al., "Fabrication of Submicron-Gap Electrodes by Silicon vol. Expansion for DNA-Detection," Sensors and Actuators A, vol. 175, pp. 73-77, (2012).
Choi, J. E. et al., "Fabrication of Microchannel with 60 Electrodes and Resistance Measurement," Flow Measurement and Instrumentation, vol. 21, pp. 178-183, (Sep. 2010) (Abstract Only).
Choi Y.S. et al., "Hybridization by an Electroatomical Genome on Detection on Using an Indicator-Free DNA on a Microelectrode-Array DNA Chip," Bulletin of the Korean Chemistry Society, vol. 26, pp. 379-383, (2005).
Choi, C. et al., "Strongly Superhydrophobic Silicon Nanowires by Supercritical CO2 Drying," Electronic Materials Letters, vol. 6 (2), pp. 59-64, (Jun. 2010).
Church et al., "Next-Generation Digital Information Storage in DNA," Science, vol. 337(6102), p. 6102, (Sep. 28, 2012).
Cosofret et al., "Microfabricated Sensor Arrays Sensitive to pH and K+ for Ionic Distribution Measurements in the Beating Heart," Analytical Chemistry, vol. 67, pp. 1647-1653, (1995).
Coulson S.R. et al., "Super-Repellent Composite Fluoropolymer Surfaces," The Journal of Physical Chemistry B., vol. 104(37), pp. 8836-8840, (Aug. 2000).
Dickey et al., "Electrically Addressable Parallel Nanowires with 30 NM Spacing from Micromolding and Nanoskiving," Nano Letters, vol. 8(12), pp. 4568-4573, (2008).
Fan et al., "Detection of MicroRNAs Using Target-Guided Formation of Conducting Polymer Nanowires in Nanogaps," Journal of the American Chemical Society, vol. 129, pp. 5437-5443, (2007).
Fink et al. "Electrical Conduction Through DNA Molecules," Nature, vol. 398, pp. 407-410 (Jan. 20, 1999).
Fuller et al., "Real-Time Single-Molecule Electronic DNA Sequencing by Synthesis Using Polymer-Tagged Nucleotides on a Nanopore Array," Proceedings of the National Academy of Sciences, vol. 113(19), pp. 5233-523, (May 10, 2016).
Gapin, A.I. et al., "CoPt Patterned Media in Anodized Aluminum Oxide Templates," Journal of Applied Physics, vol. 99(8), pp. 08G902 (1-3), (Apr. 2006).
Ghindilis, A. et al., "Real Time Biosensor Platforms Fully Integrated Device for Impedimetric Assays," ECS Transactions, vol. 33, pp. 59-68, (2010).
Guo et al., "Conductivity of a single DNA duplex bridging a carbon nanotube gap," Nat. Nanotechnol., vol. 3, No. 3, pp. 1-12 (2008).
Han, "Energy Band Gap Engineering of Graphene Nanoribbons," Physical Review Letters, vol. 98, pp. 1-7, (May 16, 2007).
Han et al., "Redox Cycling in Nanopore-Confined Recessed Dual-Ring Electrode Arrays," Journal of Physical Chemistry C, vol. 120, pp. 20634-20641, (2016).
Hanief, Topic, Pineda-Vargas, "Solid State Dewetting of Continuous Thin Platinum Coatings," Nuclear Instruments and Methods in Physics Research, vol. 363, pp. 173-176, (2015).
Hashioka et al., "Deoxyribonucleic Acid Sensing Device with 40-NM-Gap-Electrodes Fabricated by Low-Cost Conventional Techniques," Applied Physics Letters, vol. 85(4), p. 687-688, (Jul. 2004).
He et al., "Electromechanical Fabrication of Atomically Thin Metallic Wires and Electrodes Separated with Molecular-Scale Gaps," Journal of Electroanalytical Chemistry, vol. 522, pp. 167-172, (Jan. 2002).
Heerema et al., "Graphene Nanodevices for DNA Sequencing," Nature Nanotechnology, vol. 11, pp. 127-136, (Feb. 3, 2016).
Henry et al., "Microcavities Containing Individually Addressable Recessed Microdisk and Tubular Nanoband Electrodes," Journal of The Electrochemical Society, vol. 146(9), pp. 3367-3373, (1999).
Hwang et al., "Electrical Transport Through 60 Base Pairs of Poly (dG)-Poly (dC) DNA Molecules," Applied Physics Letters, vol. 81(6), p. 1134-1136, (Aug. 2002).

(56) References Cited

OTHER PUBLICATIONS

Ino et al., "Addressable Electrode Array Device with IDA Electrodes for High-Throughput Detection," Lab on a Chip, vol. 11, p. 385-388, (2011).
Ino et al., "Local Redox-Cycling-Based Electrochemical Chip Device with Seep Microwells for Evaluation of Embryoid Bodies," Angewandte Chemie International Edition, vol. 51, pp. 6648-6652, (2012).
Iqbal et al., "Direct Current Electrical Characterization of ds-DNA in Nanogap Junctions," Applied Physics Letter, vol. 86, p. 153901-1-153901-3, (Apr. 2005).
Javey et al., "Layer-By-Layer Assembly of Nanowires for Three-Dimensional, Multifunctional Electronics," Nano Letters, vol. 7, pp. 773-777, (2007).
Khawli et al., "Charge Variants in IgG1-Isolation, Characterization, In Vitro Binding Properties and Pharmacokinetics in Rats," Landes Bioscience, vol. 2(6), pp. 613-623, (2010).
Kim, J. Y. et al., "Optically Transparent Glass with Vertically Aligned Surface Al2O3 Nanowires Having Superhydrophobic Characteristics," NANO: Brief Reports and Reviews, vol. 5(2), pp. 89-95, (Apr. 2010) (Abstract Only).
Kim et al., "Rapid Fabrication of Uniformly Sized Nanopores and Nanopore Arrays for Parallel DNA Analysis," Advances Materials, vol. 18, pp. 3149-3153, (Dec. 4, 2006).
Kitsara et al., "Single Chip Interdigitated Electrode Capacitive Chemical Sensor Arrays," Sensors and Actuators B, vol. 127, pp. 186-192, (2007).
Kitsara et al., "Small-Volume Multiparametric Electrochemical Detection at Low Cost Polymeric Devices Featuring Nanoelectrodes," SPIE, vol. 9518, 9 Pages, (2015).
Kraft, "Doped Diamond: A Compact Review on a New, Versatile Electrode Material," International Journal of Electrochemistry, vol. 2, pp. 355-385, (May 2007).
Kumar et al., "Terminal Phosphate Labeled Nucleotides: Synthesis, Applications and Linker Effect on Incorporation by DNA Polymerases," Nucleosides, Nucleotides and Nucleic Acids, Taylor and Francis, vol. 24, No. 5-7, pp. 401-408 (2005).
Lee, K. H. et al., "One-Chip Electronic Detection of DNA Hybridization using Precision Impedance-Based CMOS Array Sensor," Biosensors and Bioelectronics, vol. 26, pp. 1373-1379, (Dec. 15, 2010).
Lin et al., "An Addressable Microelectrode Array for Electrichemical Detection," Analytical Chemistry, vol. 80, pp. 6830-6833, (2008).
Liu et al., "Atomically Thin Molybdenum Disulfide Nanopores with High Sensitivity for DNA Translocation," ACS Nano, vol. 8, pp. 2504-2511, (Feb. 18, 2014).
Liu et al., "An Enzyme-Based E-DNA Sensor for Sequence-Specific Detection of Femtomolar DNA Targets," J. Am. Chem. Soc., vol. 130(21), pp. 6820-6825, (2008).
Liu et al., "Controllable Nanogap Fabrication on Microchip by Chronopotentiometry," Electrochimica Acta, vol. 50, pp. 3041-3047, (2005).
MacNaughton et al., "High-Throughput Heterogeneous Integration of Diverse Nanomaterials on a Single Chip for Sensing Applications," PLOS One, vol. 9(10), e111377, 7 Pages, (2014).
Mastrototaro et al., "Thin-Film Flexible Multielectrode Arrays for Voltage Measurements in the Heart," IEEE Engineering in Medicine & Biology Society 11th Annual International Conference, 1 Page, (1989).
Mastrototaro et al., "Rigid and Flexible Thin-Film Multielectrode Arrays for Transmural Cardiac Recording," IEEE Transactions on Biomedical Engineering, vol. 39, pp. 217-279, (1992).
Mirando-Castro et al., "Hairpin-DNA Probe for Enzyme-Amplified Electrochemical Detection of Legionella pnuemophila," Anal. Chem., vol. 79, pp. 4050-4055, (Jun. 1, 2007).
Nishida, et al. "Self-Oriented Immobilization of DNA Polymerase Tagged by Titanium-Binding Peptide Motif," Langmuir, vol. 31, pp. 732-740 (Dec. 17, 2014).
Niwa, O. et al., "Fabrication and Characteristics of Vertically Separated Interdigitated Array Electrodes," Journal of Electroanalytical Chemistry and Interfacial Electrochemistry, vol. 267 pp. 291-297, (Aug. 10, 1989) (Abstract Only).
Okinaka et al., ""Polymer" Inclusions in Cobalt-Hardened Electroplated Gold," Journal the of Electrochemical Society, vol. 125, p. 1745, (1978). (Abstract Only).
Park, S.J. et al., "Array-Based Electrical Detection of DNA with Nanoparticle Probes," Science, vol. 295, pp. 1503-1506, (Feb. 22, 2002).
Park, C.W. et al., "Fabrication of Poly-Si/ AU Nano-Gaps Using Atomic-Layer-Deposited Al2O3 as a Sacrificial Layer," Nanotechnology, vol. 16, pp. 361-364, (Feb. 1, 2005) (Abstract Only).
Parkin, I. P. et al., "Self-Cleaning Coatings," Journal of Materials Chemistry, vol. 15(17), pp. 1689-1695, (Dec. 2004).
Prins et al., "Room-Temperature Gating of Molecular Junctions Using Few-Layer Graphene Nanogap Electrodes," Nano Letters, vol. 11, pp. 4607-4611, (Oct. 21, 2011).
Pugliese et al., "Processive Inforporation of Deoxynucleoside Triphosphate Analogs by Single-Molecule DNA Polymerase I (Klenow Fragment) Nanocircuits," Journal of the American Chemical Society, vol. 137, No. 30, pp. 9587-9594 (2015).
Qing et al., "Finely Tuning Metallic Nanogap Size with Electrodeposition by Utilizing High-Frequency Impedance in Feedback," Angewandte Chemie Int ed, vol. 44, pp. 7771-7775, (2005).
Reed et al., "Conductance of a Molecular Junction Reports," Science, vol. 278, pp. 252-254, (Oct. 1997).
Reichert et al., "Driving Current Through Single Organic Molecules," Physical Review Letters, vol. 88(17), pp. 176804-1-176804-4, (Apr. 2002).
Roppert et al., "A New Approach for an Interdigitated Electrodes DNA-Sensor," XVIIIth International Symposium on Bioelectrochemistry and Bioenergetics, Bioelectrochemistry, p. 143, (2005).
Roy, S. et al., "Mass-Produced Nanogap Sensor Arrays for Ultra-Sensitive Detection of DNA," Journal of the American Chemical Society, vol. 131, pp. 12211-12217, (Aug. 5, 2009) (Abstract Only).
Ruttkowski, E. et al., "CMOS based Arrays of Nanogaps Devices for Molecular Devices," Proceedings of 2005 5th IEEE Conference on Nanotechnology, vol. 1, pp. 438-441, (Jul. 2005) (Abstract Only).
Sanguino et al., "Interdigitated Capacitive Immunosensors with PVDF Immobilization Layers," IEEE Sensors Journal, vol. 14(4), pp. 1260-1265, (Apr. 2014).
Santschi et al., "Interdigitated 50nm Ti Electrode Arrays Fabricated using $XeF_2$ Enhanced Focused Ion Beam Etching," Nanotechnology, vol. 17, pp. 2722-2729, (2006).
Schaefer et al., "Stability and Dewetting Kinetics of Thin Gold Films on Ti, TiOx, and ZnO Adhesion Layers," Acta Materialia, vol. 61, pp. 7841-7848, (2013).
Schrott, W. et al., "Metal Electrodes in Plastic Microfluidic Systems," Microelectronic Engineering, vol. 86, pp. 1340-1342, (Jun. 2009).
Shimanovsky et al., "Hiding Data in DNA," International Workshop on Information Hiding, Lecture Notes in Computer Science, pp. 373-386, (Dec. 18, 2012).
Shimoda, T. et al., "Solution-Processed Silicon Films and Transistors," Nature, vol. 440(7085), pp. 783-786, (Apr. 2006).
Sholders et al., "Distinct Conformations of a Putative Translocation Element in Poliovirus Polymerase," Journal of Molecular Biology, vol. 426(7), pp. 1407-1419, (Apr. 3, 2014).
Singh et al., "3D Nanogap Interdigitated Electrode Array Biosensors," Analytical and Bioanalytical Chemistry, vol. 397, pp. 1493-1502, (2010).
Singh et al., "Evaluation of Nanomaterials-Biomolecule of Impedimetric Biosensors," 11th IEEE International Conference on Nanotechnology, pp. 707-710, (2011).
Singh et al., "Nanoparticle-Enhanced Sensitivity of a Nanogap-Interdigitated Electrode Array Impedimetric Biosensor," Langmuir, vol. 27, pp. 13931-13939, (2011).
Stagni, C. et al., "CMOS DNA Sensor Array with Integrated A/D Conversation Based on Label-Free Capacitance Measurement," IEEE Journal of Solid-State Circuits, vol. 41, pp. 2956-2964, (Nov. 20, 2006).

(56) References Cited

OTHER PUBLICATIONS

Stenning, "The Investigation of Grain Boundary Development and Crystal Synthesis of Thin Gold Films on Silicon Wafers," http://www.ucl.ac.uk/~ucapikr/projects, (Mar. 31, 2009).

Su, Y., "Modeling and Characteristic Study of Thin Film Based Biosensor Based on COMSOL," Mathematical Problems in Engineering, Article 581063 (6 Pages), (Apr. 7, 2014).

Thompson, "Solid-State Dewetting of Thin Films," Department of Materials Science and Engineering, vol. 42, pp. 399-434, (2012).

Urban, M. et al., "A Paralleled Readout System for an Electrical DNA-Hybridization Assay Based on a Microstructured Electrode Array," Review of Scientific Instruments, vol. 74, pp. 1077-1081, (Jan. 2003) (Abstract Only).

Van Gerwin et al., "Nanoscaled Interdigitated Electrode Arrays for Biochemical Sensors," Sensors and Actuators B, vol. 49, pp. 73-80, (1998).

Van Megan et al., "Submicron Electrode Gaps Fabricated by Gold Electrodeposition at Interdigitated Electrodes," Key Engineering Materials, vol. 605, pp. 107-110, (2014).

Wang et al., "Electronics and Optoelectronics of Two-Dimensional Transition Metal Dichalcogenides," Nature Nanotechnology, vol. 7, pp. 699-712, (Nov. 6, 2012).

Xu et al., "Fabrication of Complex Metallic Nanostructures by Nanoskiving," American Chemical Society Nano, vol. 1(3), pp. 215-227, (2007).

Zafarani et al., "Electrochemical Redox Cycling in a New Nanogap Sensor: Design and Simulation," Journal of Electroanalytical Chemistry, vol. 760, pp. 42-47, (2015).

USPTO; Notice of Allowance dated May 11, 2020 in U.S. Appl. 16/073,706.

USPTO; Notice of Allowance dated Jun. 1, 2020 in U.S. Appl. 16/076,673.

USPTO; Non-Final Office Action dated Jun. 2, 2020 in U.S. Appl. No. 16/684,338.

USPTO; Non-Final Office Action dated Jun. 15, 2020 in U.S. Appl. No. 16/878,484.

USPTO; Non-Final Office Action dated Jun. 30, 2020 in U.S. Appl. 16/479,257.

EP; European Search Report dated Jun. 18, 2020 in Application No. 16815467.2.

CN; Office Action dated Jun. 5, 2020 in Chinese Patent Application No. 2017800204782.

EP; European Search Report dated Jun. 26, 2020 in Application No. 17874229.2.

Li et al., "Graphene Channel Liquid Container Field Effect Transistor as pH Sensor," Hindawi Publishing Corp., Journal of Nanomaterials 2014.

\* cited by examiner

EXAMPLE BINARY DATA PAYLOAD  0010100110011100111101000101101

EXAMPLE BINARY ENCODING SCHEMES (BES)

| BES1 | BES2 | BES3 | BES4 | BES5 | BES6 |
|---|---|---|---|---|---|
| 00 → A | 0 → T | 0 → AA | 0 → X | 000 → A | 0 → GATT |
| 01 → C | 1 → G | 1 → CCC | 1 → Y | 001 → C | 1 → ACA |
| 10 → G | | | | 010 → G | |
| 11 → T | | | | 011 → T | |
| | | | | 100 → X | |
| | | | | 101 → Y | |
| | | | | 110 → W | |
| | | | | 111 → Z | |

BES1  0010100110011100111101000101101
      A G G C T A T T G G A G T C  (SEQ ID NO: 9)

BES2  0010100110011100111101000101101
      AACACAACCAACCCAACCCCCACAAACACCAC  (SEQ ID NO: 10)

BES3  0010100110011100111101000101101
      AAAAACCCAACCAACCCAAAACCCCCAAAAAACCCCCCAAAAAACCCCCCCCAAAAAACCCCCAACCAAAAAACCCCCAACCC  (SEQ ID NO: 11)

BES5  0010100110011100111101000101101
      C  G  T  C  W  T  Z  G  C  T  T  (SEQ ID NO: 12)

METHODS AND SYSTEMS FOR DNA DATA STORAGE

CROSS-REFERENCE TO RELATED APPLICATIONS

This application is a U.S. national phase filing under 35 U.S.C. § 371 of PCT/US2018/013140 filed on Jan. 10, 2018, which claims priority to and the benefit of U.S. Provisional Patent Application Ser. No. 62/444,656, filed Jan. 10, 2017 and entitled "Methods, Apparatus and Systems for DNA Data Storage," and U.S. Provisional Patent Application Ser. No. 62/547,692, filed Aug. 18, 2017 and entitled "Molecular Electronics Sensors for DNA Data Storage," the disclosures of which are incorporated herein by reference in their entireties.

INCORPORATION BY REFERENCE

The present application incorporates by reference a sequence listing, in electronic format, entitled 6895202300_SEQL.txt, created Oct. 26, 2020, which is approximately 4 kb in size. The information in the electronic format of the sequence listing is incorporated herein by reference in its entirety.

FIELD

The present disclosure generally relates to electronic data storage and retrieval, and more particularly to a DNA information storage and retrieval system comprising molecular sensors for reading DNA sequences and encoder/decoder algorithms for DNA sequence-binary conversions.

BACKGROUND

The advent of digital computing in the 20th Century created the need for archival storage of large amounts of digital or binary data. Archival storage is intended to house data for long periods of time, e.g., years, decades or longer, in a way that is very low cost, and that supports the rare need to re-access the data. Although an archival storage system may feature the ability to hold unlimited amounts of data at very low cost, such as through a physical storage medium able to remain dormant for long periods of time, the data writing and recovery in such a system can be the relatively slow or otherwise costly processes. The dominant forms of archival digital data storage that have been developed to date include magnetic tape, and, more recently, compact optical disc (CD). However, as data production grows, there is a need for even higher density, lower cost, and longer lasting archival digital data storage systems.

It has been observed that in biology, the genomic DNA of living organisms functions as a form of digital information archival storage. On the timescale of the existence of a species, which may extend for thousands to millions of years, the genomic DNA in effect stores the genetic biological information that defines the species. The complex enzymatic, biochemical processes embodied in the biology, reproduction and survival of the species provide the means of writing, reading and maintaining this information archive. This observation has motivated the idea that perhaps the fundamental information storage capacity of DNA could be harnessed as the basis for high density, long duration archival storage of more general forms of digital information.

What makes DNA attractive for information storage is the extremely high information density resulting from molecular scale storage of information. In theory for example, all human-produced digital information recorded to date, estimated to be approximately 1 ZB (ZettaByte) (~$10^{21}$ Bytes), could be recorded in less than $10^{22}$ DNA bases, or $\frac{1}{60}^{th}$ of a mole of DNA bases, which would have a mass of just 10 grams. In addition to high data density, DNA is also a very stable molecule, which can readily last for thousands of years without substantial damage, and which could potentially last far longer, for tens of thousands of years, or even millions of years, such as observed naturally with DNA frozen in permafrost or encased in amber.

SUMMARY

In various embodiments, an information storage system is disclosed. In various aspects, the system comprises a DNA reading device, a digital data encoding/decoding algorithm, and a DNA writing device, wherein the properties of these three elements are co-optimized to minimize or reduce various cost metrics and increase overall system performance. In various aspects, the co-optimization may comprise reducing the error rate of the system, through balancing, avoiding, or correcting the errors in DNA reading and writing. In other instances, the co-optimization may comprise reducing the DNA reading or writing time in the system, e.g., by avoiding the use of slower speed DNA sequence motifs, and/or by using error correction/avoidance to compensate for errors incurred from rapid operation of the system.

In various embodiments of the present disclosure, a DNA data reader is provided for use in a DNA data storage system. In particular, a molecular sensor is provided that can extract the digital information suitably encoded within a single DNA molecule. In certain aspects, such sensors may be in a high-density chip-based format that can provide the high-throughput, low-cost, fast data extraction capability required for large scale DNA data storage systems. In various examples, the sensor for reading the digital data stored in DNA molecules processes individual encoded DNA molecules directly, so that there is no need for complicated sample preparation such as making copies of DNA or clonal populations. In various aspects of the system, data is stored directly in synthetic DNA or DNA analogues that are synthetized with features beneficial for digital data storage that cannot be replicated by standard methods of copying DNA.

In various embodiments of a DNA data storage system, recovered data may be stored in a great variety of DNA analogs or modified DNA molecules in addition to native DNA, which provides greater choices of data writing systems and more effective data storage systems. In various aspects of the system, the time required to extract information encoded in a DNA molecule is short, e.g., on the order of seconds, which fundamentally enables short turnaround times for data recovery. In various aspects, the system can perform well over a large range of DNA molecular lengths, e.g., from lengths as short as 10's of bases, to 100's of bases, to 1000's of bases, and greater than tens of thousands of bases. This ability provides greater flexibility in the choice of DNA writing/synthesis technology, and eliminates the need to further prepare DNA samples prior to reading to meet length constraints in reading the digital information.

In various aspects of the present disclosure, a molecular sensor for DNA sequence reading can be deployed in a highly scalable, low cost, CMOS chip format, providing for efficient mass manufacturing, and low cost systems and instruments, and overall low costs in reading digital data stored in DNA. In various aspects, systems and devices required to read Exabyte-scale digital data from DNA data are highly compact and energy efficient in order to support practical, robust deployment locally at on-site data centers and to support highly scalable cloud-based archival data storage services.

In various aspects, reading of data stored in DNA in accordance to the present disclosure exceeds the performance, in speed, throughput and cost, in reading data archived in conventional archival storage formats such as magnetic tape or optical discs. An advantage of the present DNA data storage system is that it provides enabling technology for DNA digital data storage systems capable of practical Exabyte scale storage, and Zettabyte scale storage.

In various embodiments, the DNA writing device of a DNA Archival Storage System comprises a CMOS chip further comprising molecular electronics sensor devices. In other instances, the DNA writing device is a CMOS chip comprising voltage/current directed synthesis sites on pixel electrodes.

In various embodiments, aspects of the archive operations, such as copy, append, targeted deletion, targeted reading, and searching through molecular biology procedures, as applied to a DNA storage archive system are disclosed herein.

In various embodiments, an information storage system comprises: a writing device for synthesizing a nucleotide sequence that encodes a set of information; and a reading device for interpreting the nucleotide sequence by decoding the interpreted nucleotide sequence into the set of information, wherein the reading device comprises a molecular electronics sensor, the sensor comprising a pair of spaced apart electrodes and a molecular complex attached to each electrode to form a molecular electronics circuit, wherein the molecular complex comprises a bridge molecule and a probe molecule, and wherein the molecular electronics sensor produces distinguishable signals in a measurable electrical parameter of the molecular electronics sensor, when interpreting the nucleotide sequence.

In various aspects, the set of information comprises binary data. In certain aspects, the nucleotide sequence comprises a DNA sequence. For example, the system provides binary data storage in the form of DNA molecules, and provides for extraction of the archived data when retrieval is desired.

In various embodiments, the system further comprises at least one of error detecting schemes or error correction schemes within the DNA sequence. In certain aspects, the error detecting schemes are selected from repetition code, parity bits, checksums, cyclic redundancy checks, cryptographic hash functions and hamming codes, and the error correction schemes are selected from automatic repeat request, convolutional codes, block codes, hybrid automatic repeat request and Reed-Solomon codes.

In various embodiments, the writing device of the system comprises a CMOS chip based array of actuator pixels for DNA synthesis, the actuator pixels directing voltage/current or light-mediated deprotection within a DNA synthesis reaction comprising a phosphoramidite or ligation chemistries.

In various embodiments, the probe molecule comprises a polymerase enzyme, and wherein the measurable electrical parameter of the sensor is modulated by enzymatic activity of the polymerase enzyme. The polymerase enzyme may comprise a native polymerase enzyme or a genetically engineered polymerase enzyme selected from Klenow, Phi29, TAQ, BST, T7, or a reverse transcriptase.

In various embodiments, the reading device of the system further comprises a buffer solution, operating parameters for measuring the measurable electrical parameter, and two or more sequence segments of a DNA template molecule, that, when processed by the polymerase, produce the distinguishable signals in the measurable electrical parameter when performed in the conditions provided by the buffer solution and the operating parameters. In certain aspects, the buffer solution comprises modified dNTPs. In various aspects, the sequence segments of the DNA template molecule that produce the distinguishable signals comprise any one or combination of different DNA bases, modified DNA bases, DNA base analogues, multi-base sequences or motifs, or homopolymer runs of DNA bases.

In various embodiments, the measurable electrical parameter of the sensor comprises a source-drain current between the spaced apart electrodes and through the molecular complex. The molecular electronics sensor may be part of a CMOS sensor array chip further comprising a plurality of molecular electronics sensors and supporting pixel circuitry that performs measurement of the measurable electrical parameter.

In various embodiments, the molecular electronics sensor further comprises a gate electrode adjacent the spaced apart electrodes. In various aspects, the bridge molecule of a sensor in the system comprises a double stranded DNA oligomer, a protein alpha helix, a graphene nanoribbon, a carbon nanotube, an antibody, or a Fab arm of an antibody.

In various embodiments, a method of interpreting a set of information encoded in a nucleotide sequence is disclosed. The method comprises: supplying the nucleotide sequence to a molecular electronics sensor capable of producing distinguishable signals in a measurable electrical parameter of the molecular electronics sensor, relating to the set of information; generating the distinguishable signals; and converting the distinguishable signals into the set of information, wherein the molecular electronics sensor comprises a pair of spaced apart electrodes and a molecular complex attached to each electrode to form a molecular electronics circuit, wherein the molecular complex comprises a bridge molecule and a probe molecule. In various aspects, the set of information comprises binary data. In certain aspects, the nucleotide sequence comprises a DNA sequence.

In various embodiments, a method of encoding a set of information into a nucleotide sequence is disclosed. The method comprises: providing a set of information; converting the set of information into one or more predetermined nucleotides capable of generating distinguishable signals in a measurable electrical parameter of a molecular electronics sensor, using an encoding scheme; and assembling the one or more nucleotides into the nucleotide sequence. In various aspects, the one or more predetermined nucleotides capable of generating distinguishable signals comprise nucleotides that are resistant to secondary structure formation compared to a variant of the same nucleotides.

In various embodiments, converting the set of information into a nucleotide sequence comprises use of a binary encoding scheme (denoted herein as "BES"). In various examples, the BES comprises any one or more of BES1, BES2, BES3, BES4, BES5 and BES6.

In various embodiments, the molecular electronics sensor in the method comprises a pair of spaced apart electrodes and a molecular complex attached to each electrode to form a molecular electronics circuit, wherein the molecular complex comprises a bridge molecule and a probe molecule, and wherein the molecular electronics sensor produces the distinguishable signals in a measurable electrical parameter of the molecular electronics sensor when interpreting the nucleotide sequence. In various aspects, the set of information in the method comprises binary data.

BRIEF DESCRIPTION OF THE DRAWING FIGURES

Figure 17:
FIG. 17 illustrates an embodiment of a molecular electronic sensor where the Klenow Fragment of *E. Coli* Polymerase I is conjugated directly into the current path and directly to the metal electrodes, with no arm or bridge molecules.
Figure 18:
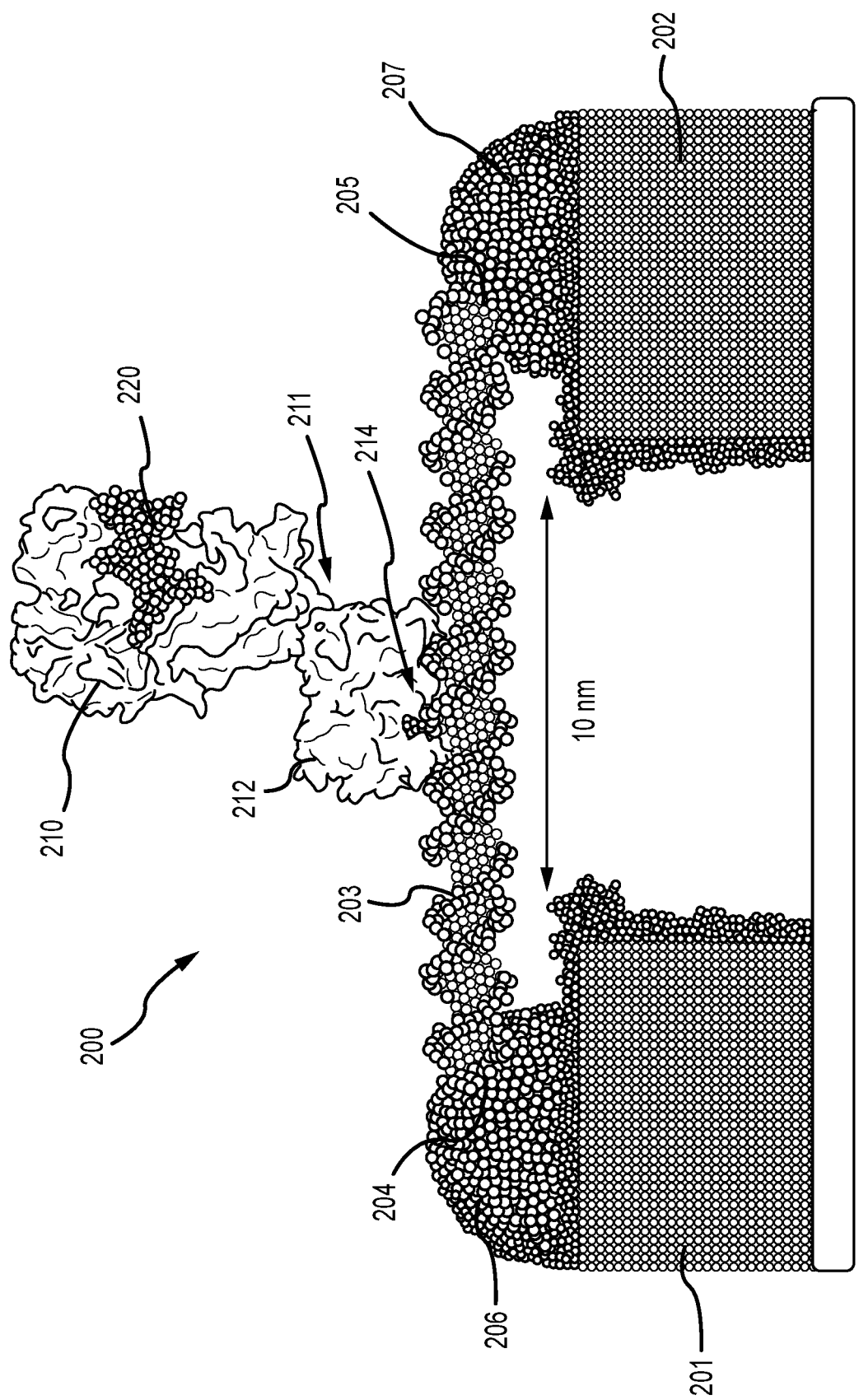
FIG. 18 illustrates an embodiment of a molecular sensor usable as a DNA reader device in various aspects of the present DNA data storage system.
Figure 20:
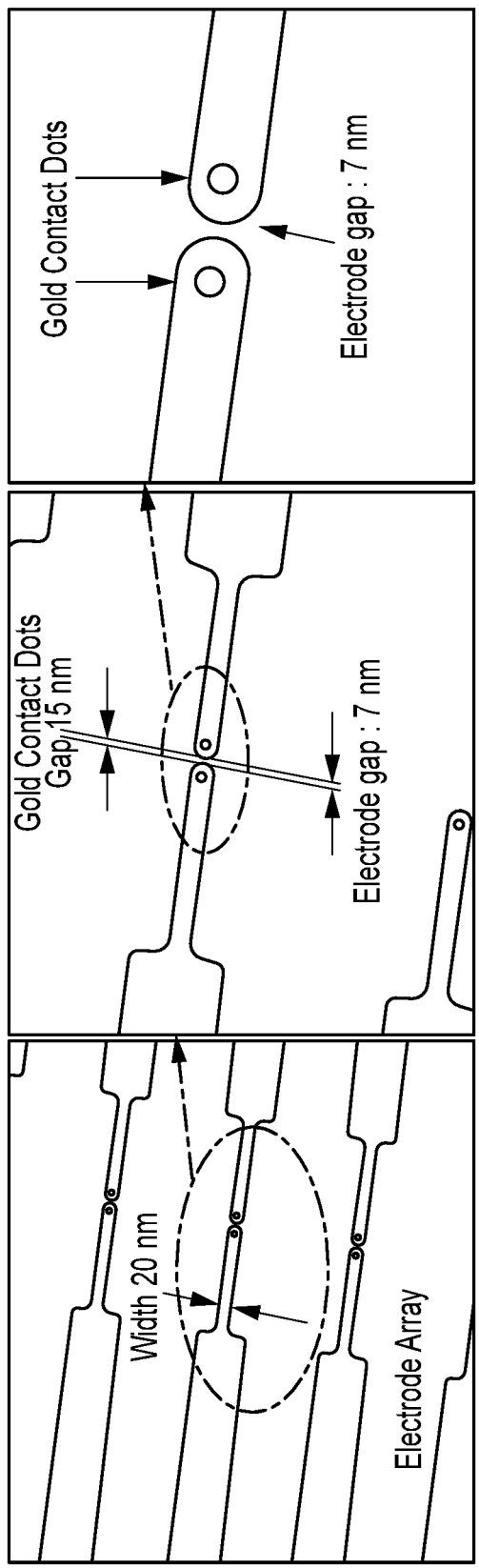
Figure 21:
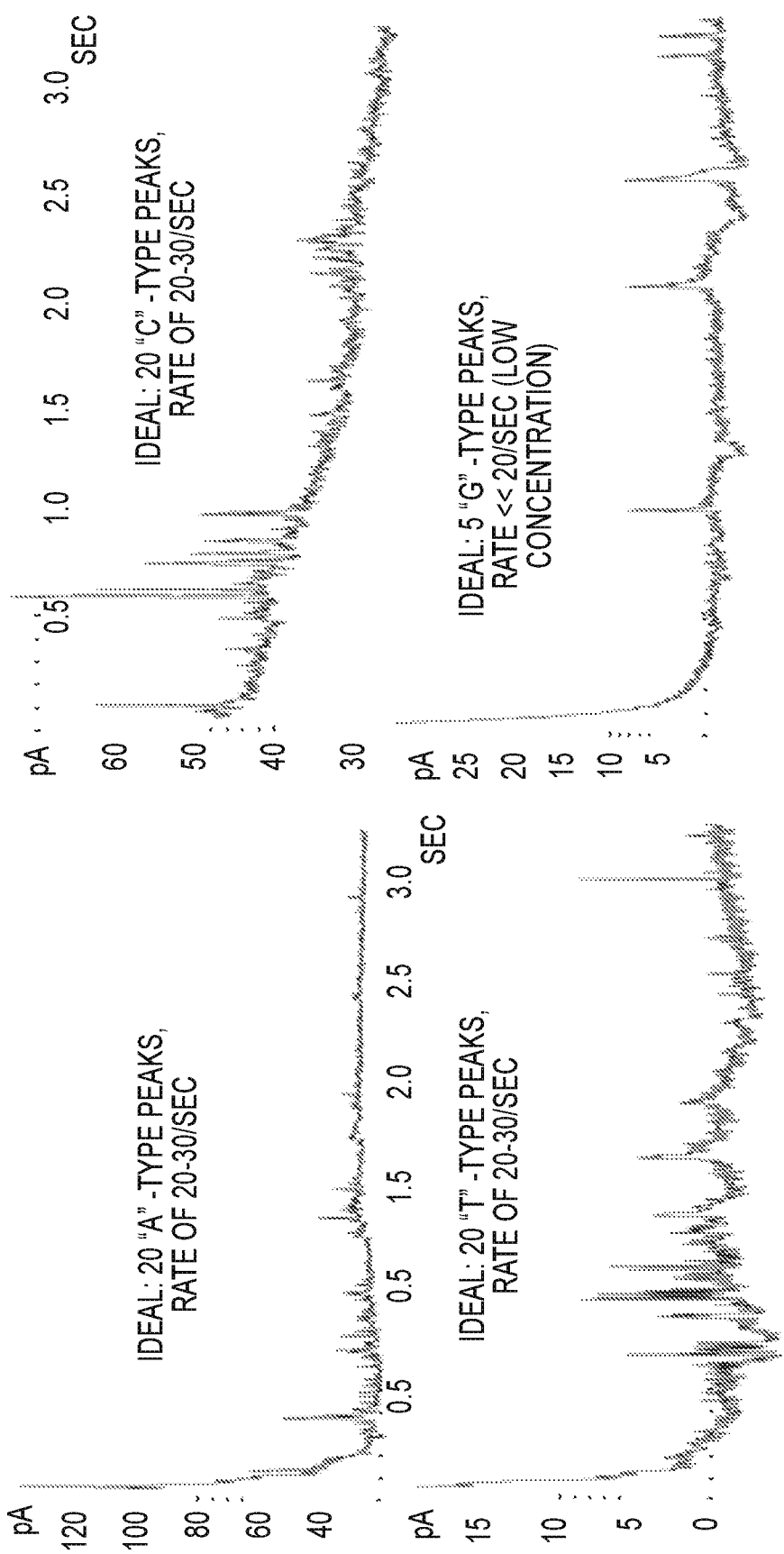
Figure 22:
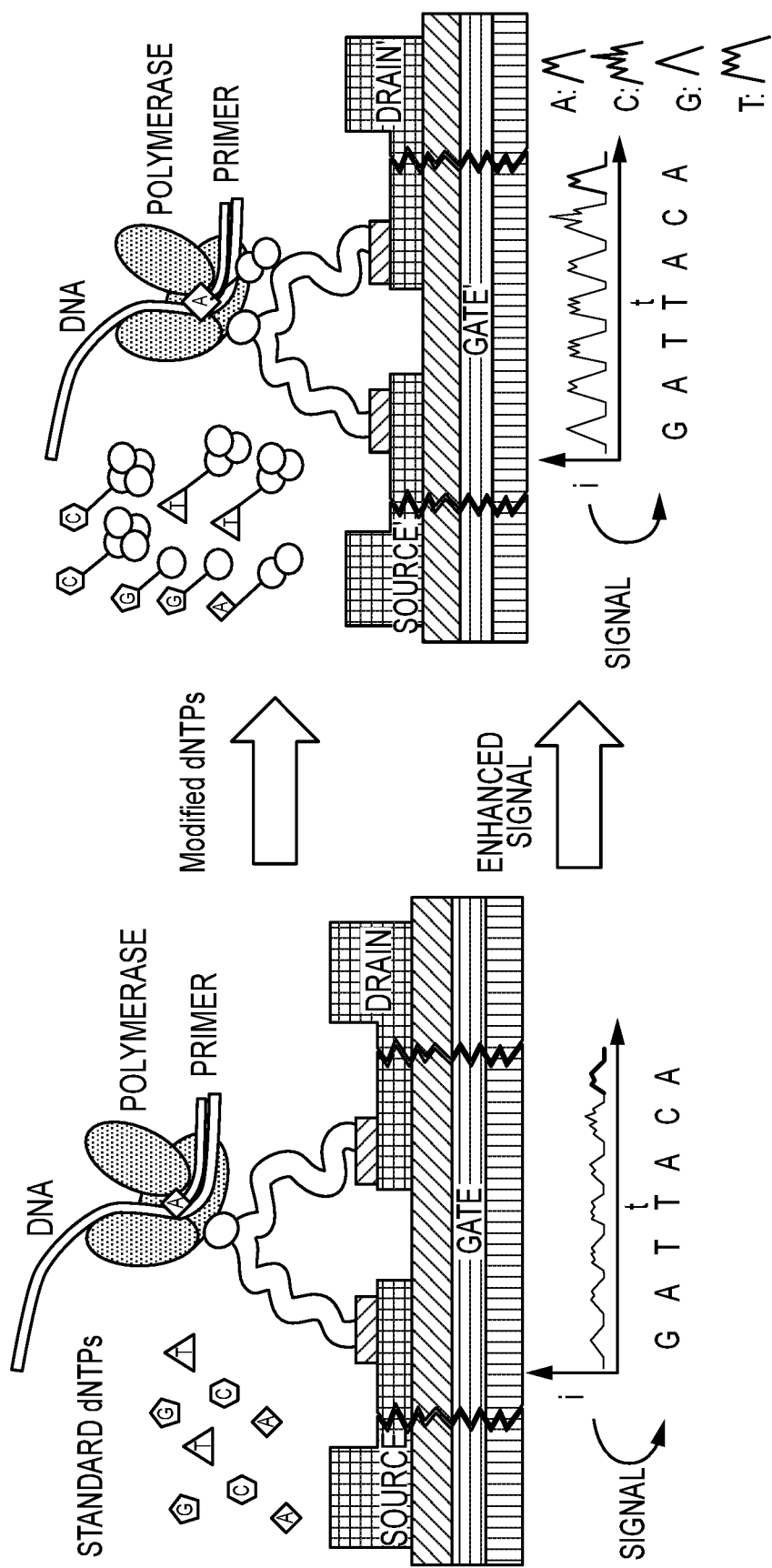
Figure 23:
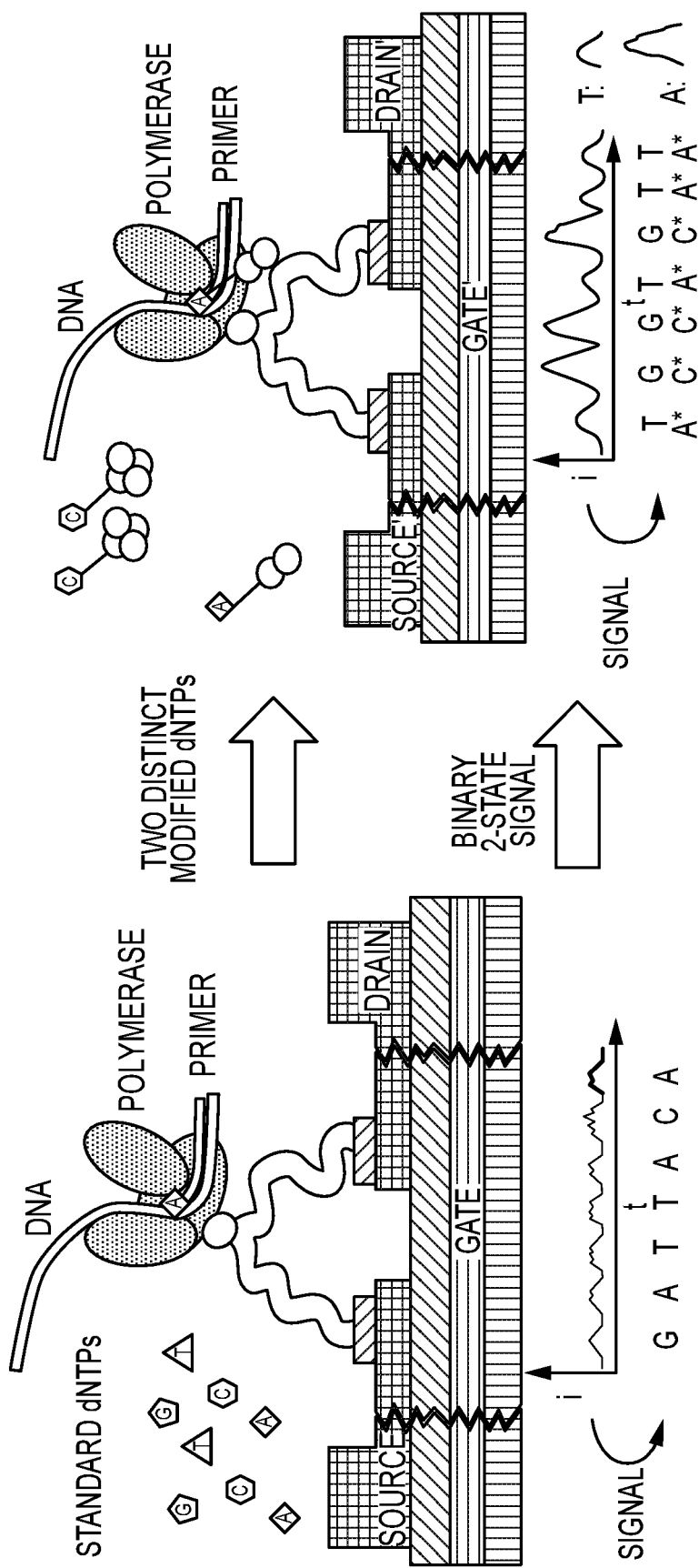
Figure 24:
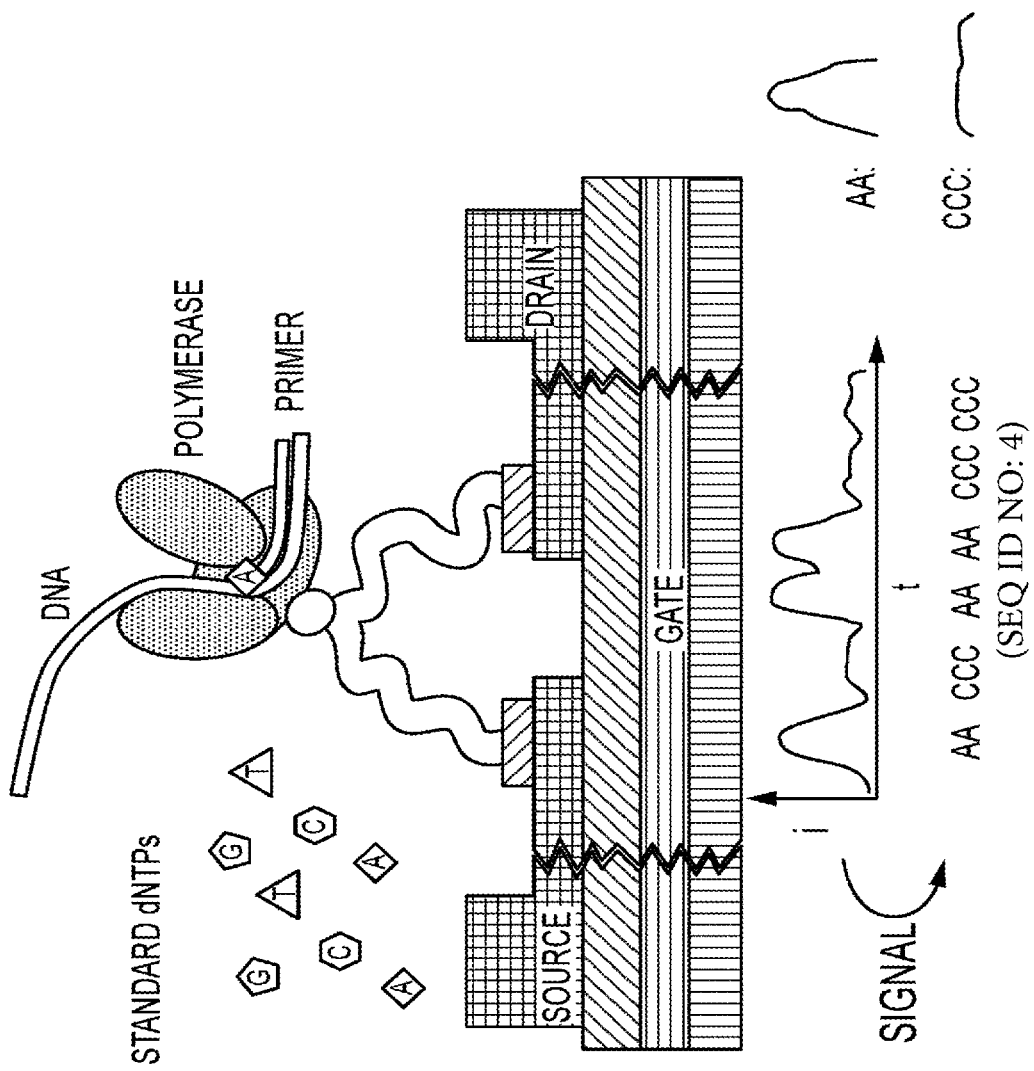
Figure 25:
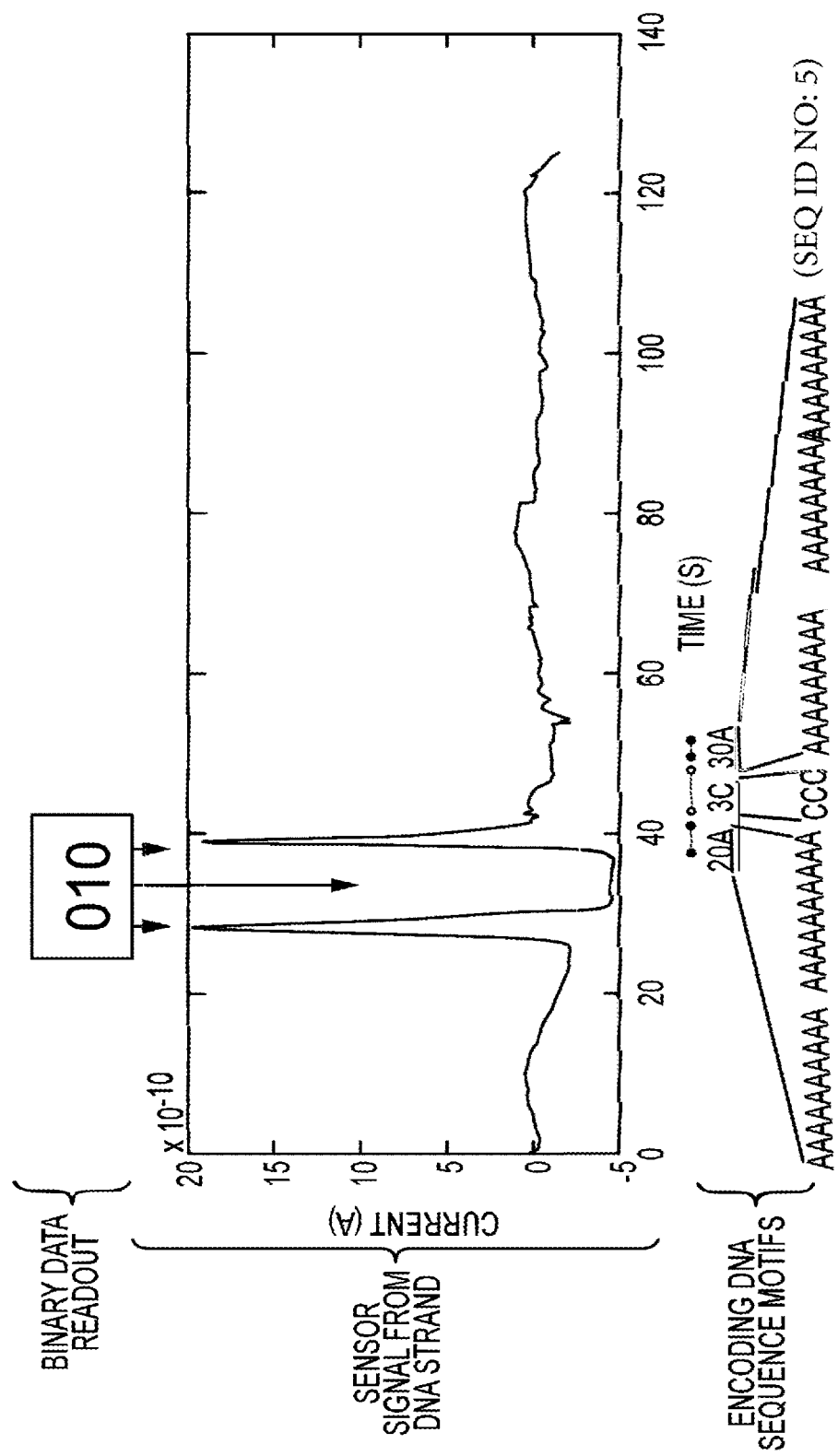
Figure 26A:
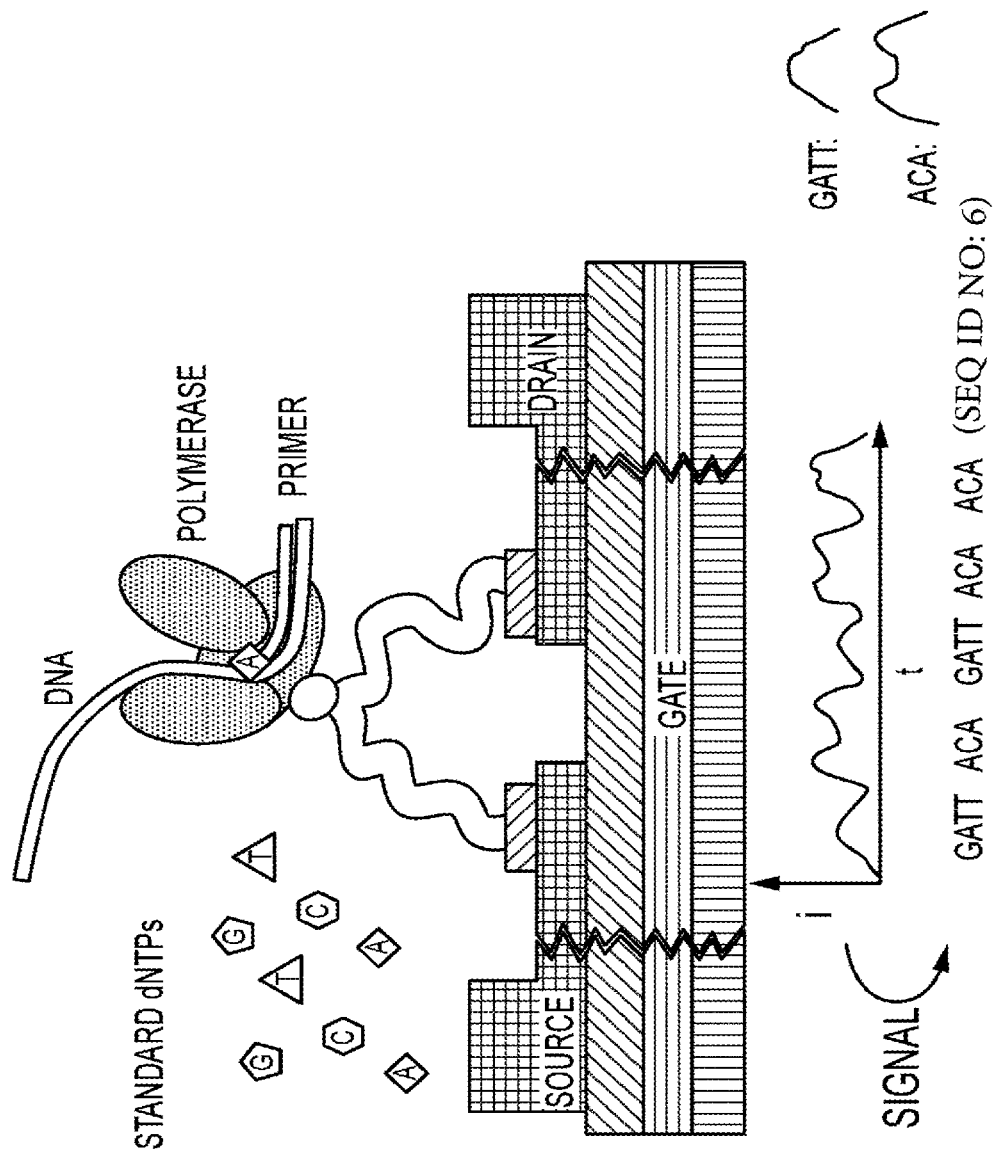
Figure 26B:
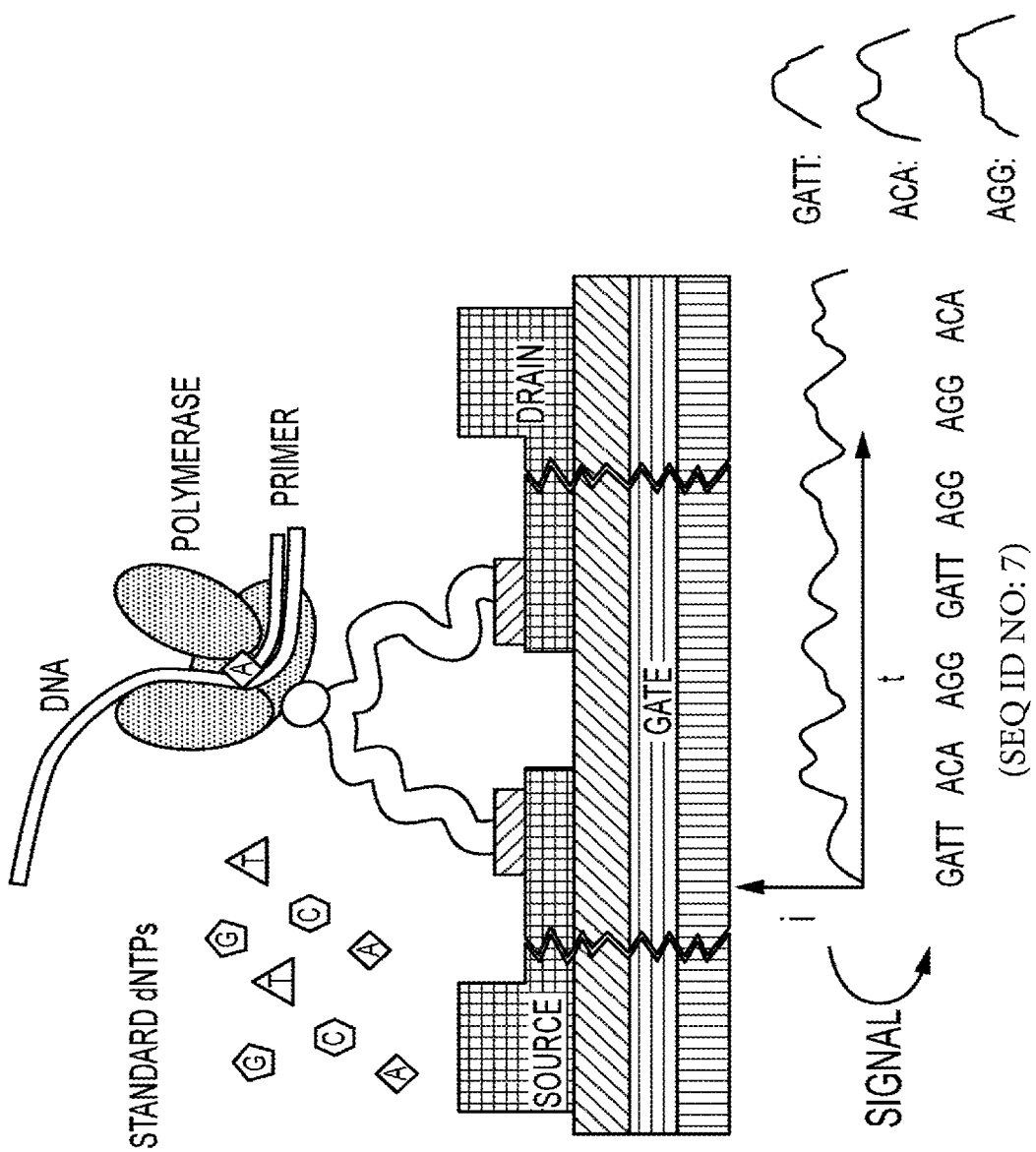
Figure 26C:
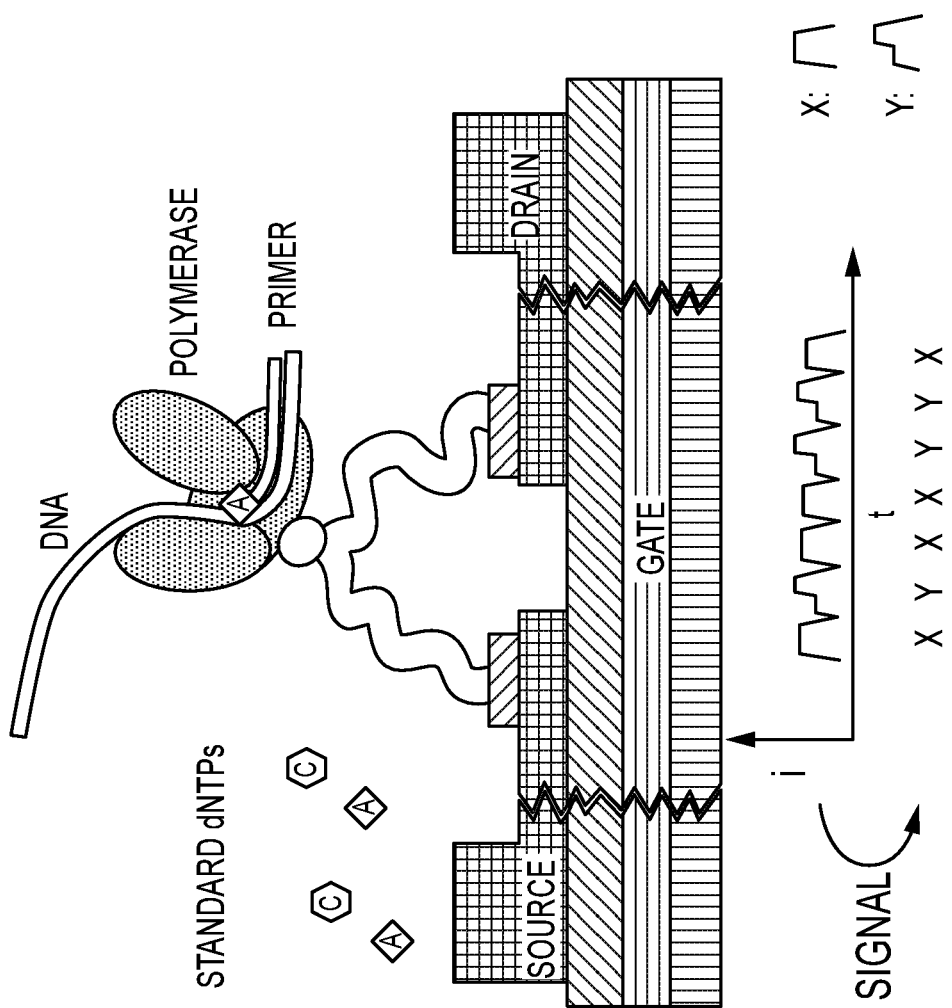
Figure 26D:
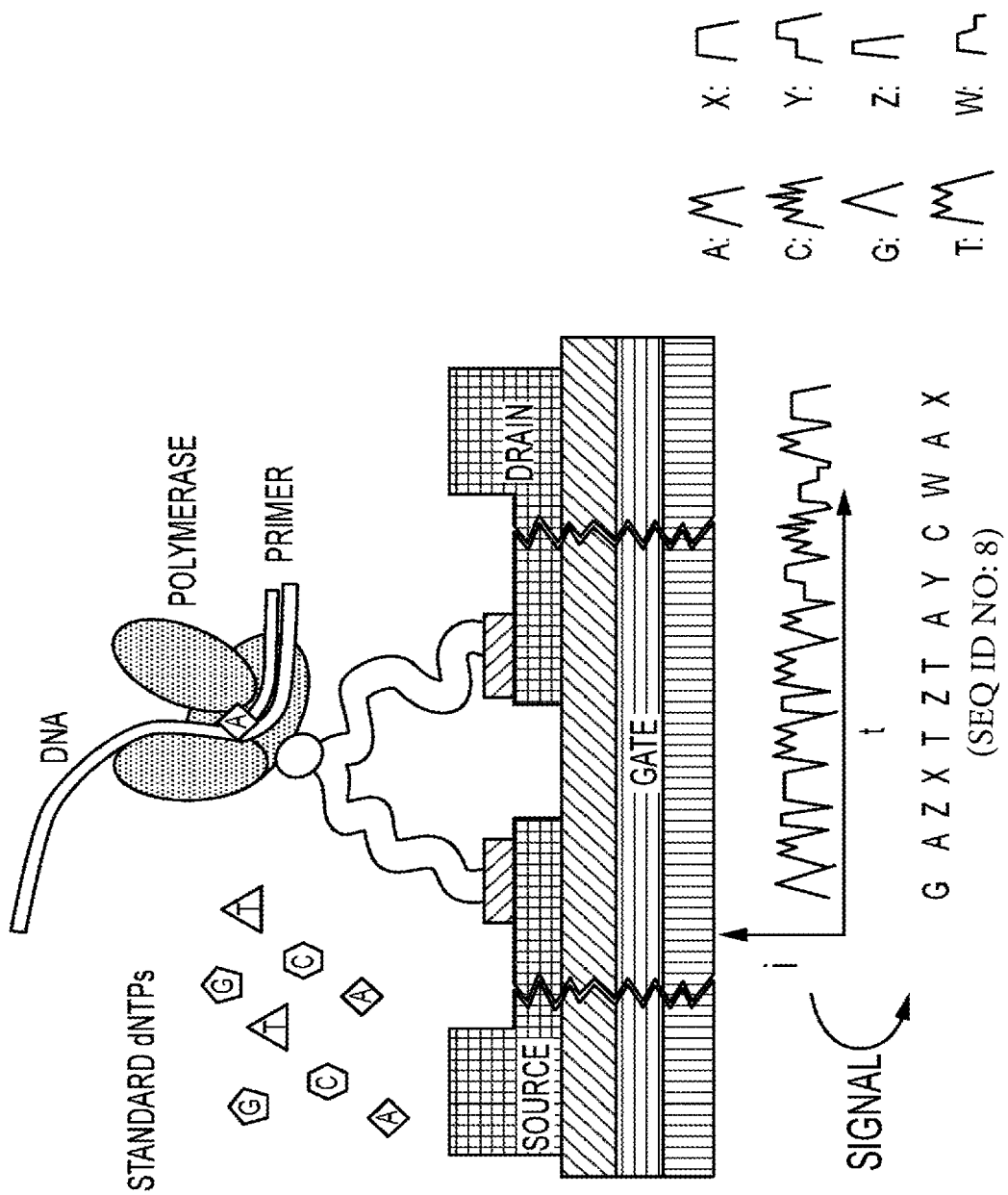
Figure 27A:
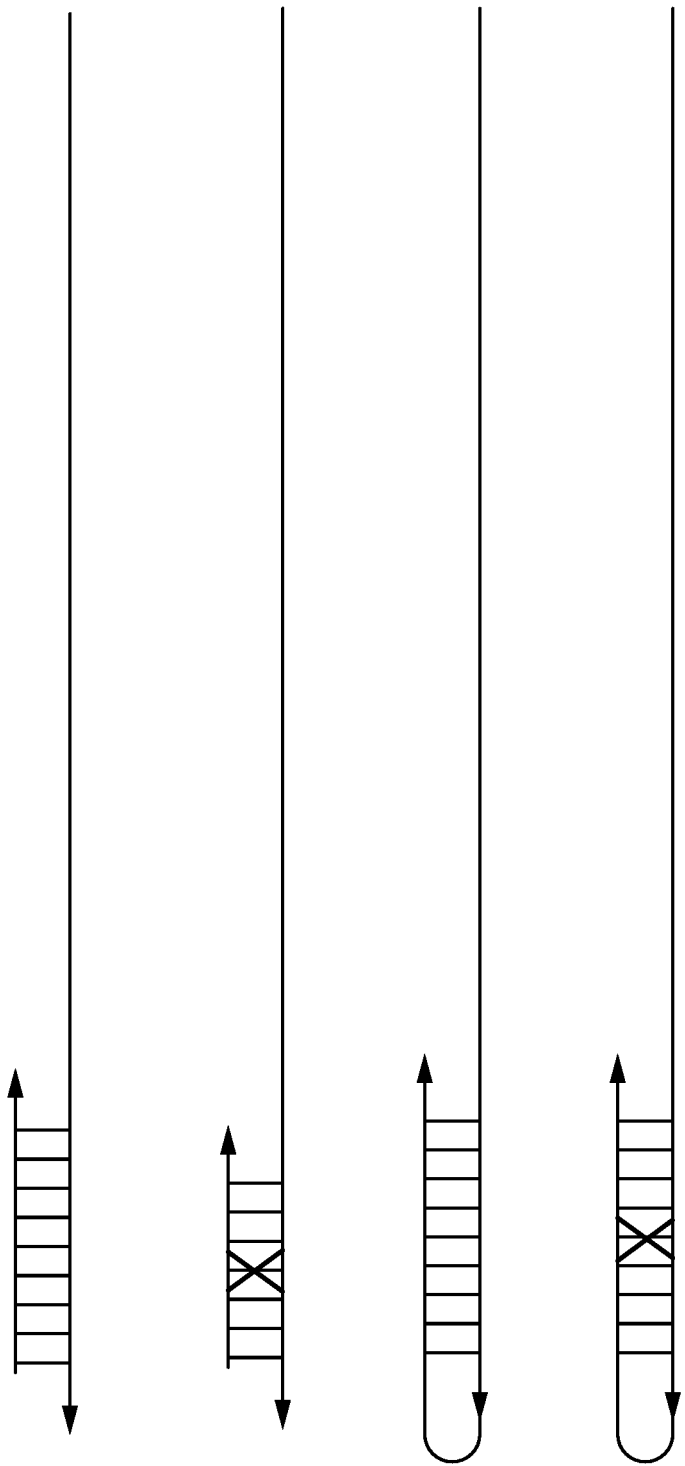
Figure 27B:
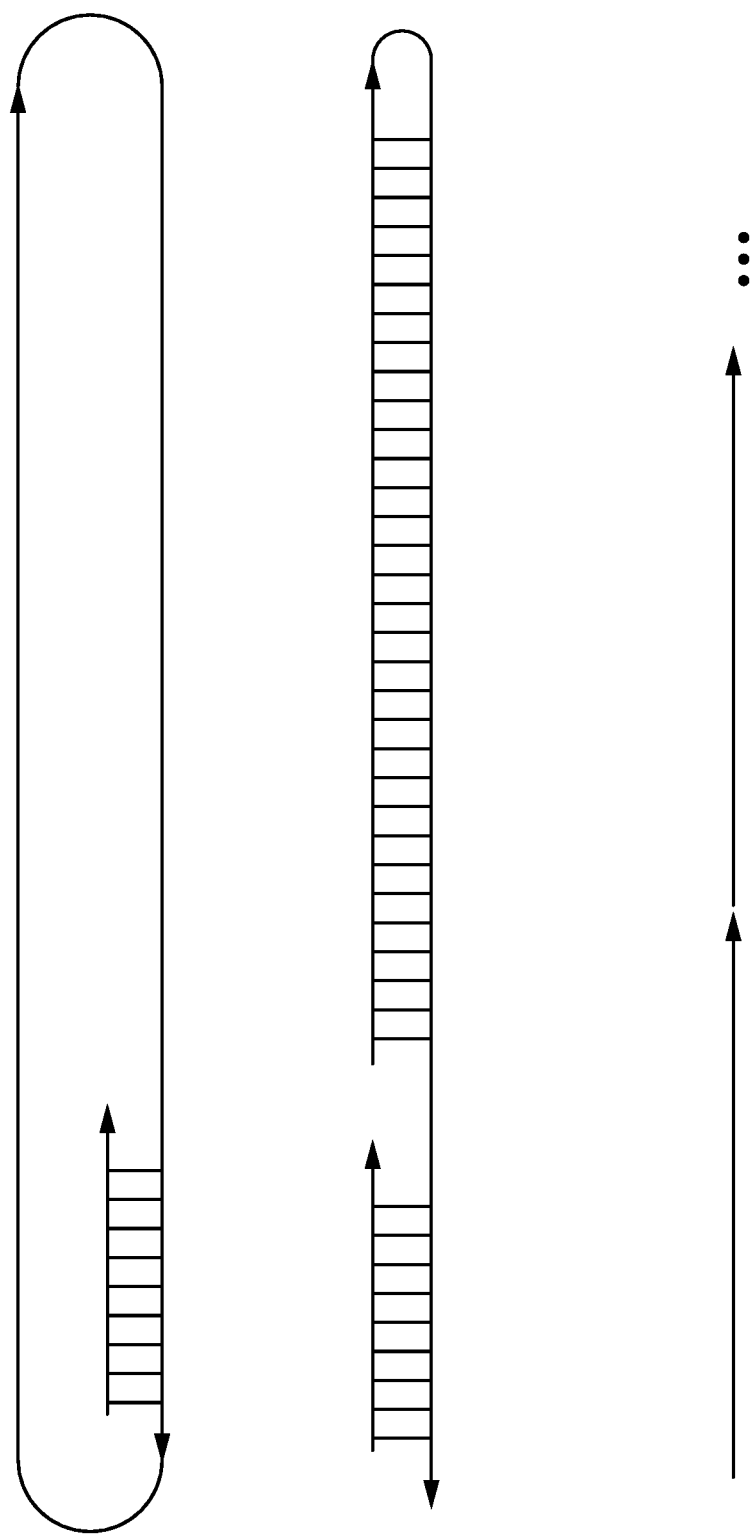
Figure 28:
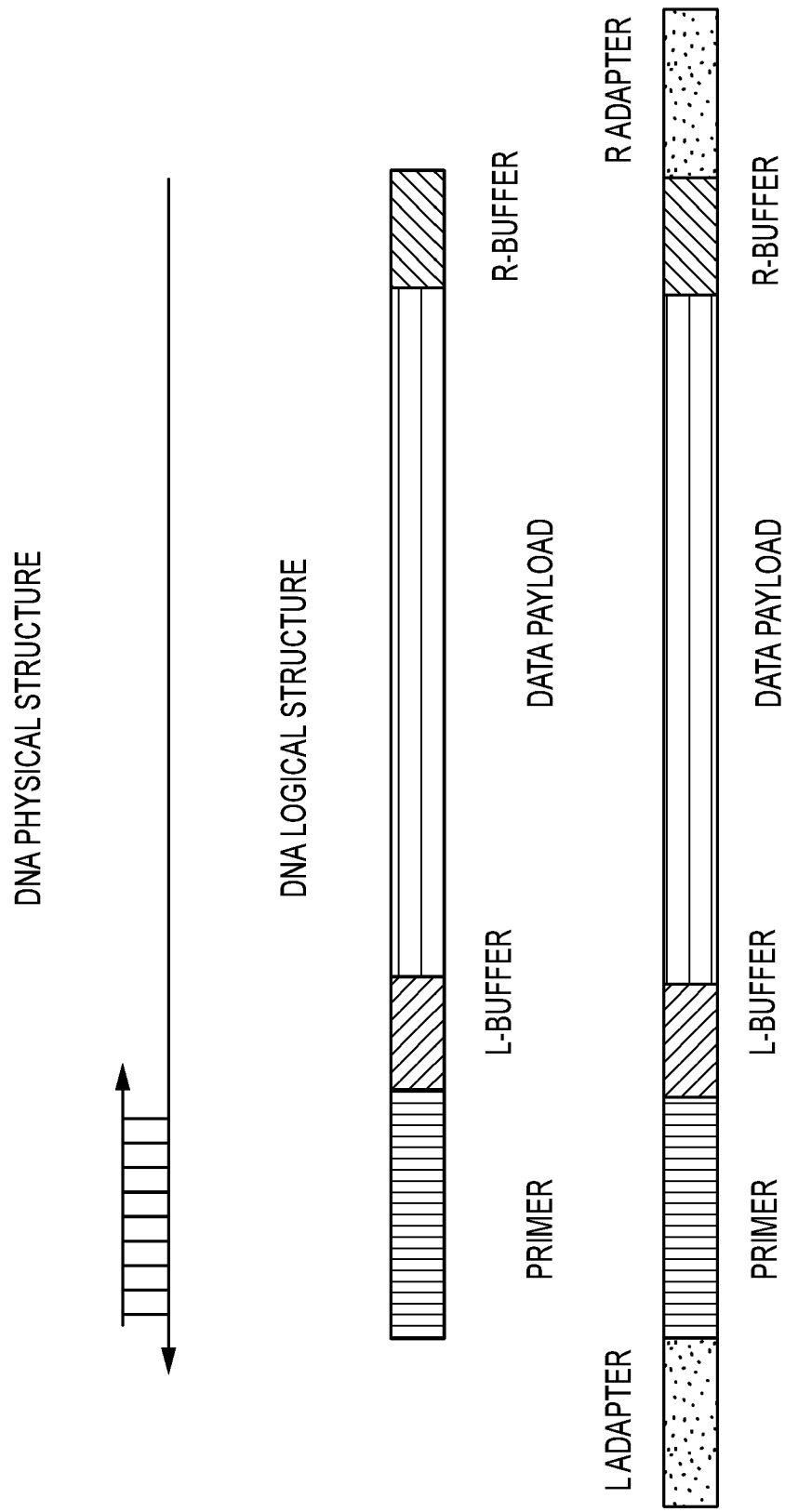
Figure 30A:
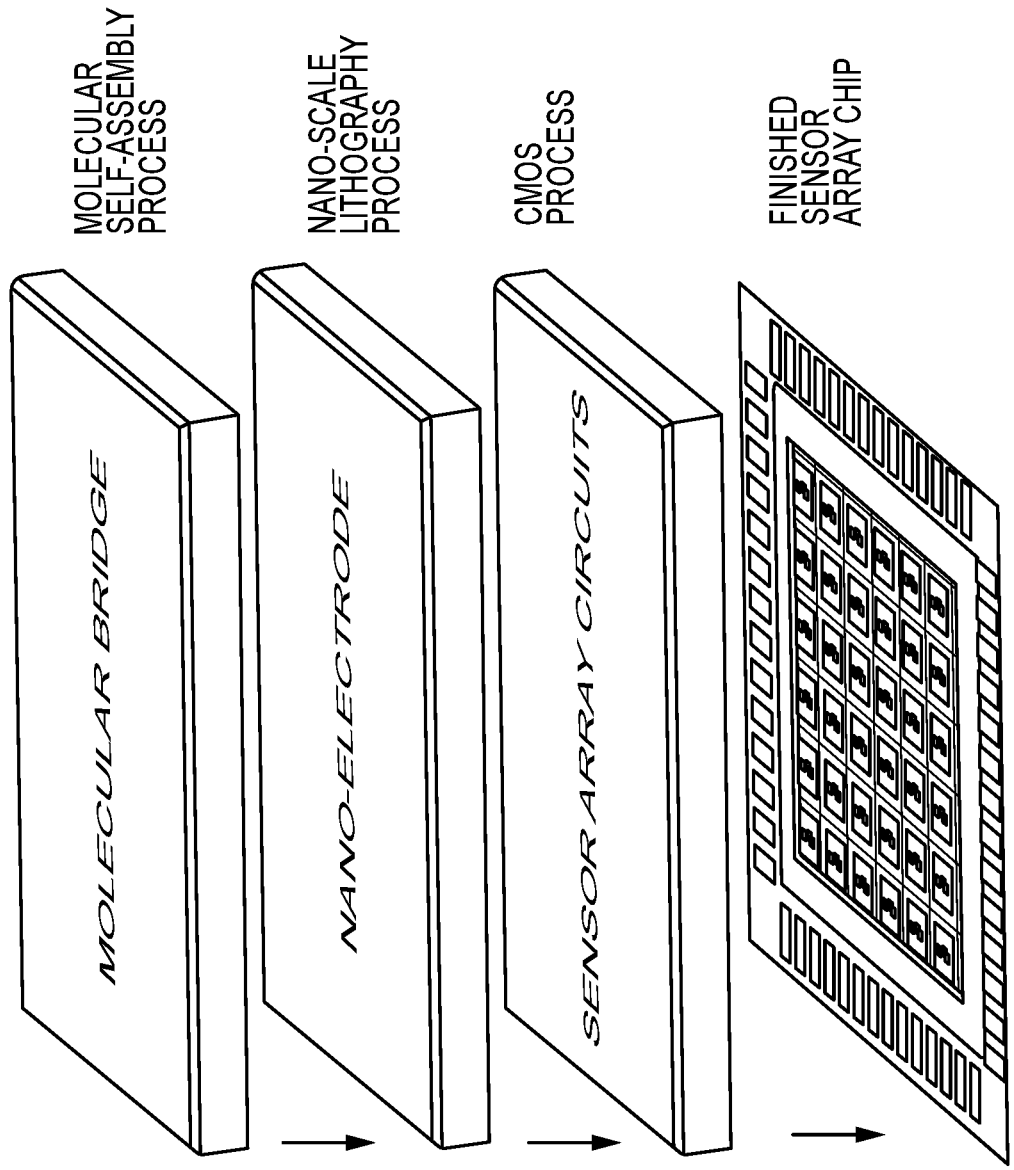
Figure 30B:
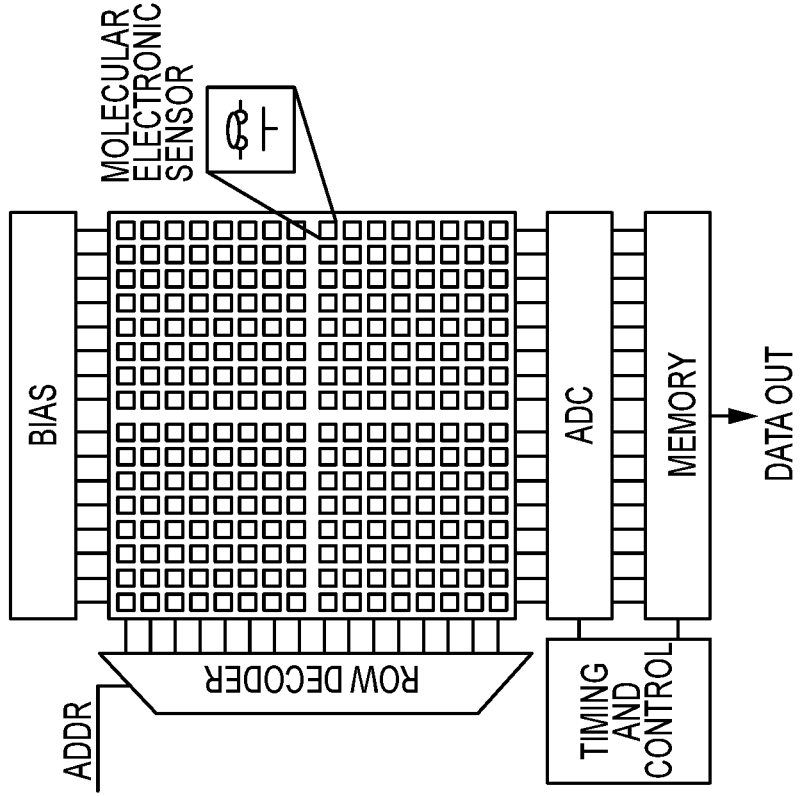
Figure 31:
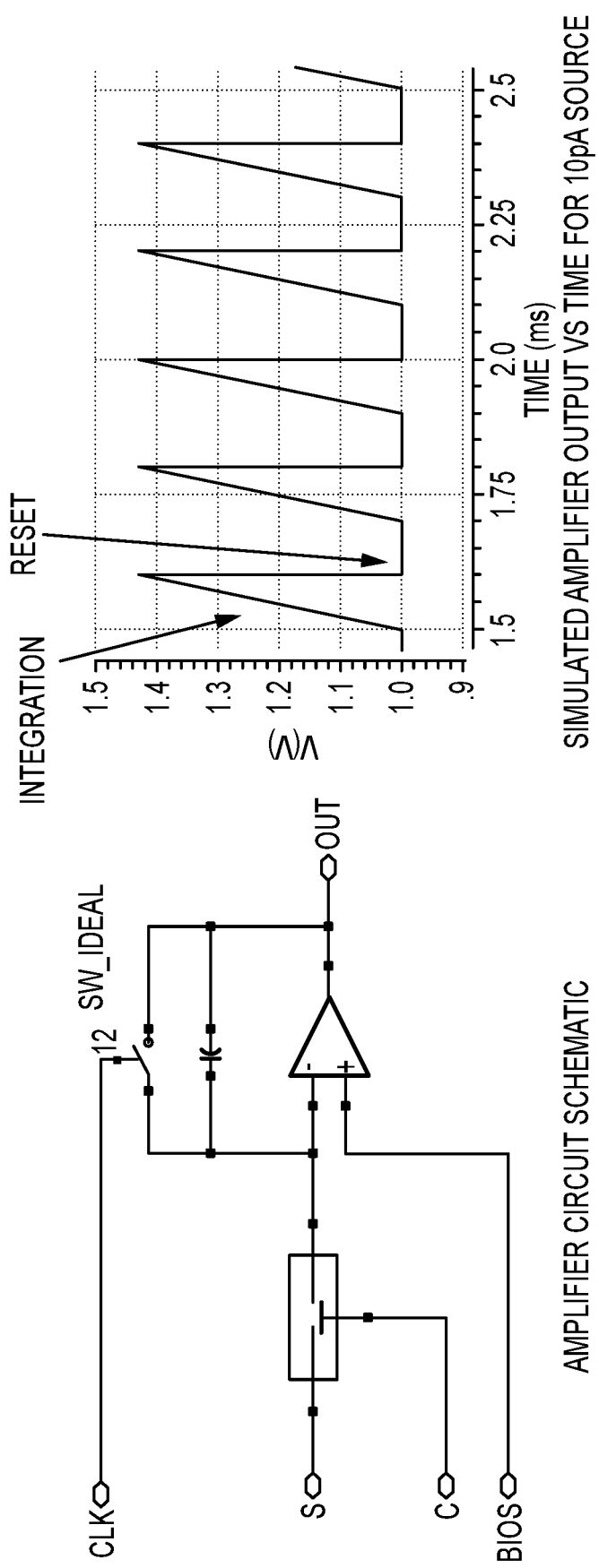
Figure 32:
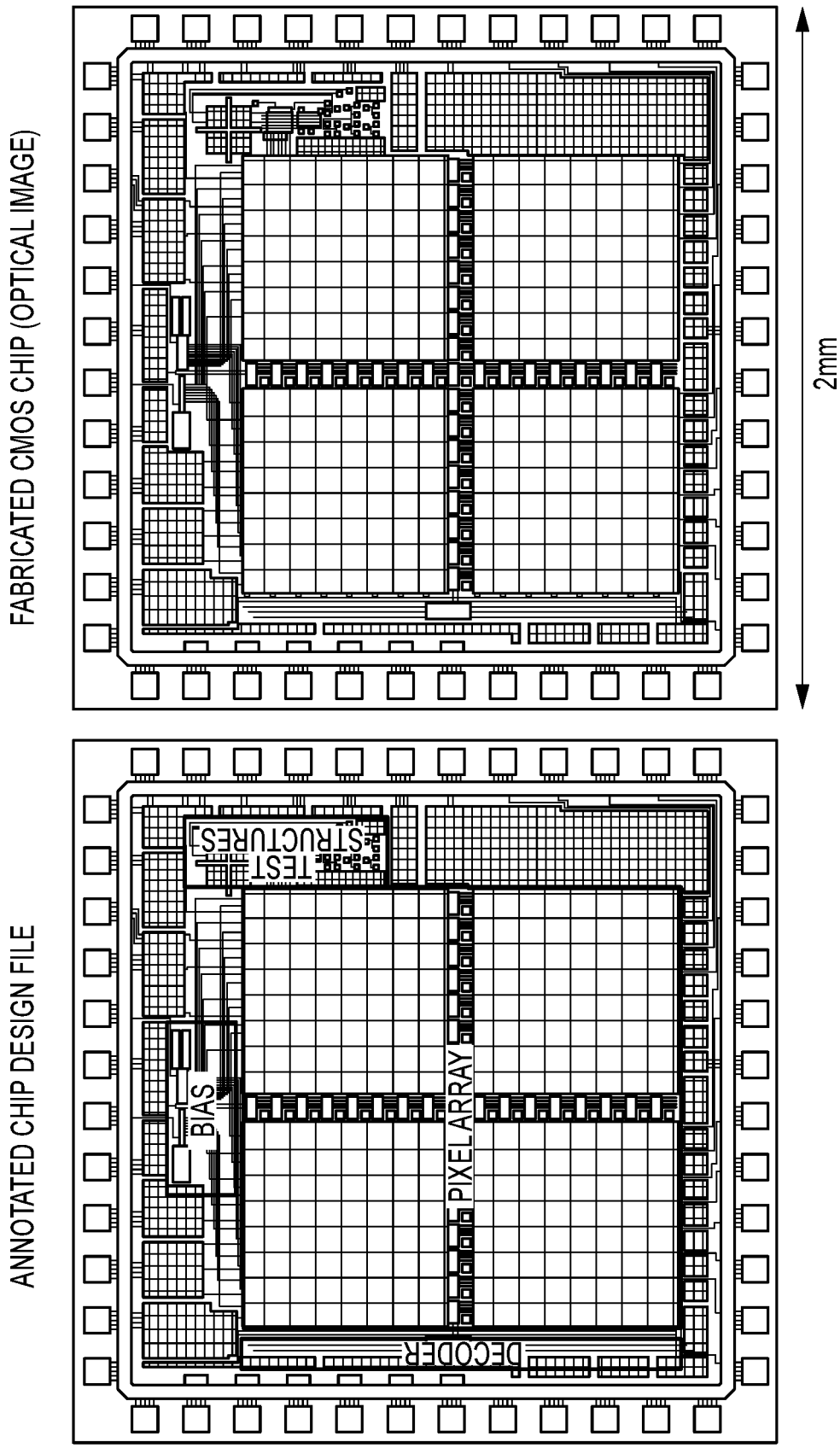
Figure 33:
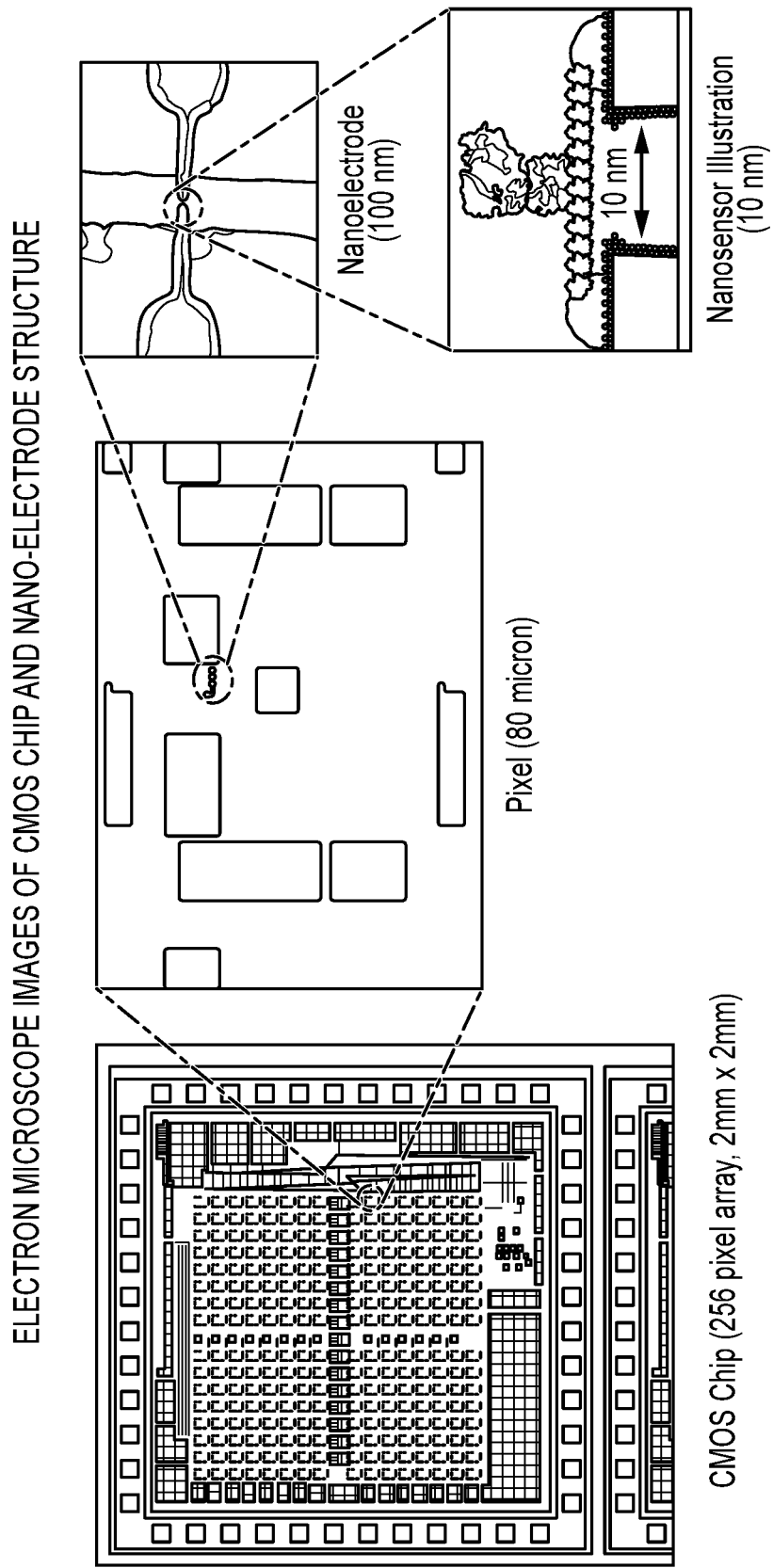
Figure 34:
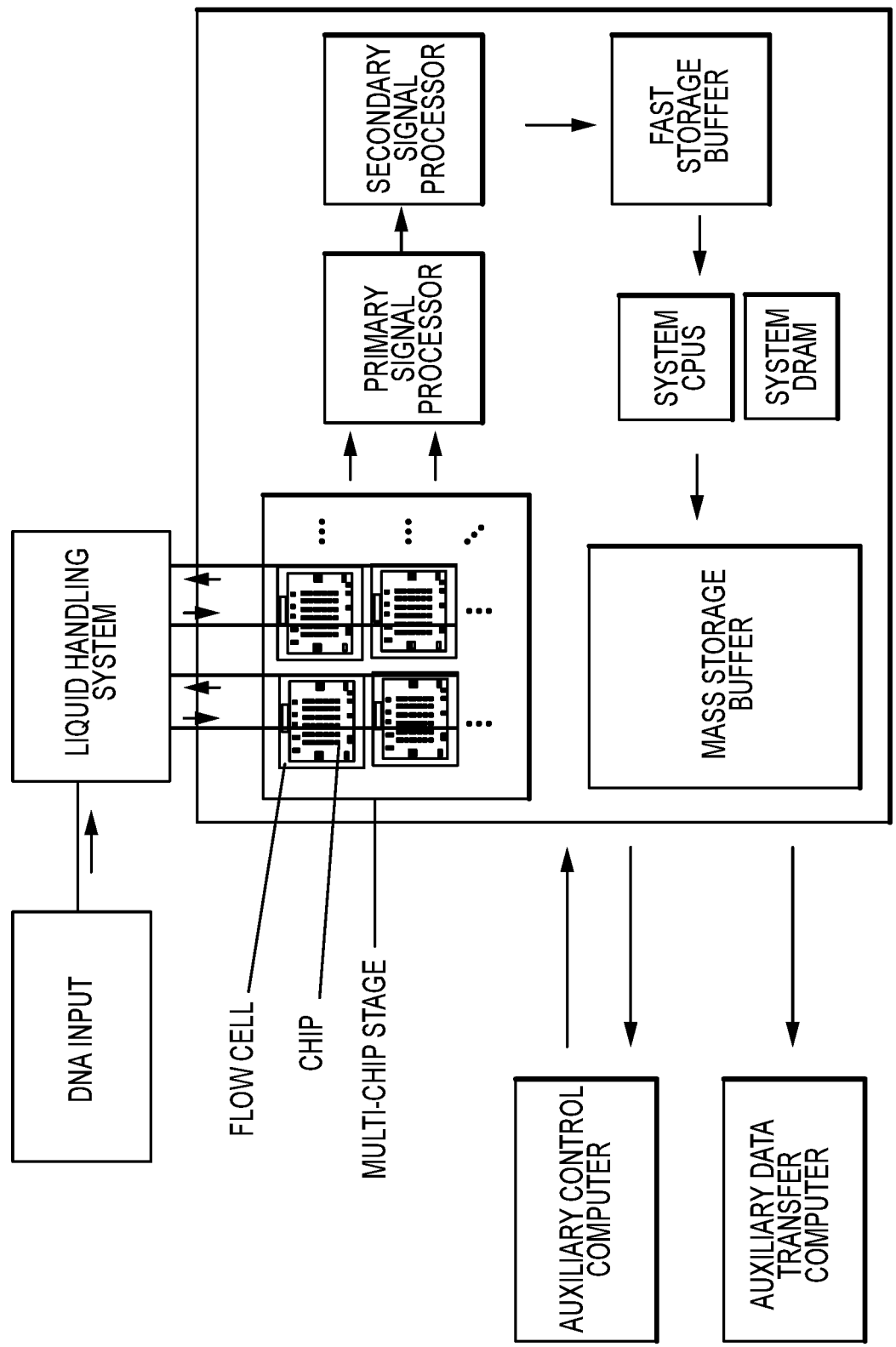
Figure 35:
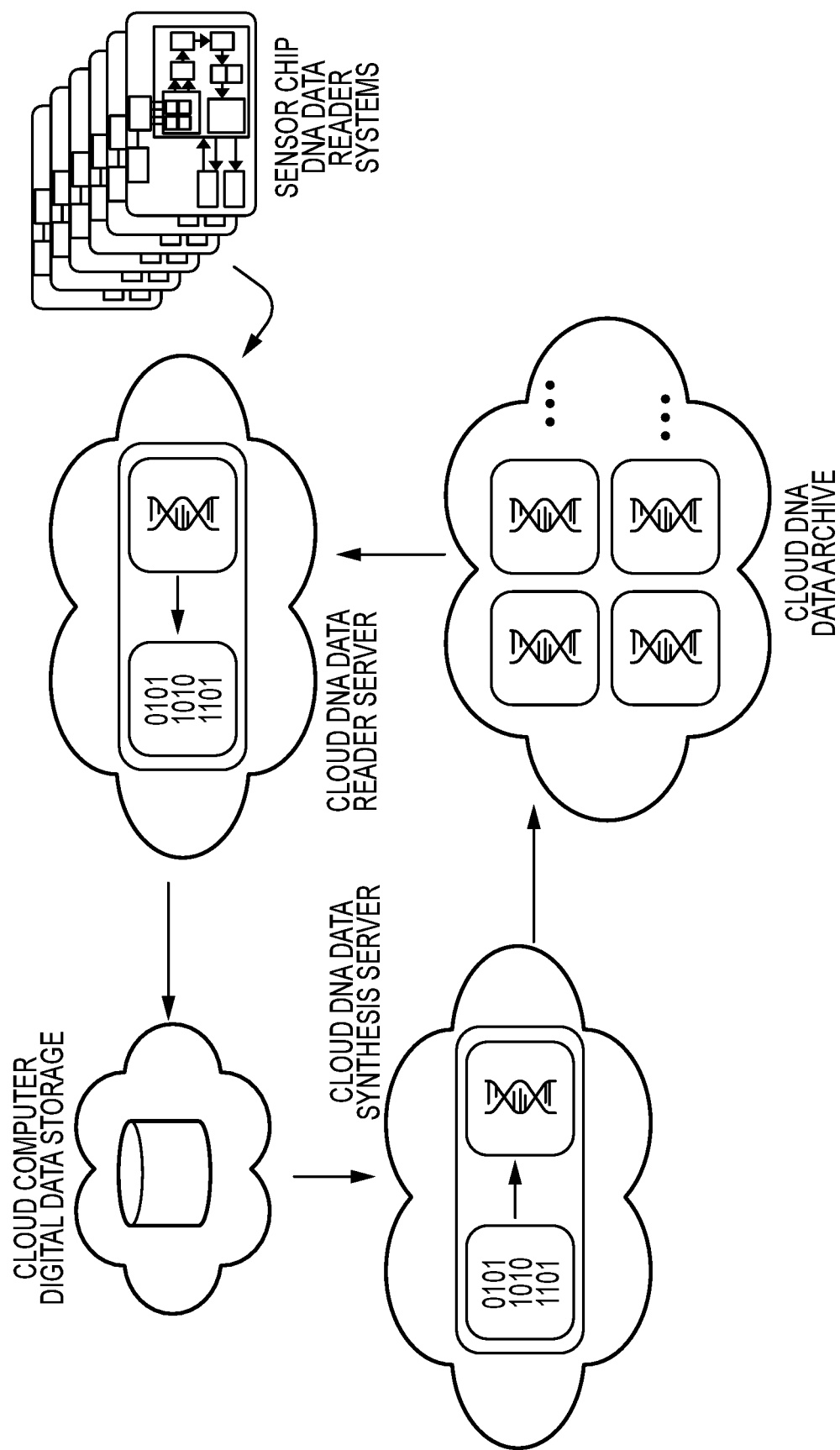
Figure 36:
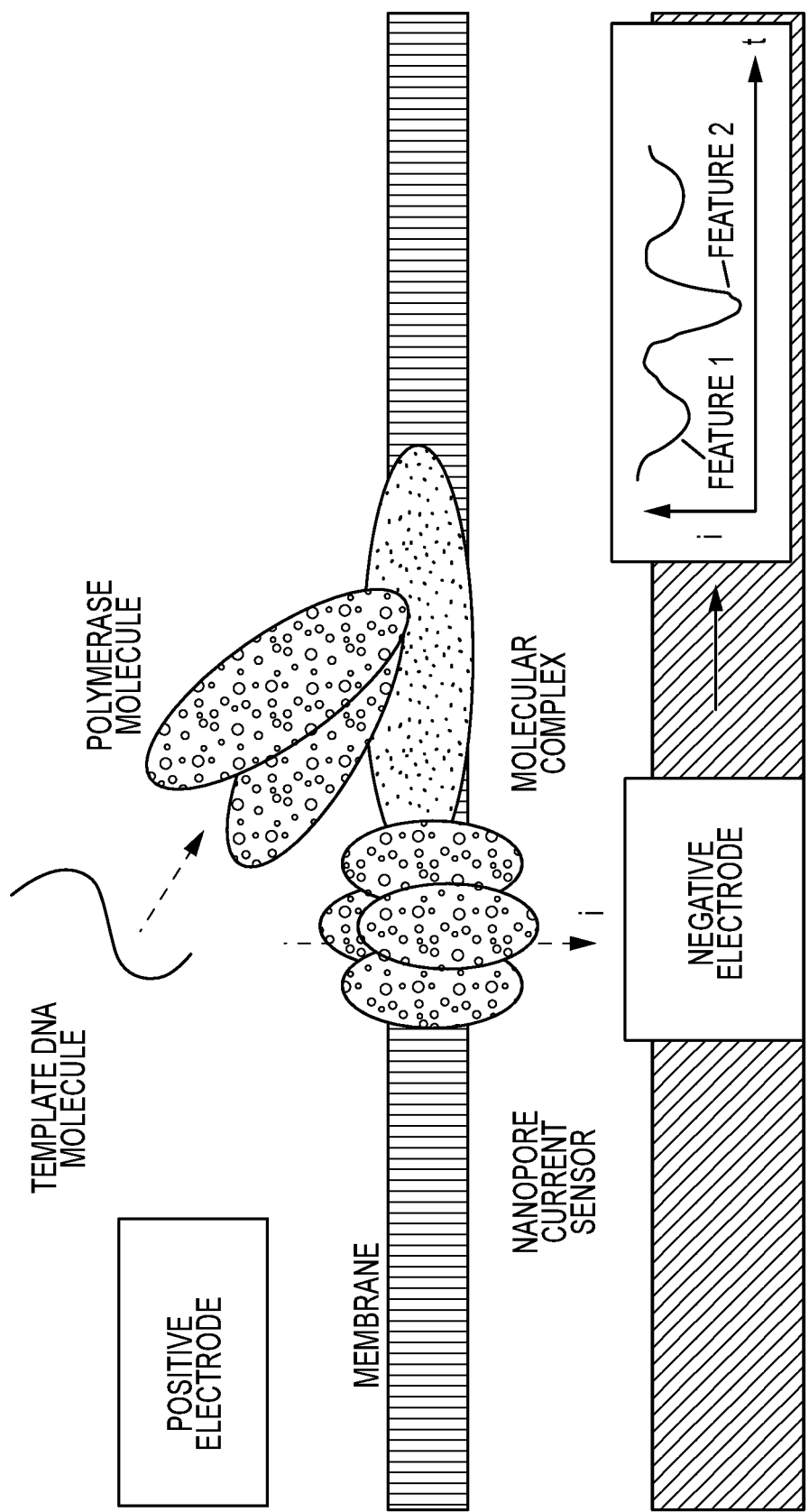
Figure 37:
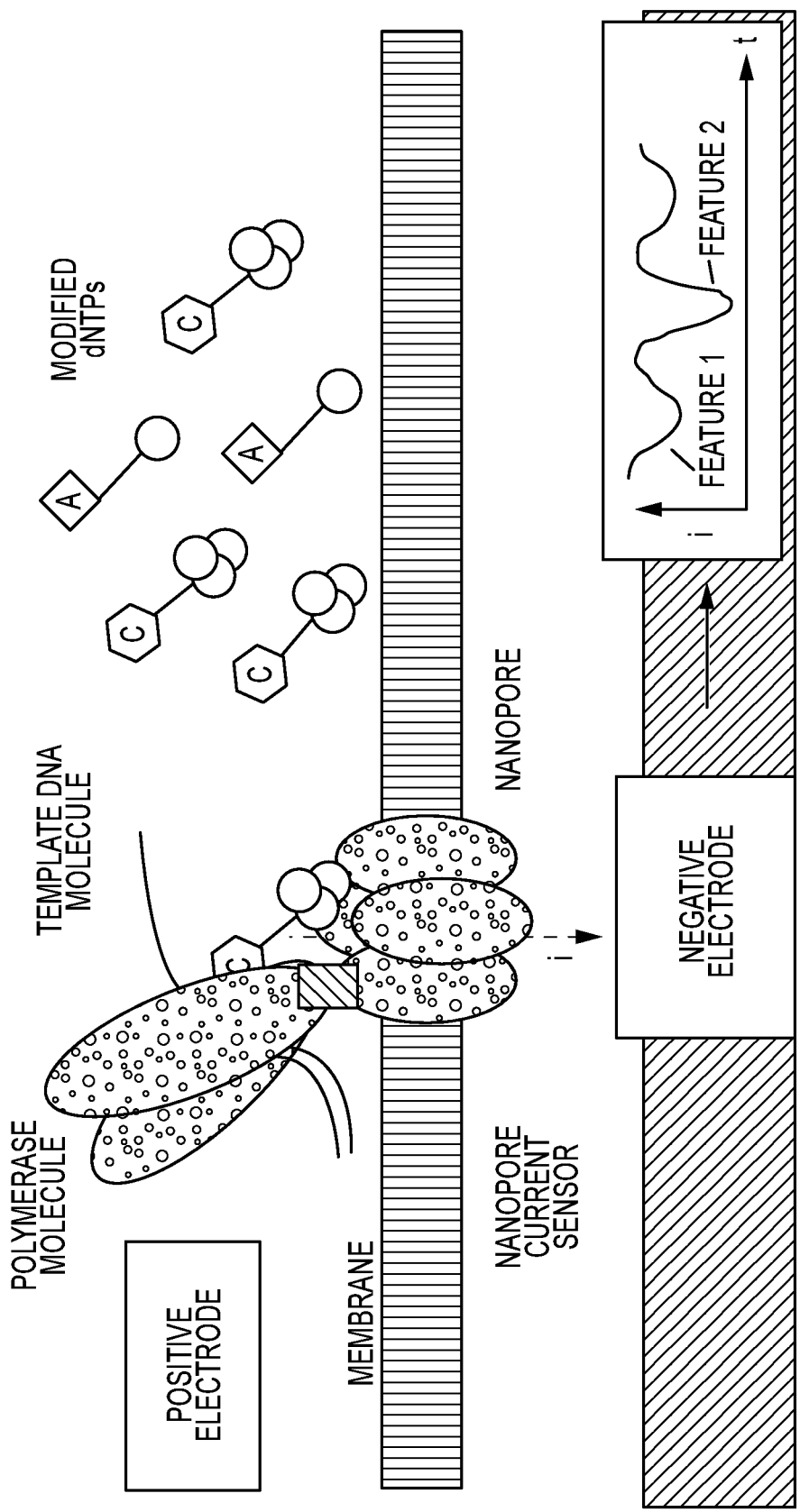
Figure 38:
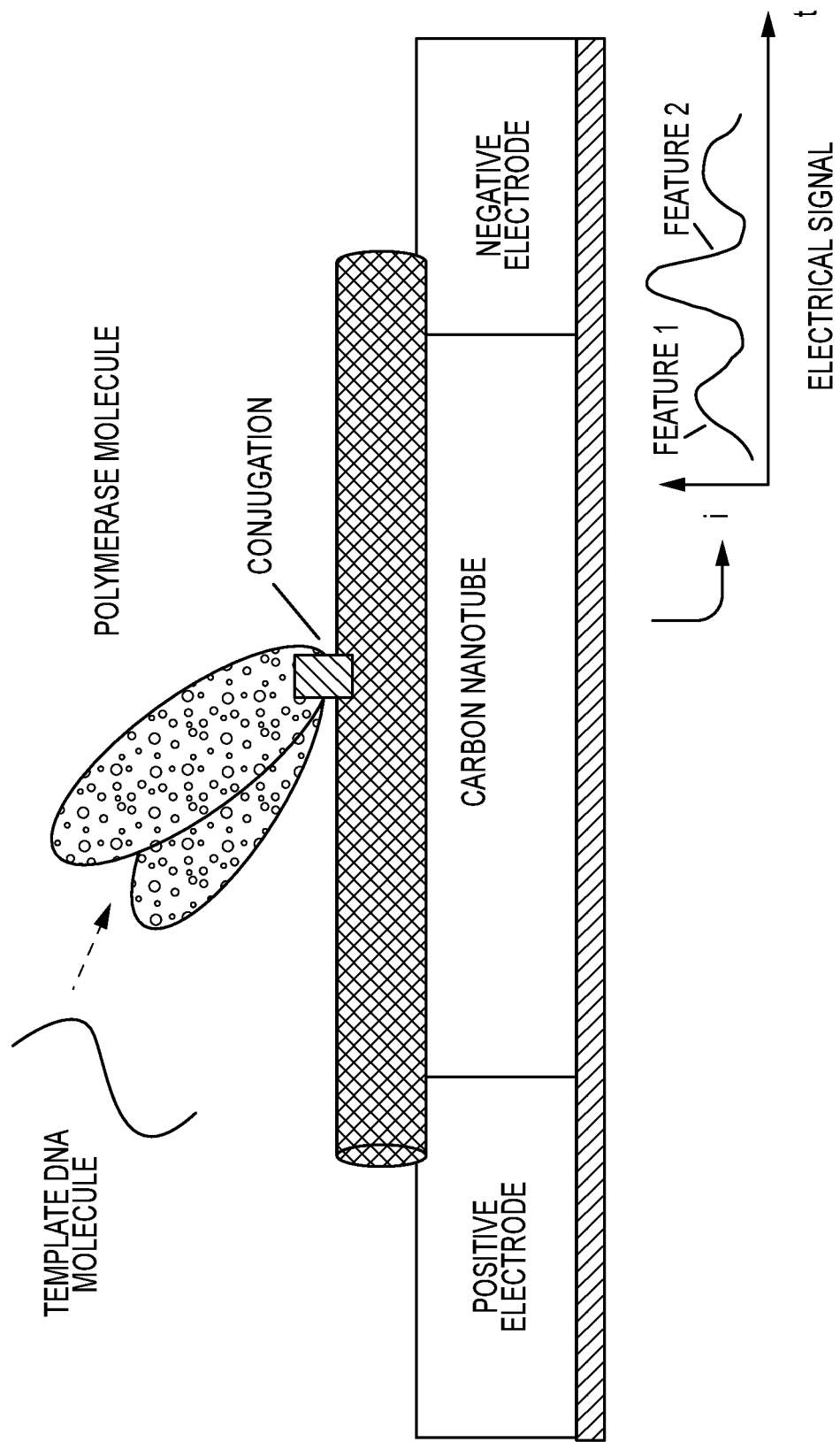
Figure 39:
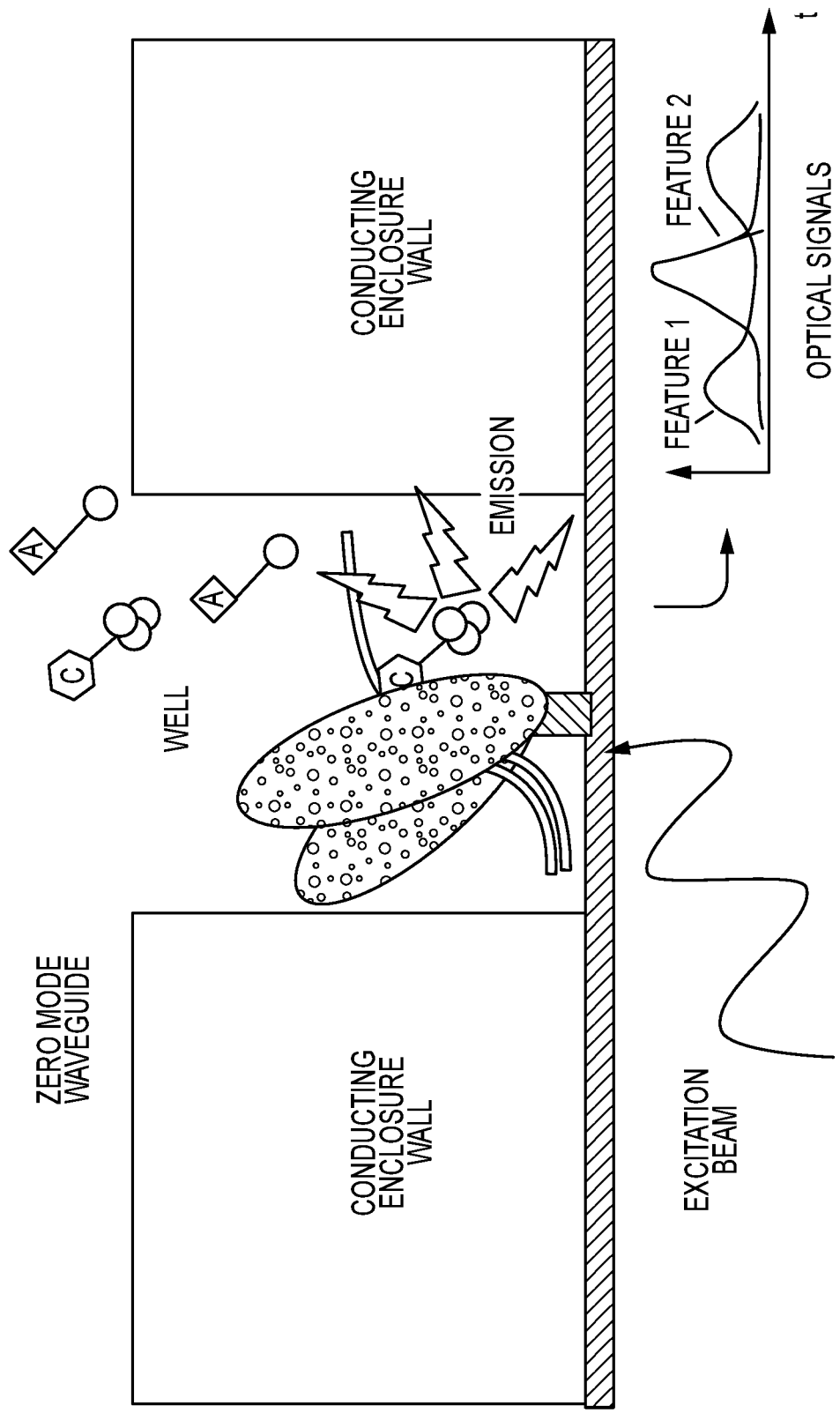

FIG. 20 sets forth three electron microscope (EM) images of electrodes (at increasing resolution) with gold metal dot contacts for bridge binding in sensors;

FIG. 21 shows current (pA) versus time (sec) plots obtained by measuring DNA incorporation signals with the sensor of FIG. 18;

FIG. 22 illustrates the use of modified dNTPs to produce enhanced signals from each base as the polymerase processes a template DNA, incorporating the modified dNTPs, in this case producing four distinguishable signal features;

FIG. 23 illustrates the use of two modified dNTPs, here modified dATP (A*) and dCTP (C*), to produce two distinguishable signals of incorporation, which provides a means to encode binary bits 0/1 into the template DNA;

FIG. 24 illustrates the use of two different sequence motifs, here homopolymers AA and CCC, to produce two distinguishable signals, which provides a means to encode binary bits 0/1 into the template DNA. In this case, AA and CCC provide two distinguishable sequence motifs that could be used for information encoding and recovery. Thus useful information encoding and reading is possible even without single base resolution of DNA sequence, by instead relying on distinguishable sequence motifs;

FIG. 25 shows actual experimental data, produced by an embodiment of the sensor of FIG. 18 in which specific sequence motifs of poly A and poly C produced distinguishable signals that are usable to encode 0/1 binary data;

FIG. 26A illustrates the use of two different sequence motifs, GATT and ACA, to produce two distinguishable signals that provide a method to encode binary bits 0/1 into the template DNA;

FIG. 26B illustrates the use of three different sequence motifs, here GATT, ACA and AGG, to produce three distinguishable signals, which provides a means to encode digital data with a three-state encoding;

FIG. 26C illustrates an embodiment where the encoding DNA is synthesized with base analogues, the standard modified bases X and Y, to produce 2 distinguishable signals when processed by polymerase with standard dNTPs, which provides a means to encode digital data with 2 state encoding, for example as in FIG. 17, BES4;

FIG. 26D illustrates an embodiment where the encoding DNA is synthesized with 8 different bases and base analogues, the standard A, C, G, T, and modified bases X, Y, Z, W, to produce 8 distinguishable signals when processed by polymerase with standard dNTPs, which provides a means to encode digital data with an 8 state encoding, for example as shown by scheme "BES5" in FIG. 29;

FIG. 27A sets forth different primer constructs that can be used in information-encoding DNA, such that templates can be presented in properly primed form for engagement with the polymerase of the sensor;

FIG. 27B sets forth embodiments of DNA template strand architectures that enable a polymerase-based sensor to interrogate the same DNA data payload multiple times;

FIG. 28 schematically illustrates how physical DNA structure relates to the logical structure of a DNA data storage molecule;

FIG. 29 sets forth various embodiments of binary data encoding schemes usable to encode a binary data payload into a DNA sequence, including examples of Binary Encoding Schemes ("BES") for representing a data payload as DNA sequence, along with primary translations between digital data and encoding DNA sequences;

FIG. 30A illustrates an embodiment of a fabrication stack usable to dispose individual DNA reader sensors on a chip in the form of massively parallel arrays;

FIG. 30B illustrates an embodiment of a high-level CMOS chip pixel array and details of a molecular electronics sensor circuit pixel in the array;

FIG. 31 shows a circuit schematic and simulated measurement for the pixel circuit of FIG. 30;

FIG. 32 illustrates an embodiment of an annotated chip design layout file and an optical microscope image of the corresponding finished chip for comparison;

FIG. 33 shows SEM images of the fabricated chip of FIG. 32, including insets of expanded resolution SEM images showing a pixel and nanoelectrodes with a polymerase molecular complex in place;

FIG. 34 shows a schematic of a complete system for reading DNA data with chip-based DNA reader sensors;

FIG. 35 shows a schematic of an embodiment of a cloud-based DNA data archival storage system, in which a multiplicity of the DNA reading system of FIG. 34 are aggregated to provide the data reader server;

FIG. 36 illustrates an alternate embodiment of a DNA data reader sensor in which a polymerase is complexed with a nanopore ion current sensor, producing distinguishable signal features in the nanopore ion current while processing DNA;

FIG. 37 shows an embodiment of a DNA data reader sensor wherein a polymerase is complexed with a nanopore ion current sensor, in which the polymerase is directly conjugated to the nanopore, and in which the dNTPs are modified by groups that interact with and alter the pore ion current during incorporation;

FIG. 38 illustrates an embodiment of DNA data reader sensor in which a polymerase is complexed with a carbon nanotube molecular wire spanning positive and negative electrodes, which produces distinguishable signal features in the measured current passing through the carbon nanotube; and FIG. 39 illustrates an embodiment of a Zero Mode Waveguide sensor complexed with a single polymerase, shown in cross section, that produces distinguishable optical signals corresponding to DNA features.

DETAILED DESCRIPTION

In various embodiments, a DNA data storage system utilizing DNA molecules as a general purpose means of digital information storage is disclosed. In certain aspects, a system for digital information storage comprises a DNA reading device, an information encoder/decoder algorithm, and a DNA writing device. In other aspects, the interrelation of these three elements and their co-optimization are disclosed.

In various embodiments, a data reader for a DNA data storage system is disclosed. In various aspects, a DNA reading device comprises a sensor that extracts information from a single DNA molecule. The sensor may be deployed in a chip-based format. In various examples, data reading systems that support such a chip-based sensor device are disclosed.

Definitions

As used herein, the term "DNA" refers to both biological DNA molecules and synthetic versions, such as made by nucleotide phosphoramidite chemistry, ligation chemistry or other synthetic organic methodologies. DNA, as used herein, also refers to molecules comprising chemical modifications to the bases, sugar, and/or backbone, such as known to those skilled in nucleic acid biochemistry. These include, but are not limited to, methylated bases, adenylated bases, other epigenetically marked bases, and non-standard or universal bases such as inosine or 3-nitropyrrole, or other nucleotide analogues, or ribobases, or abasic sites, or damaged sites. DNA also refers expansively to DNA analogues such as peptide nucleic acids (PNA), locked nucleic acids (LNA), and the like, including the biochemically similar RNA molecule and its synthetic and modified forms. All these biochemically closely related forms are implied by the use of the term DNA, in the context of the data storage molecule used in a DNA data storage system herein. Further, the term DNA herein includes single stranded forms, double helix or double-stranded forms, hybrid duplex forms, forms containing mismatched or non-standard base pairings, non-standard helical forms such as triplex forms, and molecules that are partially double stranded, such as a single-stranded DNA bound to a oligo primer, or a molecule with a hairpin secondary structure. Generally as used herein, the term DNA refers to a molecule comprising a single-stranded component that can act as the template for a polymerase enzyme to synthesize a complementary strand therefrom.

DNA sequences as written herein, such as GATTACA, refer to DNA in the 5' to 3' orientation, unless specified otherwise. For example, GATTACA as written herein represents the single stranded DNA molecule 5'-G-A-T-T-A-C-A-3'. In general, the convention used herein follows the standard convention for written DNA sequences used in the field of molecular biology.

As used herein, the term "polymerase" refers to an enzyme that catalyzes the formation of a nucleotide chain by incorporating DNA or DNA analogues, or RNA or RNA analogues, against a template DNA or RNA strand. The term polymerase includes, but is not limited to, wild-type and mutant forms of DNA polymerases, such as Klenow, E. Coli Pol I, Bst, Taq, Phi29, and T7, wild-type and mutant forms of RNA polymerases, such as T7 and RNA Pol I, and wild-type and mutant reverse transcriptases that operate on an RNA template to produce DNA, such as AMV and MMLV.

As used herein, the term "dNTP" refers to both the standard, naturally occurring nucleoside triphosphates used in biosynthesis of DNA (i.e., dATP, dCTP, dGTP, and dTTP), and natural or synthetic analogues or modified forms of these, including those that carry base modifications, sugar modifications, or phosphate group modifications, such as an alpha-thiol modification or gamma phosphate modifications, or the tetra-, penta-, hexa- or longer phosphate chain forms, or any of the aforementioned with additional groups conjugated to any of the phosphates, such as the beta, gamma or higher order phosphates in the chain. In general, as used herein, "dNTP" refers to any nucleoside triphosphate analogue or modified form that can be incorporated by a polymerase enzyme as it extends a primer, or that would enter the active pocket of such an enzyme and engage transiently as a trial candidate for incorporation.

As used herein, "buffer," "buffer solution" and "reagent solution" refers to a solution which provides an environment in which the polymerase sensor can operate and produce signals from supplied templates. In various embodiments, the solution is aqueous. The buffer, buffer solution or reagent solution may comprise components such as salts, pH buffers, divalent cations, detergents, blocking agents, solvents, template primer oligos, proteins that complex with a polymerase, and polymerase substrates, (e.g., dNTPs, analogues or modified forms of dNTPs, and DNA substrates or templates).

As used herein, "binary data" or "digital data" refers to data encoded using the standard binary code, or a base 2 {0,1} alphabet, data encoded using a hexadecimal base 16 alphabet, data encoded using the base 10 {0-9} alphabet, data encoded using ASCII characters, or data encoded using any other discrete alphabet of symbols or characters in a linear encoding fashion.

As used herein, "digital data encoded format" refers to a series of binary digits, or other symbolic digits or characters that come from the primary translation of DNA sequence features used to encode information in DNA, or the equivalent logical string of such classified DNA features. In some embodiments, information to be archived as DNA may be translated into binary, or may exist initially as binary data, and then this data may be further encoded with error correction and assembly information, into the format that is directly translated into the code provided by the distinguishable DNA sequence features. This latter association is the primary encoding format of the information. Application of the assembly and error correction procedures is a further, secondary level of decoding, back towards recovering the source information.

As used herein, "distinguishable DNA sequence features" means those features of a data-encoding DNA molecule that, when processed by a sensor polymerase, produce distinct signals that can be used to encode information. Such features may be, for example, different bases, different modified bases or base analogues, different sequences or sequence motifs, or combinations of such to achieve features that produce distinguishable signals when processed by a sensor polymerase.

As used herein, a "DNA sequence motif" refers to both a specific letter sequence or a pattern representing any member of a specific set of such letter sequences. For example, the following are sequence motifs that are specific letter sequences: GATTACA, TAC, or C. In contrast, the following are sequence motifs that are patterns: G[A/T]A is a pattern representing the explicit set of sequences {GAA, GTA}, and G[2-5] is a pattern referring to the set of sequences {GG, GGG, GGGG, GGGGG}. The explicit set of sequences in the unambiguous description of the motif, while such pattern shorthand notations as those are common compact ways of describing such sets. Motif sequences such as these may be describing native DNA bases, or may be describing modified bases, in various contexts. In various contexts, the motif sequences may be describing the sequence of a template DNA molecule, and/or may be describing the sequence on the molecule that complements the template.

As used herein, "sequence motifs with distinguishable signals," in the cases of patterns, means that there is a first motif pattern representing a first set of explicit sequences, and any of said sequences produces the first signal, and there is a second motif pattern representing a second set of explicit sequences, and any of said sequences produces the second signal, and the first signal is distinguishable from the second signal. For example, if motif G[A/T]A and motif G[3-5] produce distinguishable signals, it means that any of the set {GAA, GTA} produce a first signal, and any of the set {GGG,GGGG,GGGGG} produce a second signal, distinguishable from the first.

As used herein, "distinguishable signals" refers to one electrical signal from a sensor being discernably different than another electrical signal from the sensor, either quantitatively (e.g., peak amplitude, signal duration, and the like) or qualitatively, (e.g., peak shape, and the like), such that the difference can be leveraged for a particular use. In a non-limiting example, two current peaks versus time from an operating molecular sensor are distinguishable if there is more than about a $1 \times 10^{-10}$ Amp difference in their amplitudes. This difference is sufficient to use the two peaks as two distinct binary bit readouts, e.g., a 0 and a 1. In some instances, a first peak may have a positive amplitude, e.g., from about $1 \times 10^{-10}$ Amp to about $20 \times 10^{-10}$ Amp amplitude, whereas a second peak may have a negative amplitude, e.g., from about 0 Amp to about $-5 \times 10^{-10}$ Amp amplitude, making these peaks discernably different and usable to encode different binary bits, i.e., 0 or 1.

As used herein, a "data-encoding DNA molecule," or "DNA data encoding molecule," refers to a molecule synthesized to encode data in DNA, or copies or other DNA derived from such molecules.

As used herein, "reading data from DNA" refers to any method of measuring the distinguishable signals that correspond to the DNA molecular features that were used to encode information into the DNA molecule.

As used herein, electrodes refer to nano-scale conducting metal elements, with a nanoscale-sized gap between two electrodes in an individual pair of electrodes, and, in some embodiments, comprising a gate electrode capacitively coupled to the gap region, which may be a buried or "back" gate, or a side gate. The electrodes may be referred to as "source" and "drain" electrodes in some contexts, or as "positive" and "negative" electrodes, such terminologies being common in electronics. Nano-scale electrodes will have a gap width between each electrode in a pair of electrodes in the 1 nm-100 nm range, and will have other critical dimensions, such as width and height and length, also in this range. Such nano-electrodes may comprise a variety of materials that provide conductivity and mechanical stability, such as metals, or semiconductors, for example, or of a combination of such materials. Examples of metals for electrodes include titanium and chromium.

General aspects of a DNA data storage system in accordance to the present disclosure, usable for archiving and later accessing stored data, are disclosed in reference to various drawing figures.

Figure 1:
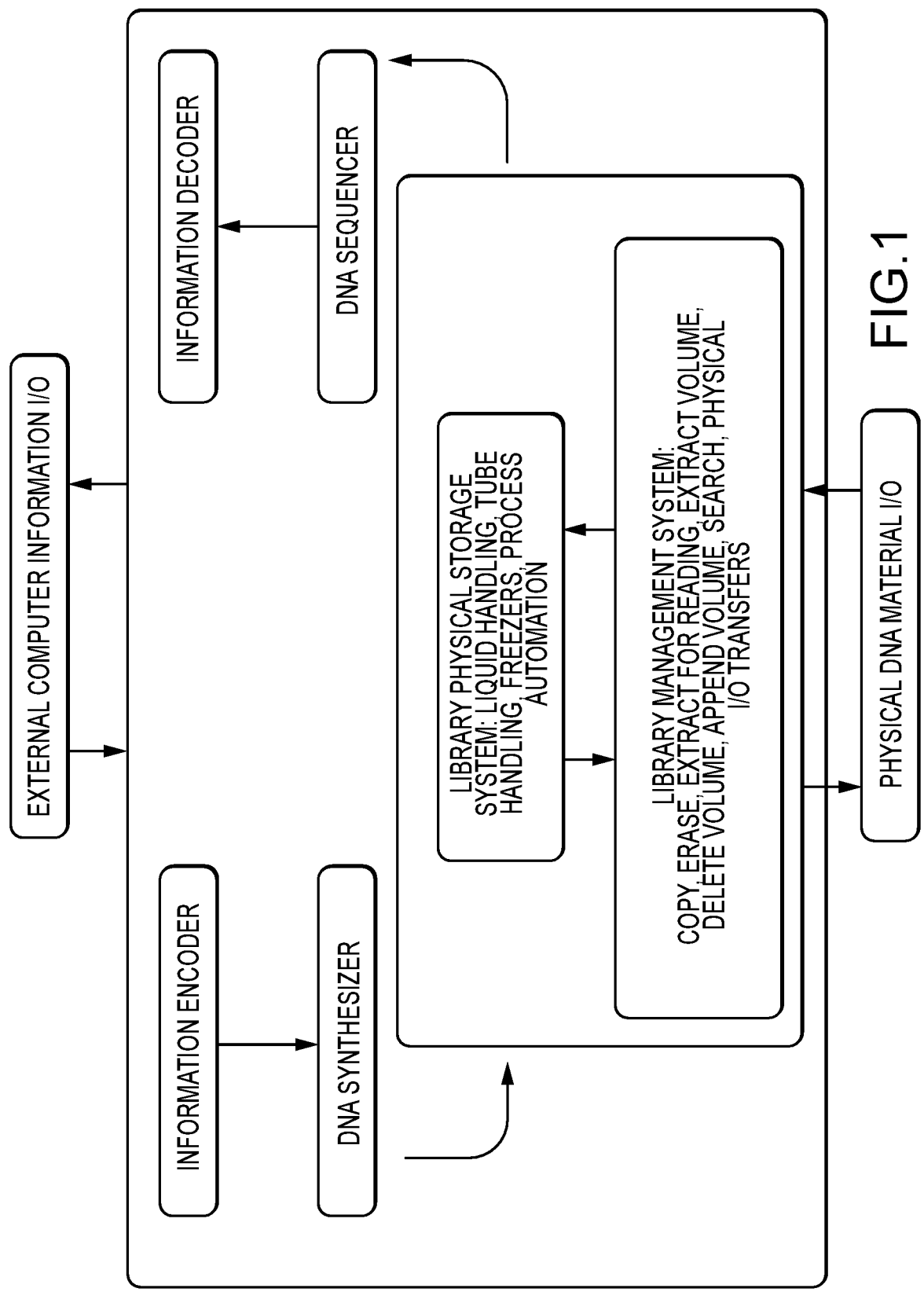
FIG. 1 illustrates elements of an embodiment of a DNA information storage system.

FIG. 1 illustrates an embodiment of a DNA information storage system in accordance with the present disclosure. This example shows the major elements of a DNA storage system, including the physical system used to handle and maintain the DNA material during storage, and which carries out operations on the stored archive, such as copying. An external computer provides a high level control of the system, supplying information for storage, and receiving extracted information. Information is encoded as DNA sequences, synthesized, stored, and then read, decoded and output. In addition, such a system is capable of physical I/O of the DNA archive material samples as well.

Figure 2:
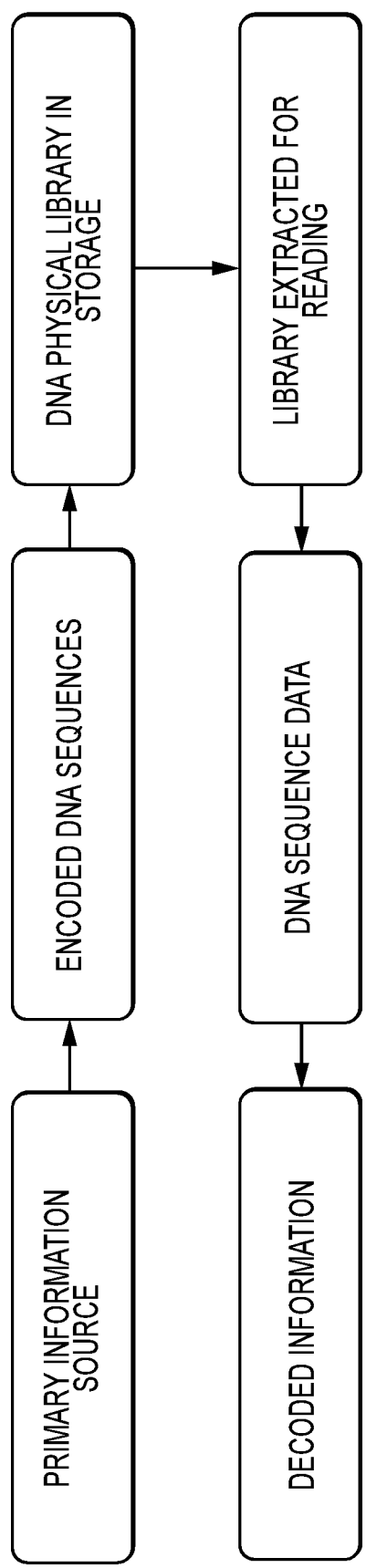
FIG. 2 illustrates a generalized view of primary DNA storage system information phases and processes.

FIG. 2 illustrates primary DNA storage system information phases and processes, including the major phases of information existing in the overall system (depicted in FIG. 2 as boxes), along with the primary operations transitioning from one form to another (depicted in FIG. 2 by arrows).

In various aspects of the present disclosure, a DNA information storage system comprises: (a) an encoder/decoder; a DNA writing device; and a DNA reading device.

Encoder/Decoder:

In various aspects, the encoder/decoder comprises an algorithm with two functions: the encoder portion translates given digital/binary information into a specific set of DNA sequences that are inputs to the DNA writer. The decoder portion translates a given set of DNA sequences of the type provided by the DNA reader, back into digital information.

DNA Writing Device:

In various aspects, the DNA writing device comprises any device that takes a given set of DNA sequences and synthesizes DNA molecules from these sequences (see, for e.g.: Kosuri and Church, "Large Scale de novo DNA synthesis: technologies and applications. Nature Methods, 11: 499-509, 2014). Non-limiting examples of methods and devices for synthesizing DNA molecules include commercial technology offered by Agilent Technologies and Twist BioScience. For each desired sequence, multiple DNA molecules representing that sequence are produced. The multiplicity of molecules produced can be in the ranges of 10's, 100's, 1000's, millions or even billions of copies of DNA molecules for each desired sequence. All of these copies representing all the desired sequences may be pooled into one master pool of molecules. It is typical of such DNA writing systems that the writing is not perfect, and if N molecules are synthesized to represent a given input sequence, not all of these will actually realize the desired sequence. For example, they may contain erroneous deletions, insertions, or incorrect or physically damaged bases.

DNA Reading Device:

In various aspects, the DNA reading device is a device that takes a pool of DNA molecules and produces a set of measured DNA sequences for molecules sampled or selected from this pool. Such readers actually survey only a small portion of the DNA molecules introduced into the system, so that only a small fraction will undergo an actual read attempt. It is further typical of such DNA reading devices that a given DNA molecule that is processed may not be read with entire accuracy, and thus there may be errors present in the read. As a result, it is also typical that the measured sequence outputs include various forms of confidence estimates and missing data indicators. For example, for each letter in a measure sequence, there may be a confidence probability or odds that it is correct, versus the other three DNA letter options, and there may be missing data indicators that indicate the identity of a letter is unknown, or there may be a set of optional sequence candidates with different probabilities representing a portion of a read.

The three major elements of a DNA data storage system in accordance to the present disclosure, as set forth above, have certain roles and interrelations, as detailed further below.

The Relation Between Major Elements, and the Central Role of the Encoder/Decoder:

The information encoder/decoder is selected based on the properties of the DNA writer and DNA reader devices, so as to minimize or reduce some overall measure of the cost of the information storage/retrieval process. One key component of system cost is the overall error rate in retrieved information. Errors and costs are diagrammatically illustrated in FIGS. 3-9.

Figure 3:
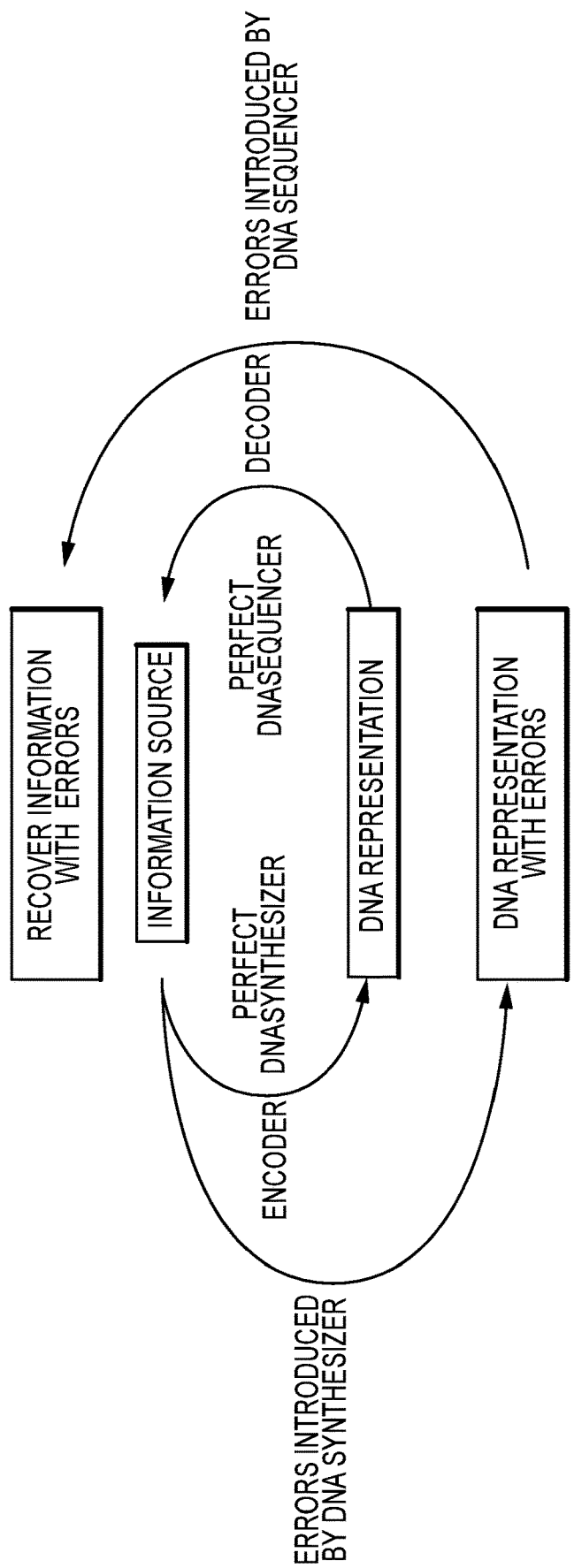
FIG. 3 illustrates the need for error compensation by diagrammatically showing the perfect process versus a process wherein errors are introduced in reading and writing DNA.

In general, a DNA writer device can introduce writing errors, and a DNA reading device can produce reading errors, and so the processes of storing information in the system and then later retrieving it potentially results in an error rate seen in the retrieved information. As diagrammatically illustrated in FIG. 3, there is a need to compensate for errors in the system. FIG. 3 illustrates the need for error correction, error avoidance, or some form of error compensation since encoding information followed by the decoding of the information will otherwise generally not result in the original information returned, primarily due to physiochemical errors in the reading and writing of DNA. The encoder/decoder algorithm can be chosen to minimize or reduce this error rate, based on the error properties and propensities of the DNA reader and DNA writer. These embodiments are illustrated in FIGS. 3-6.

Figure 4:
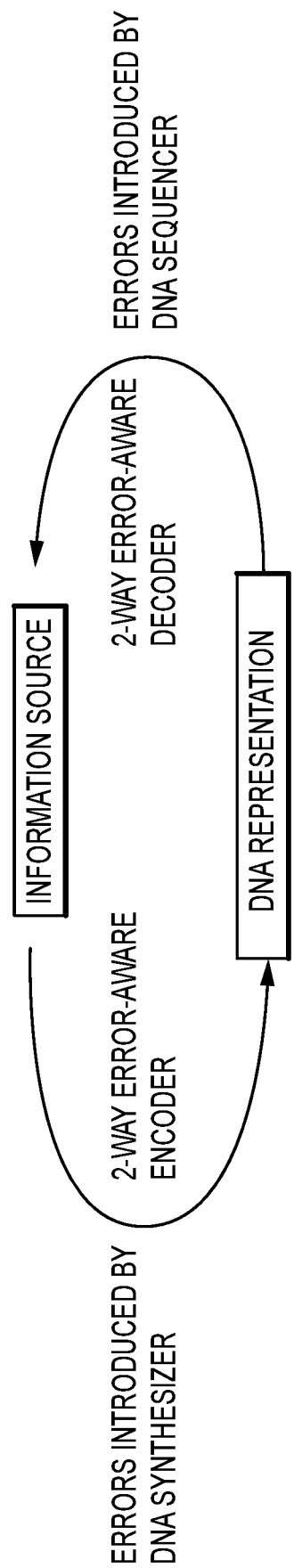
FIG. 4 illustrates an embodiment of ideal error compensation.

FIG. 4 illustrates an embodiment of ideal error compensation. Ideal error compensation is an error compensation scheme that is aware of error modes of the synthesizer and sequencer technologies. Errors are reduced and/or compensated through a combination of avoiding error generation, and detection and correction of errors using knowledge of the error modes of both the DNA reading and DNA writing systems, and also based on the observed data uncertainty, as reflected in empirical quality scores for the written and read DNA sequences, as generated by the reading and writing systems.

Figure 5:
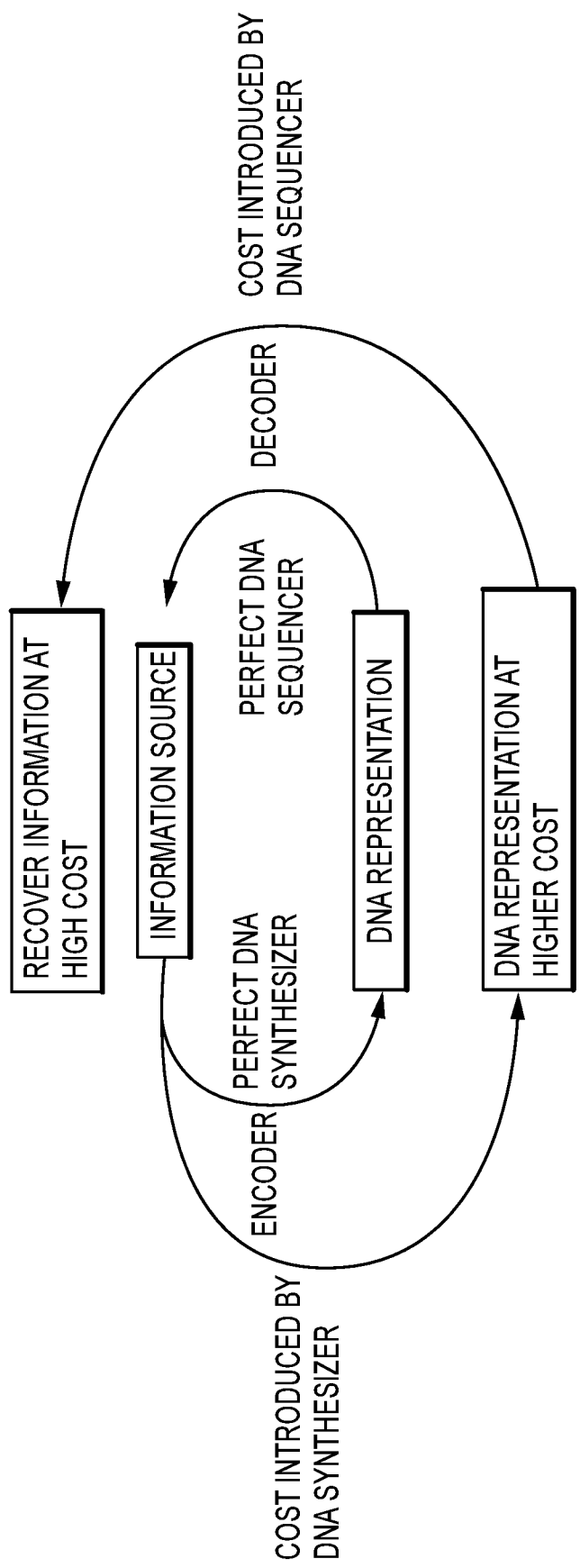
FIG. 5 illustrates cost-conscious management of errors in a DNA information storage system.

FIG. 5 illustrates cost-conscious management of the errors in a DNA information storage system. In general, certain DNA sequences can have inherently greater cost, based on a cost function related to, for example, error rate, time required, reagent consumption, financial cost, etc. In various aspects of the present disclosure, costs associated with the reading and writing technologies are considered, and are reduced or optimized be using an encoding/decoding scheme that minimizes costs in general (e.g., by avoiding high cost, error prone, slow synthesis or slow to read DNA motifs).

In various embodiments, nucleotides can be preferentially selected for incorporation in nucleotide sequences based on their ease of synthesis in the writing process that forms molecules, reduced propensity to form secondary structure in the synthesized molecules, and/or ease in reading during the data decoding process. In various aspects, bad writing motifs and bad reading motifs are avoided in the selection of nucleotides for incorporation into nucleotide sequences, with a focus on incorporating segments in the nucleotide sequence that will produce mutually distinguishable signals when that nucleotide sequence is read to decode the encoded information. For example, in reading a nucleotide sequence, A and T are mutually distinguishable, C and G are mutually distinguishable, A, C and G are mutually distinguishable, AAA and TT are mutually distinguishable, A, GG and ATA are mutually distinguishable, and C, G, AAA, TTTT, GTGTG are mutually distinguishable. These, and many other sets of nucleotide and nucleotide segments provide mutually distinguishable signals in a reader, and thus can be considered for incorporation in a nucleotide sequence when encoding a set of information into a nucleotide sequence.

Additionally, there are nucleotide segments that are difficult to write, and thus should be avoided when encoding a set of information into a nucleotide sequence. In various embodiments, encoding of a set of information into a nucleotide sequence comprises the use of one of the remaining distinguishable feature sets as the encoding symbols, such as may correspond to binary 0/1, trinary 0/1/2 or quad 0/1/2/3 code, etc., along with an error correcting encoding to define the set of information in a way that avoids the hard to read and hard to write features. In this way, overall performance of an information storage system is improved.

In various embodiments, methods of storing information in a nucleotide sequence and retrieving the stored information in the nucleotide sequence is disclosed. In various aspects, the method comprises (a) a system for synthesizing nucleotide sequences, such as synthesizing DNA molecules, corresponding to a given sequence of bases. As discussed, the given base sequence may be determined through a thoughtful selection of nucleotides and nucleotide segments that encode a given set of information, such as binary information. In various aspects, the method comprises (b) a system for reading signals from a nucleotide sequence, such as from a DNA strand, wherein the nucleotide sequence comprises a collection of distinguishable sequence segments, such that with such a set {X, Y, Z ... }, each of the sequence segments X, Y, Z ... occurring within a molecule generate distinguishable signals when processed by a reader. In other examples, the method comprises (c) identifying undesirable nucleotides and nucleotide segments based on their propensity to be written incorrectly in the synthesis process, to be incorporated too slowly in the synthesis process, to generate secondary structure in the synthesized molecule, or to be too costly to use in the synthesis process. In various embodiments, the method comprises (d) identifying undesirable nucleotide and nucleotide segments based on their propensity to be read incorrectly when information is decoded from a molecule, to read too slowly when information is decoded, and so forth. In various aspects, the method comprises utilizing a synthesis method comprising encoding a set of information into a DNA molecule, relying on an error detection and/or correcting coding scheme, and using an encoding method wherein one of the feature sets of (b) above is used as the symbol alphabet of the encoding and wherein this feature set is selected to not use any of the undesirable features delineated in (c) and (d) above, and using the reading method of (b) above to retrieve the information previously encoded in, for example, a DNA molecule.

In various embodiments, the distinguishable features in a nucleotide sequence, such as a DNA molecule, may comprise individual bases. The bad reading features may comprise individual specific bases. The bad writing features may also comprise individual specific bases, wherein the encoding scheme corresponds to using an error correcting binary code on the input information string, with binary symbols 0 and 1 converted to x and y to achieve the DNA encoding.

Figure 6:
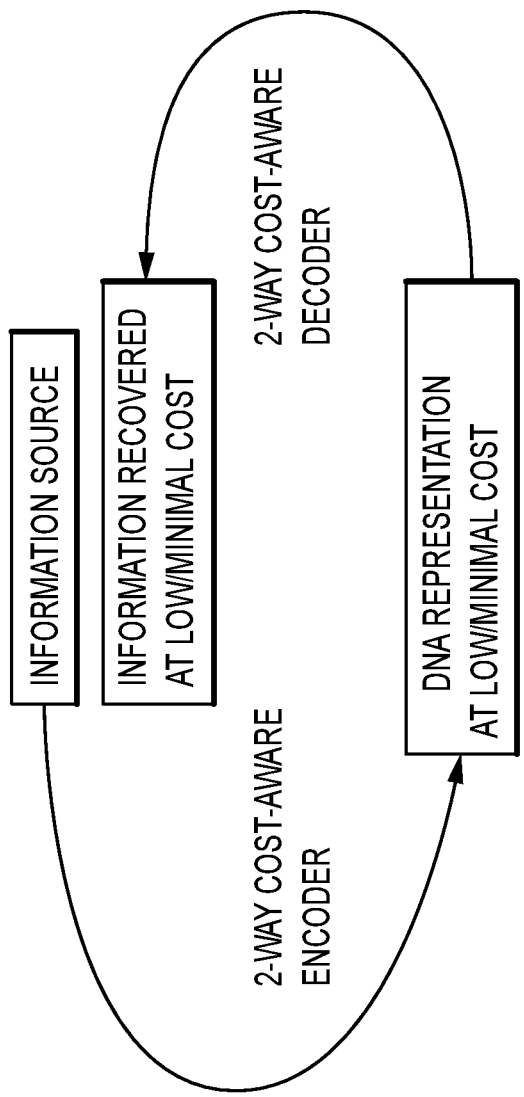
FIG. 6 illustrates an ideal error aware system.

FIG. 6 illustrates an ideal error aware system that comprises an error compensation scheme that is aware of the error modes inherent in the DNA synthesizer and sequencer technologies.

Figure 7:
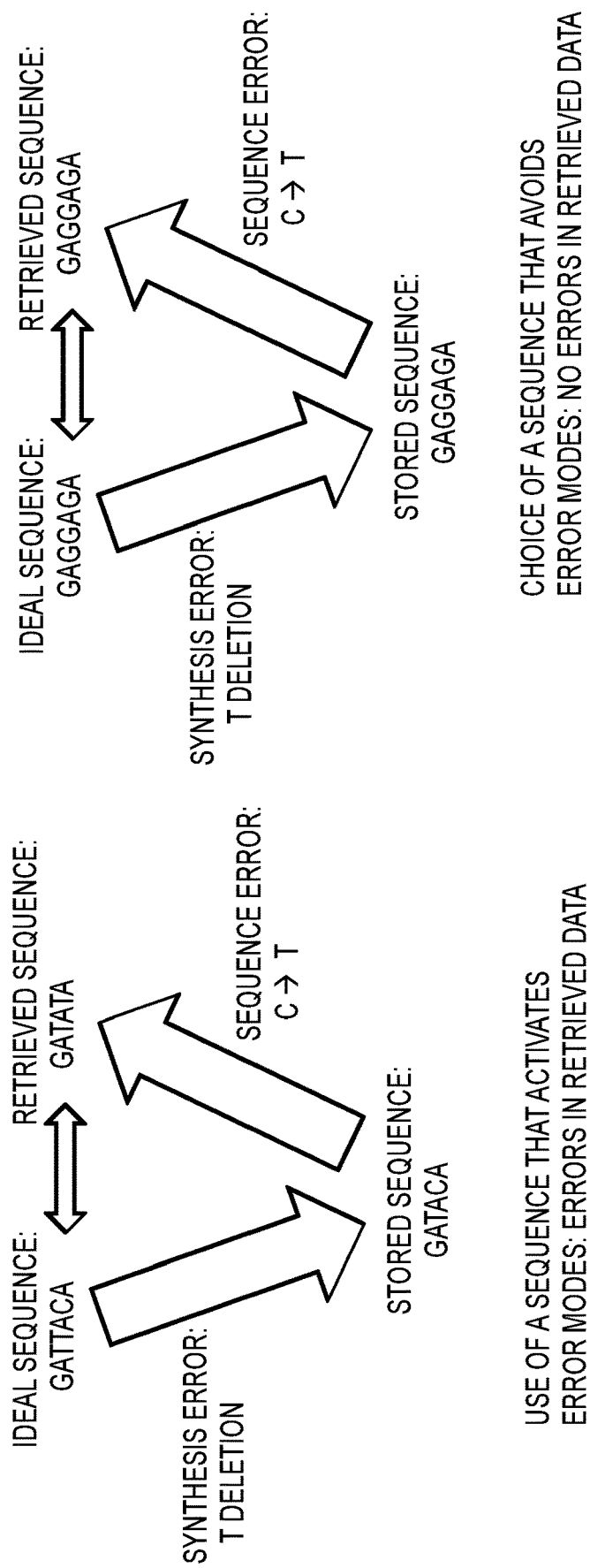
FIG. 7 illustrates an example of 2-way error compensation.

FIG. 7 illustrates an example of 2-way error compensation. The left portion of the Figure shows errors created in this specific example, and the right portion of the figure shows avoidance of these errors by an error-compensating encoding/decoding scheme that produces an input sequence that does not have the problematic DNA sequence motifs, i.e., T and C bases. In this illustrated example of FIG. 7, the DNA writer has a propensity to sometimes delete a T, and the DNA reader has a propensity to sometimes read a C as a T. In this example, use of encoding with T and C can result in errors such as an incoming encoded data sequence GATTACA reading out as GATATA, wherein one T was deleted in writing, and a C→T reading error occurred). However, if the ideal encoding of data never had a "T" or "C," e.g. in the case of encoding all binary 0/1 data simply and directly with a binary DNA code of A=0, G=1, there would be no errors produced in the storing and retrieval of data.

Thus, in general, in order to reduce errors, the digital data encoding/decoding algorithm can comprise error detecting and error correcting codes selected to minimize error production, given the actual error modes of the DNA writer and DNA reader. These codes can be devised with the benefit of prior knowledge of the error modes, i.e., the propensity for particular errors of the writer and reader.

In various embodiments, the error correcting codes reside within a single nucleotide sequence. For example, one segment of binary data is encoded in one DNA sequence, with the use of error correction and/or detection schemes on the DNA side. Such schemes may also involve encoding one segment of binary data into multiple DNA sequences, to provide another level of redundant encoding of information, which is analogous to error correction through redundant storage. Error detection schemes include, but are not limited to, repetition code, parity bits, checksums, cyclic redundancy checks, cryptographic hash functions, and error correcting codes such as hamming codes. Error correction schemes include, but are not limited to, automatic repeat request, error correcting code such as convolutional codes and block codes, hybrid automatic repeat request, and Reed-Solomon codes.

In various embodiments, a method of devising an optimal or highly efficient error correcting encoding, wherein the incoming digital data is considered as binary words of length N, comprises the steps of: providing a space of all DNA words of length M, such that there are many more possible DNA words than binary words (i.e., $4^M >> 2^N$); and selecting a subset of $2^N$ of the DNA words to use as code words for encoding the $2^N$ binary information words, such that when each of these DNA code words is expanded into the set of probable DNA writing errors for the given word, and then that set further expanded by the set of probable reading errors words, these resulting $2^N$ sets of DNA words remain disjoint with high probability. In such a case, any word read by the reader can be properly associated back to the ideal encoded DNA word with very high probability. This method constitutes a combination of error correcting and error avoiding encoding of information. In addition, the decoding algorithm would also naturally make use of confidence or odds information supplied by the reader, to select the maximum likelihood/highest confidence decoding relative the encoding scheme.

Another key aspect of optimizing the overall DNA data storage system costs is the time required to write data. For example, the critical time cost in many embodiments may be the time cost of writing the data. In various embodiments, the writing of certain slow-to-synthesize bases and sequence motifs are avoided in order to shorten the overall writing time. In other aspects, the writing is faster, such as by reducing the time spent on each chemistry cycle of some cyclical process that writes one base in many parallel synthesis reactions, with acceptance of a higher overall writing error rate.

Similarly, for reading, a faster reading process may be employed, with the trade-off being a higher rate of reading errors. In various examples, a faster reading process is employed without an increase in error by avoiding the introduction of certain types of sequences in the encoding that are difficult to read at a rapid rate, such as homopolymer runs. In either case, the information encoding/decoding algorithm can be co-optimized with these choices that allow for faster reading/writing but with extra error modes to be avoided, or avoiding slow-to-read/write sequence motifs, handled within the encoding/decoding.

Figure 8:
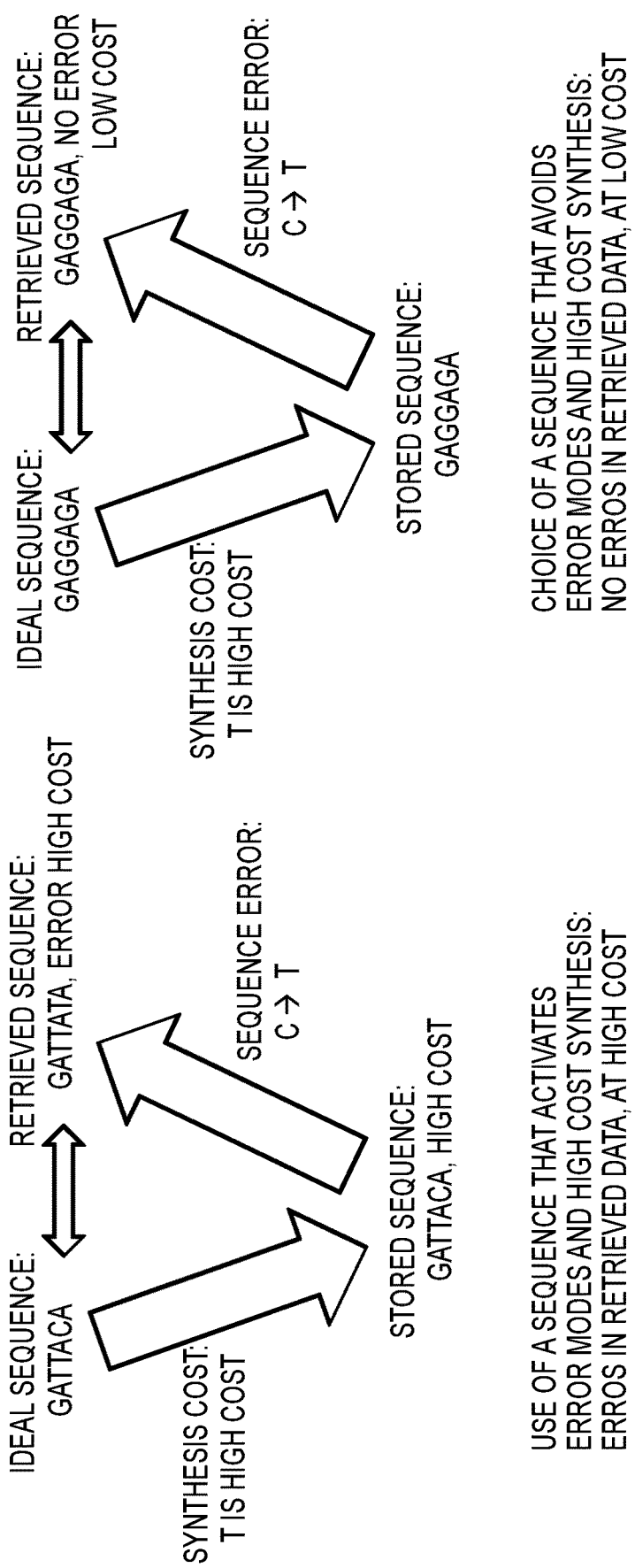
FIG. 8 illustrates an example of 2-way cost compensation for general cost reduction/optimization.
Figure 9:
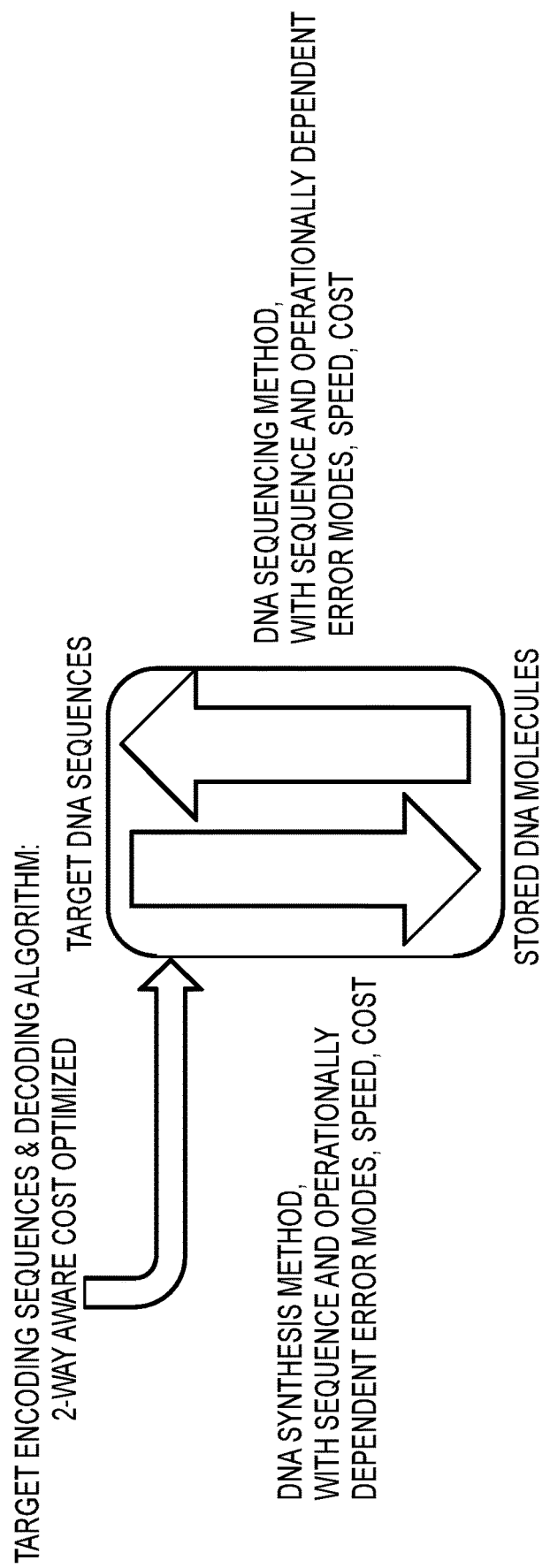
FIG. 9 illustrates exemplary factors of a cost-optimized encoding system.

These embodiments of cost optimization are illustrated in FIGS. 8 and 9. FIG. 8 illustrates an example of 2-way cost compensation for general cost reduction/optimization. In this example, there exists both a high cost synthesis, T, and an error mode whereby reading C goes to T. In the embodiment of FIG. 8, error compensation for a generalized cost-optimizing result, reducing both synthesis costs and errors, comprises the use of encoding that avoids the costly DNA motifs T, and C. FIG. 9 illustrates exemplary factors of a cost optimized encoding system. Factored in are the financial cost, speed and error rates of the DNA writer and reader when co-optimizing the encoding/decoding algorithm and the performance parameter section of the DNA reading and writing systems. The performance parameters of the writer and reader depend on the DNA sequence as well as other tunable/selectable parameters of those systems, and these parameters, as well as algorithm selection and parameters, are co-optimized to reduce or minimize these costs.

In general, there exist a variety of factors in an overall measure of "cost" of the information storage/retrieval process, including error rates, speed, financial costs of reagents or components, robustness of the system or time between failure, etc. These properties of the reader and writer are furthermore generally variable, depending on the operating parameters (e.g., time allowed for some reaction to complete, purity of chemical reagents used, operating temperature, etc.).

In various embodiments, the choice of, and control parameter settings of the encoder/decoder algorithm, and of the writer and reader systems, are co-selected and/or co-optimized, to reduce or minimize some global cost function or collection of cost functions, (see FIG. 9). In this way, the "cost" performance of the system can be greatly reduced, through avoidance or mitigation of the higher cost operating scenarios.

Optimization of the DNA Reading Device

In various embodiments of the DNA information storage system herein, the DNA reading device comprises a massively parallel DNA sequencing device, which is capable of a high speed of reading bases from each specific DNA molecule such that the overall rate of reading stored DNA information can be fast enough, and at high enough volume, for practical use in large scale archival information retrieval. The rate of reading bases sets a minimum time on data retrieval, related to the length of stored DNA molecules.

Figure 10A:
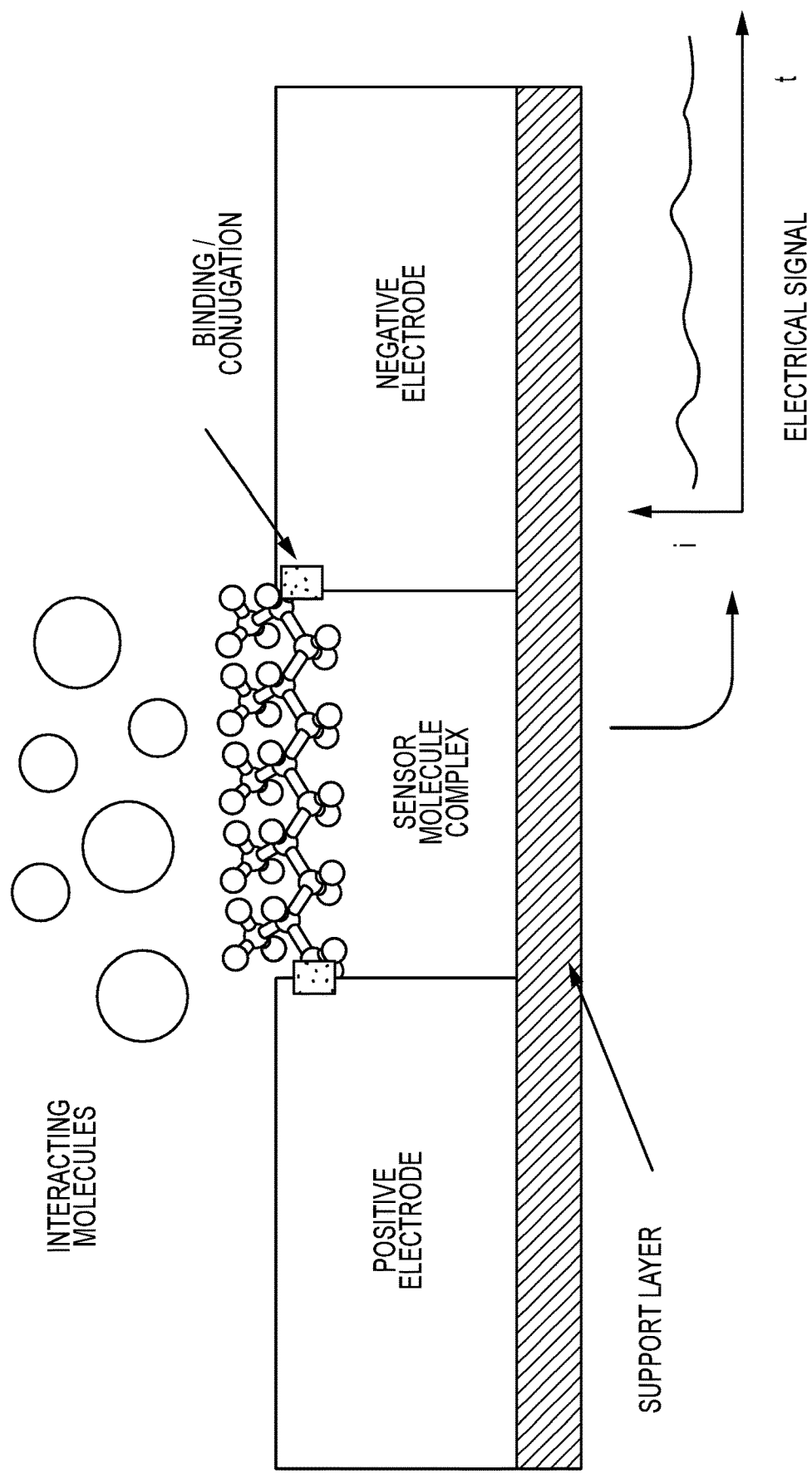
FIG. 10A illustrates the basic concept of a molecular electronic sensing circuit sensing the interaction of interacting molecules with a sensor molecule complex.

In various embodiments, a molecular electronics sensor extracts information from single DNA molecules, in a way that provides a reader for digital data stored as DNA. FIG. 10A illustrates the basic concept of a molecular electronic sensing circuit in which a sensor molecule complex completes an electrical circuit, an electrical circuit parameter, such as current "i," is measured versus time ("t") to provide a signal, wherein variations in signal correspond to interactions of the sensor molecule complex with interacting molecules in the environment of the sensor. As illustrated in FIG. 10A, a molecular electronics sensor comprises a circuit in which a single molecule, or a complex of a small number of molecules, forms a completed electrical circuit spanning the gap between a pair of nano-scale electrodes, and an electronic parameter is modulated by this single molecule or complex, and in which this parameter is measured as a signal to indicate ("sense") the single molecule or complex interacting with target molecules in the environment. In various embodiments, e.g., as indicated in FIG. 10A, the measured parameter is current passing through the electrodes, versus time, and the molecular complex is conjugated in place with specific attachment points to the electrodes.

Figure 10B:
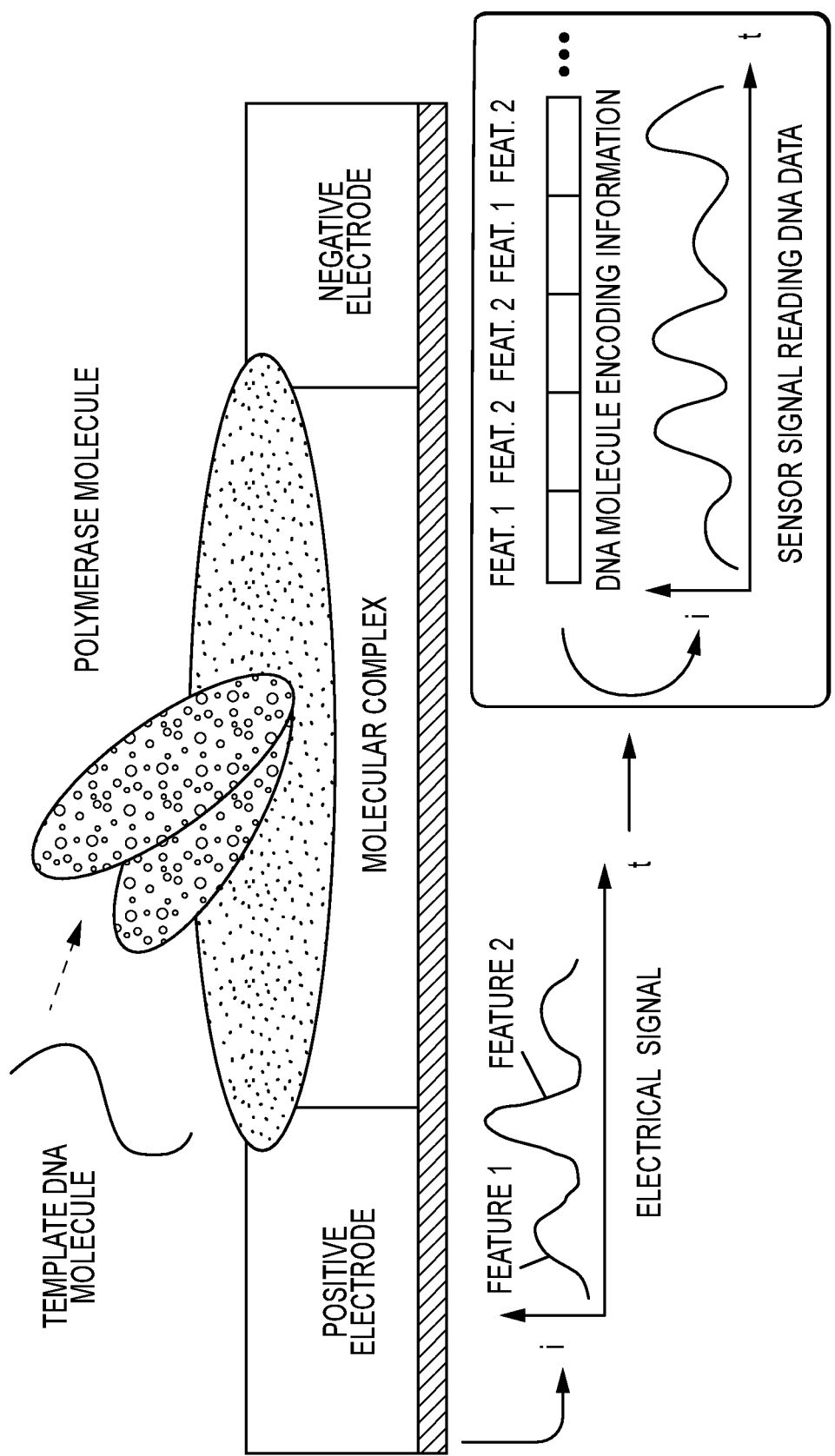
FIG. 10B illustrates an embodiment of a polymerase-based molecular sensor used as a reader for data encoded into synthetic DNA molecules.

FIG. 10B illustrates an embodiment of a polymerase-based molecular electronics sensor for use herein as a DNA reader device. A sensor, such as illustrated in FIG. 10B, and comprising a polymerase produces distinguishable signals from distinct DNA molecular features (abbreviated in the figure as "Feat. 1," "Feat. 2," and so forth). Such features can be used to encode information into synthetic DNA molecules, which can in turn be read via the sensor.

Figure 11:
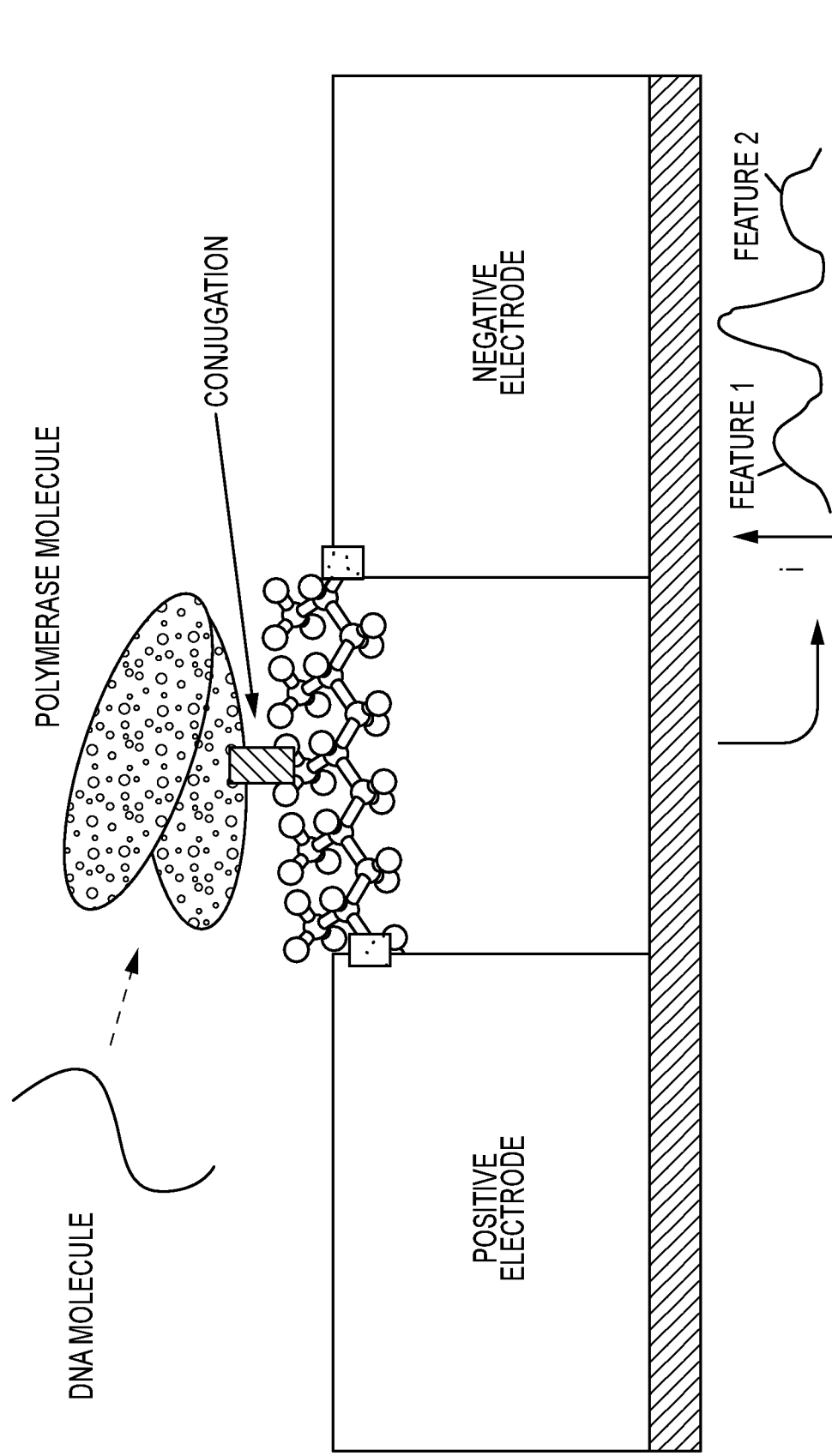
FIG. 11 illustrates an embodiment of the polymerase-based sensor of FIG. 10B, where the polymerase is conjugated to a bridging molecule spanning the electrodes.

In various embodiments, the molecular complex of an individual sensor circuit comprises a single polymerase enzyme molecule that engages with a target DNA molecule to produce electrical signals as it processes the DNA template. Under appropriate conditions, such a polymerase will produce distinguishable electrical signal features, corresponding to specific distinct features of a template DNA molecular, such as illustrated in FIG. 11 by two different peak shapes in the signal trace. Such distinguishable signal features can therefore be used to encode information in synthetic DNA molecules, through a great variety of encoding schemes, such as those of FIG. 29, discussed below, and therefore such a sensor provides the reader for data so encoded.

FIG. 11 illustrates an embodiment wherein a polymerase molecule is conjugated to a bridge molecule that completes the circuit between the two electrodes in a pair of electrodes. Current between the electrodes is the measured electrical parameter. When the polymerase engages a proper template, such as a primed, single-stranded DNA molecule, in the presence of suitable buffer solution and dNTPs, the activity of the polymerase in synthesizing a complementary strand causes perturbations in the measured signals related to the detailed kinetics of the enzyme activity. In this case, the plot of current through the electrodes versus time provides a signal with distinguishable features (such as amplitude variations) corresponding to structural features of the DNA molecule being processed.

Figure 12:
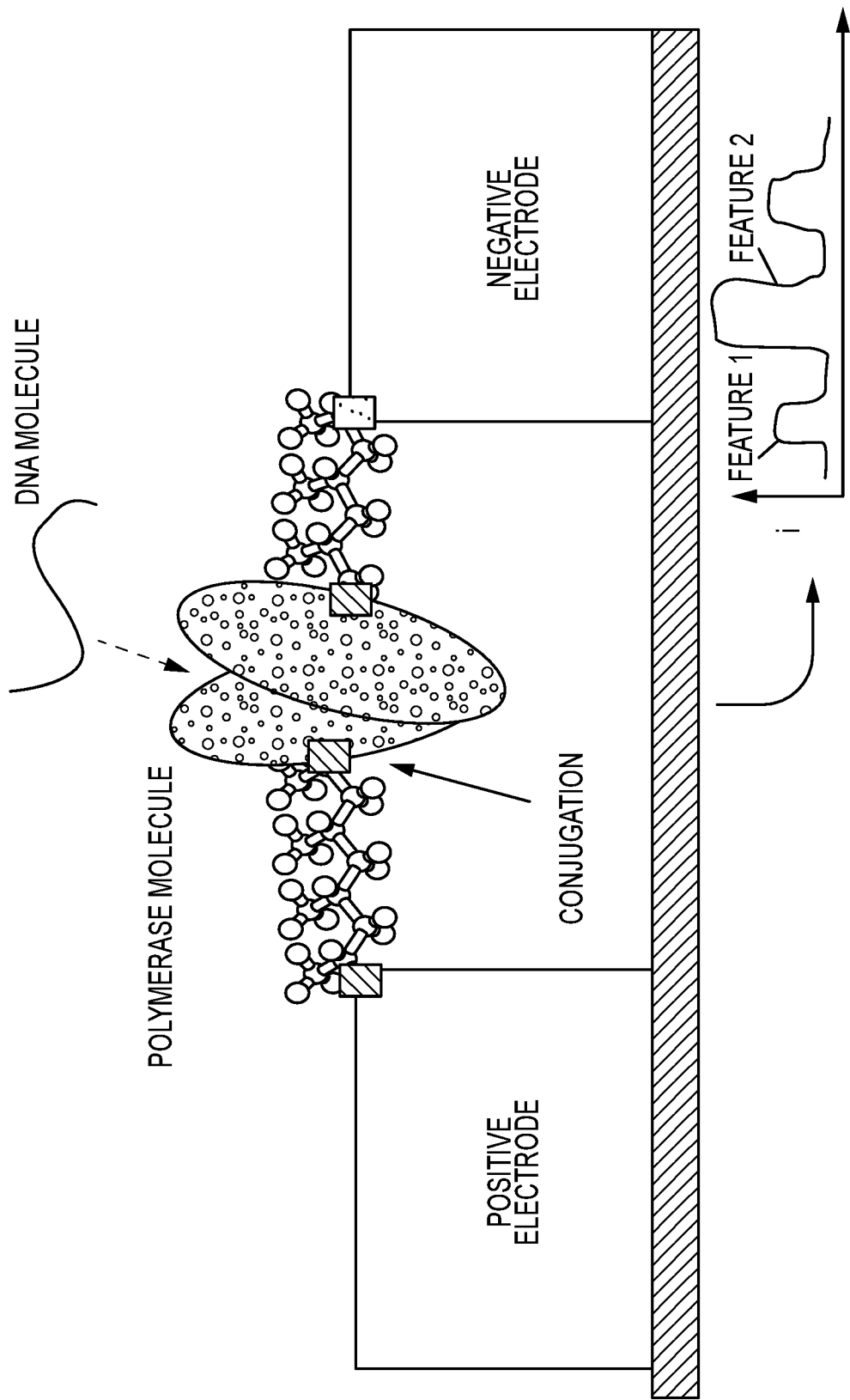
FIG. 12 illustrates an embodiment of a sensor circuit wherein the polymerase is conjugated directly in the current path, and wherein two arm molecules provide connection to the electrodes.

FIG. 12 illustrates an embodiment of a sensor circuit wherein the polymerase is wired to the electrodes in a pair of electrodes using two "arm" molecules, so as to make the polymerase an essential part of the current path.

Figure 13:
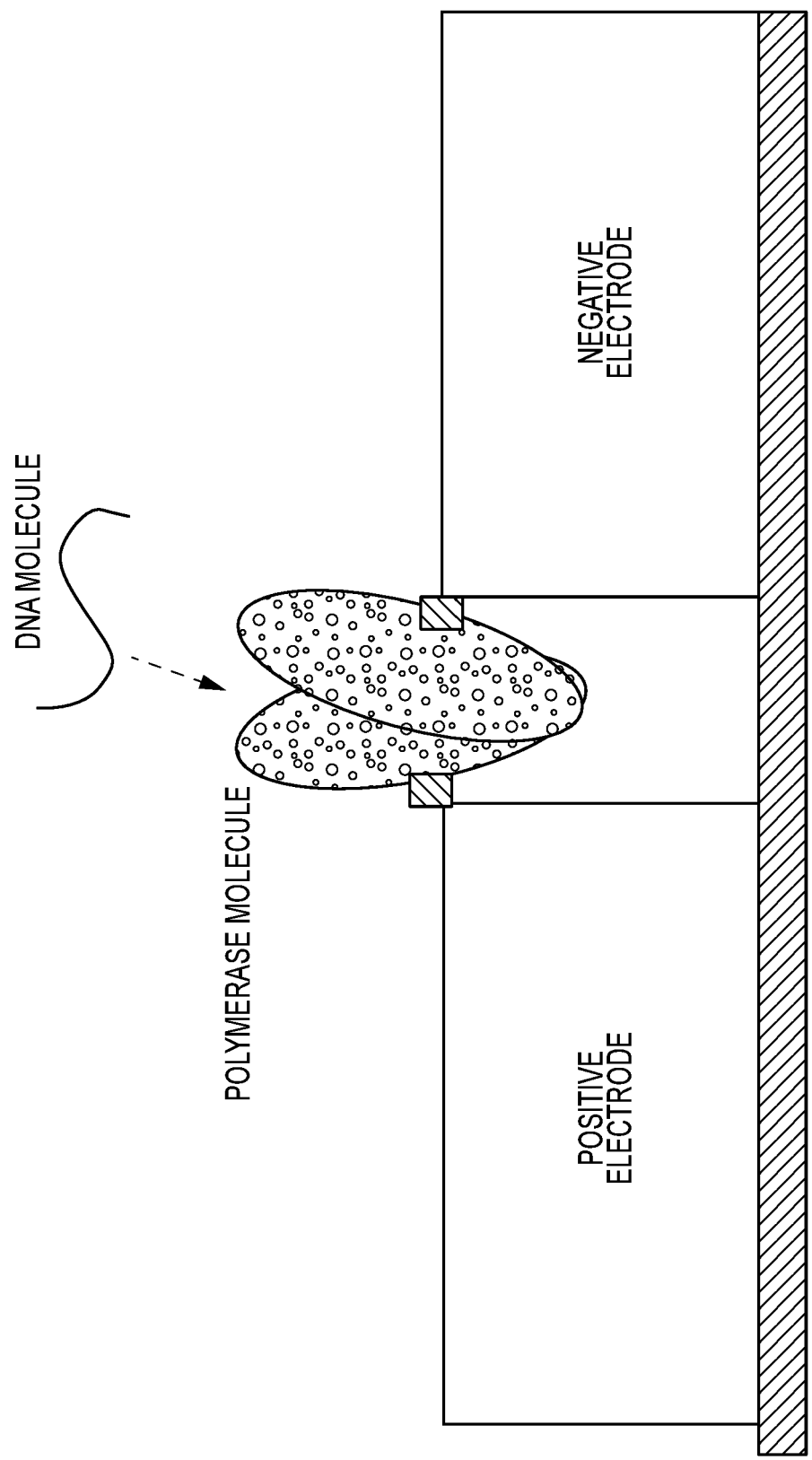
FIG. 13 illustrates an embodiment of a sensor where the polymerase is directly conjugated to the electrodes, with no arm or bridge molecules.

FIG. 13 shows another embodiment of a sensor circuit, where there are no arms, and the polymerase is conjugated directly to the two electrodes. In various embodiments, the molecular complex conjugated to the polymerase, and conjugated to the electrodes, is formed via a series of one or more molecular self-assembly processes, driven by the highly specific and efficient chemistry of various conjugation groups and conjugation reactions.

Figure 14:
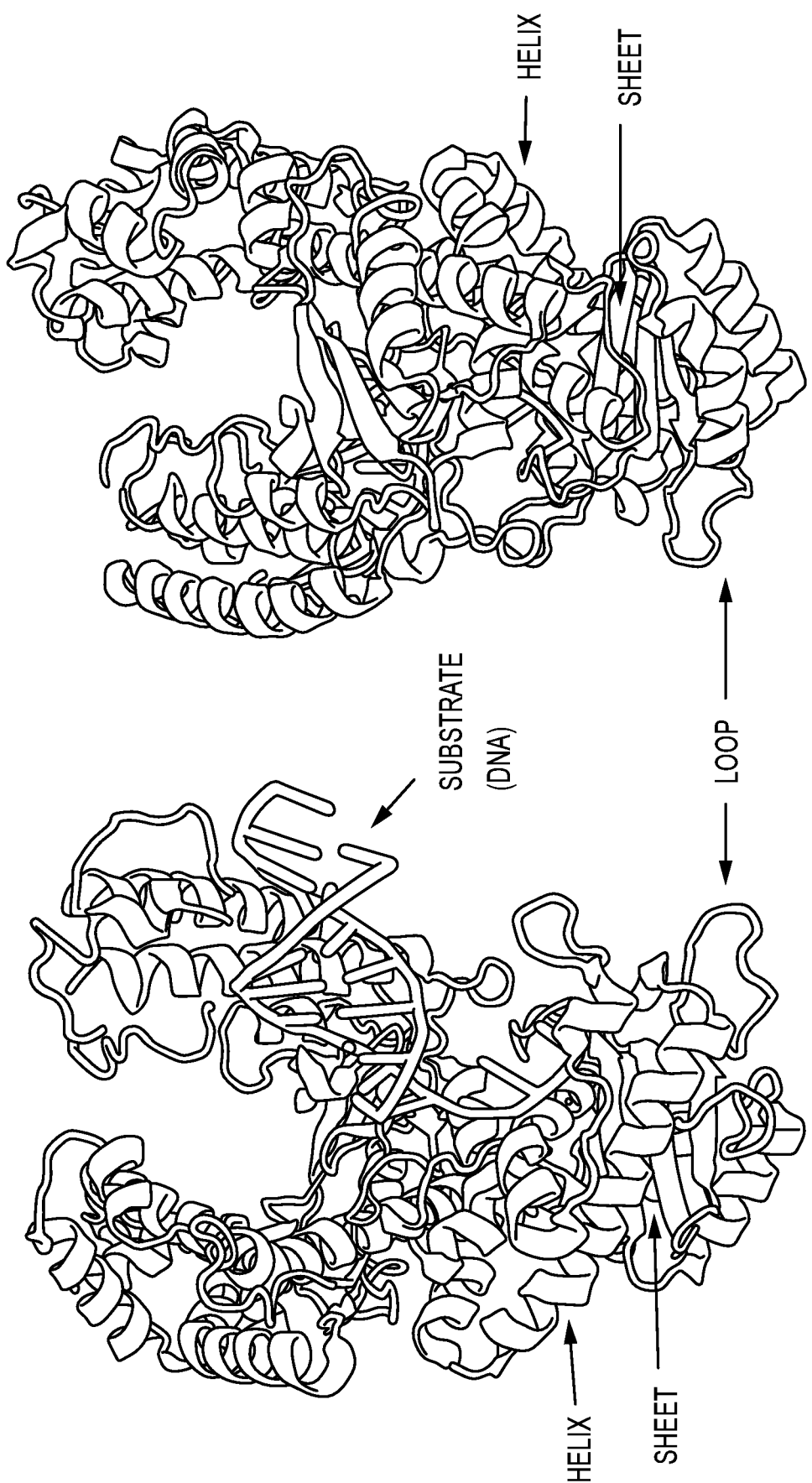
FIG. 14 shows the 3D detailed protein structure of one specific polymerase molecule, the Klenow Fragment of *E. Coli.* Polymerase I.

FIG. 14 shows 3D representations of the molecular structure of one specific polymerase, namely the Klenow (or Large) Fragment of the *E. Coli* Polymerase I.

Figure 15:
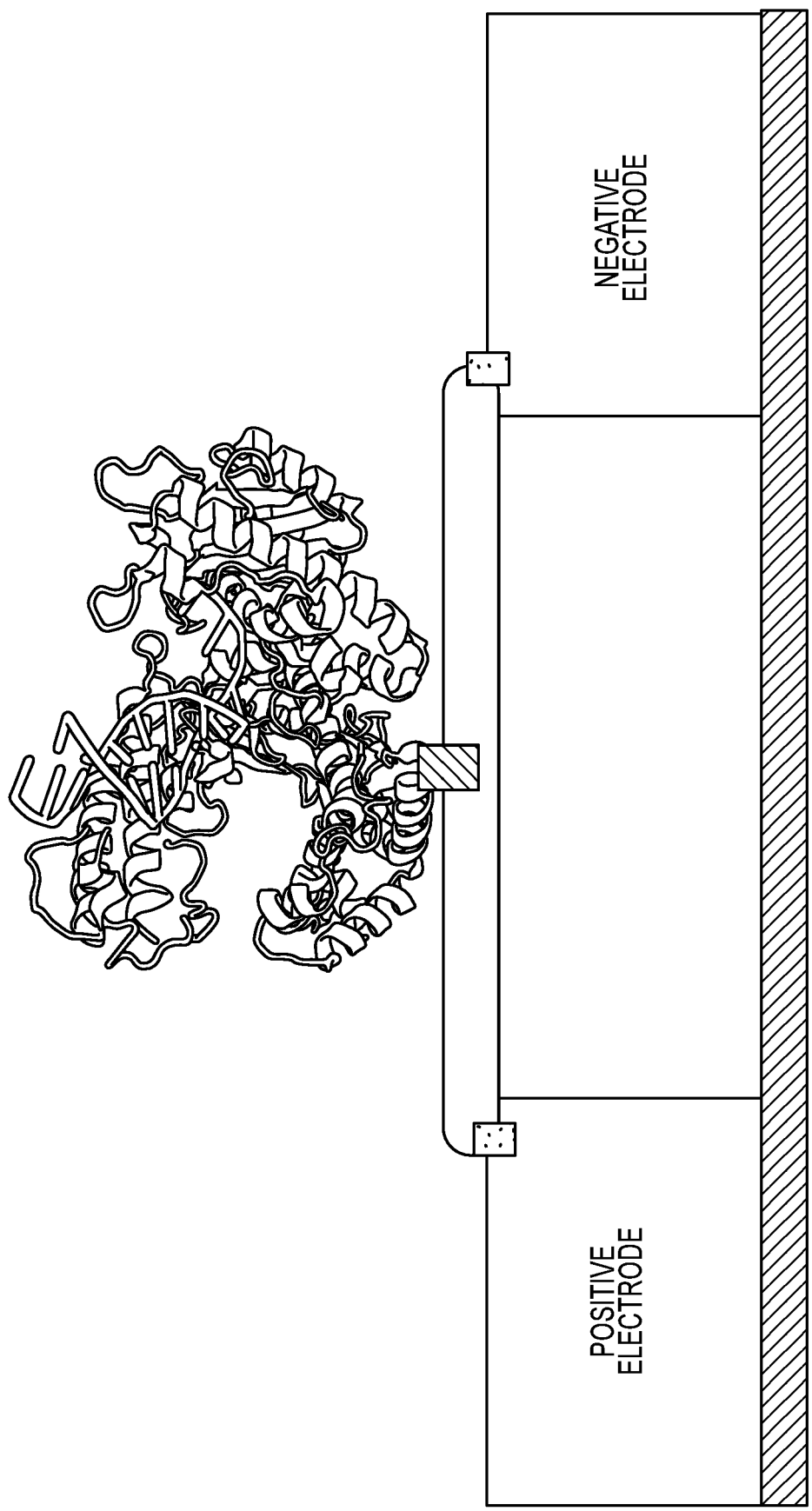
FIG. 15 illustrates an embodiment of a molecular electronic sensor wherein the Klenow Fragment of *E. Coli.* Polymerase I is conjugated to a bridge molecule that spans the gap between the electrodes.
Figure 16:
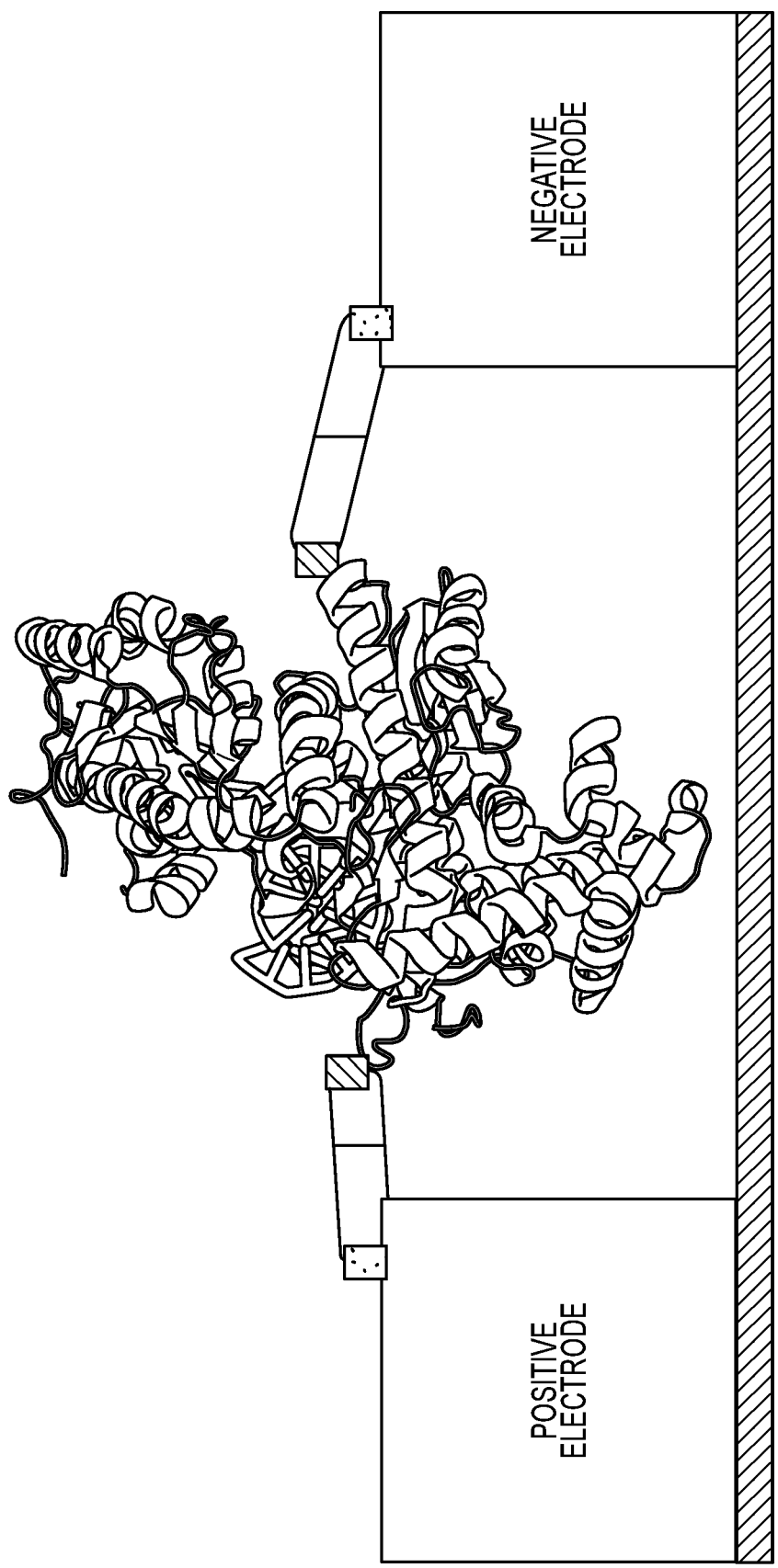
FIG. 16 illustrates an embodiment of a molecular electronic sensor where the Klenow Fragment of *E. Coli.* Polymerase I is conjugated directly into the current path through use of two arm molecules linking the polymerase to the electrodes.

FIGS. 15 and 16 illustrate embodiments of a molecular sensor circuit wherein a Klenow (or Large) Fragment of the *E. Coli* Polymerase I is conjugated to an abstract molecular bridge molecule (indicated by the bolded bar between electrodes), or conjugated directly into the circuit through use of two abstract arm molecules, respectively. FIG. 17 illustrates an embodiment of a molecular electronic sensor where the Klenow Fragment of *E. Coli* Polymerase I is conjugated directly into the current path and directly to the metal electrodes, without the use of arm or bridge molecules.

FIG. 18 illustrates an embodiment of a working sensor 200 in detail, used herein as a DNA reader device for a DNA data information system. Molecular sensor structure 200 comprises two electrodes 201 and 202, comprising titanium or chromium. Electrodes 201 and 202 may comprise the source and drain electrodes in a circuit. The electrodes 201 and 202 are separated by a nanogap of about 10 nm. Other gap distances may be required to accommodate other lengths of biomolecular bridges. In this example, the bridge molecule 203 comprises a double-stranded DNA oligomer molecule of about 20 nm in length (e.g., 60 bases; 6 helical turns), with thiol groups 204 and 205 at both the 3' and 5' ends for coupling of the bridge molecule 203 to gold contacts 206 and 207 provided on each metal electrode 201 and 202. The bonds between the ends of the DNA oligomer and the gold contact points comprise sulfur-gold bonds, available from thiol groups on 5' ends of the DNA bridge molecule binding to the gold. The probe molecule in this sensor comprises Klenow Fragment of *E. Coli* Polymerase I molecule 210, chemically crosslinked at covalent linkage 211 to a Streptavidin protein 212, using a biotinylated site on the polymerase, which in turn is coupled to a binding site 214 via a biotinylated nucleotide in the synthetic DNA oligo 203. In operation, the sensor 200 further comprises a DNA strand 220 being processed by the polymerase 210. The figure approximates the relative sizes of the molecules and atoms.

In various embodiments of a molecular electronics sensor for use herein, the polymerase may be a native or mutant form of Klenow, Taq, Bst, Phi29 or T7, or may be a reverse transcriptase. In various embodiments, the mutated polymerase forms will enable site specific conjugation of the polymerase to the bridge molecule, arm molecule or electrodes, through introduction of specific conjugation sites in the polymerase. Such conjugation sites engineered into the protein by recombinant methods or methods of synthetic biology may, in various embodiments, comprise a cysteine, an aldehyde tag site (e.g. the peptide motif CxPxR), a tetracysteine motif (e.g., the peptide motif CCPGCC) (SEQ ID NO: 1), or an unnatural or non-standard amino acid (NSAA) site, such as through the use of an expanded genetic code to introduce a p-acetylphenylalanine, or an unnatural cross-linkable amino acid, such as through use of RNA- or DNA-protein cross-link using 5-bromouridine, (see, e.g., Gott, J. M., et al., Biochemistry, 30 (25), pp 6290-6295 (1991)).

The bridge molecules or arm molecules may, in various embodiments, comprise double stranded DNA, other DNA duplex structures, such as DNA-PNA or DNA-LNA or DNA-RNA duplex hybrids, peptides, protein alpha-helix structures, antibodies or antibody Fab domains, graphene nanoribbons or carbon nanotubes, or any other of a wide array of molecular wires or conducting molecules known to those skilled in the art of molecular electronics. The conjugations of polymerase to such molecules, or of such molecules to the electrodes, may be by a diverse array of conjugation methods known to those skilled in the art of conjugation chemistry, such as biotin-avidin couplings, thiol-gold couplings, cysteine-maleimide couplings, gold or material binding peptides, click chemistry coupling, Spy-SpyCatcher protein interaction coupling, antibody-antigen binding (such as the FLAG peptide tag/anti-FLAG antibody system), and the like. Coupling to electrodes may be through material binding peptides, or through the use of a SAM (Self-Assembling-Monolayer) or other surface derivatization on the electrode surface to present suitable functional groups for conjugation, such as azide or amine groups. The electrodes comprise electrically conducting structures, which may comprise any metal, such as gold, silver, platinum, palladium, aluminum, chromium, or titanium, layers of such metals in any combination, such as gold on chromium, or semiconductors, such as doped silicon, or in other embodiments, a contact point of a first material on a support comprising a second material, such that the contact point is a site that directs chemical self-assembly of the molecular complex to the electrode.

In various embodiments, electrical parameters measured in a sensor, such as the sensor illustrated in FIG. 18, can in general be any electrical property of the sensor circuit measurable while the sensor is active. In one embodiment, the parameter is the current passing between the electrodes versus time, either continuously or sampled at discrete times, when a voltage, fixed or varying, is applied between the electrodes. In various embodiments, a gate electrode is capacitively coupled to the molecular structure, such as a buried gate or back gate, which applies a gate voltage, fixed or variable, during the measurement. In various other embodiments the measured parameter may be the resistance, conductance, or impedance between the two electrodes, measured continuously versus time or sampled periodically. In various aspects, the measured parameter comprises the voltage between the electrodes. If there is a gate electrode, the measured parameter can be the gate voltage.

In various embodiments, the measured parameter in a molecular electronics sensor, such as the sensor of FIG. 18, may comprise a capacitance, or the amount of charge or voltage accumulated on a capacitor coupled to the circuit. The measurement can be a voltage spectroscopy measurement, such that the measurement process comprising capturing an I-V or C-V curve. The measurement can be a frequency response measurement. In all such measurements, for all such measured parameters, there are embodiments in which a gate electrode applies a gate voltage, fixed or variable, near the molecular complex during the measurement. Such a gate will typically be physically located within a micron distance, and in various embodiments, within a 200 nm distance of the molecular complex. For the electrical measurements, in some embodiments there will be a reference electrode present, such as a Ag/AgCl reference electrode, or a platinum electrode, in the solution in contact with the sensor, and maintained at an external potential, such as ground, to maintain the solution at a stable or observed potential, and thereby make the electrical measurements better defined or controlled. In addition, when making the electrical parameter measurement, various other electrical parameters may be held fixed at prescribed values, or varied in a prescribed pattern, such as, for example, the source-drain electrode voltage, the gate voltage if there is a gate electrode, or the source-drain current.

The use of a sensor, such as the sensor illustrated in FIG. 18, to measure distinguishable features of a DNA molecule requires the polymerase to be maintained in appropriate physical and chemical conditions for the polymerase to be active, to process DNA templates, and to produce strong, distinguishable signals above any background noise (i.e., high signal-to-noise ratio, or "SNR"). To achieve this, the polymerase may reside in an aqueous buffer solution. In various embodiments, a buffer solution may comprise any combination of salts, e.g. Nalco or KCl, pH buffers, Tris-HCl, multivalent cation cofactors, Mg, Mn, Ca, Co, Zn, Ni, Fe or Cu, or other ions, surfactants, such as Tween, chelating agents such as EDTA, reducing agents such as DTT or TCEP, solvents, such as betaine or DMSO, volume concentrating agents, such as PEG, and any other component typical of the buffers used for polymerase enzymes in molecular biology applications and known to those skilled in the field of molecular biology. The sensor signals may also be enhanced by such buffers being maintained in a certain range of pH or temperature, or at a certain ionic strength. In various embodiments, the ionic strength may be selected to obtain a Debye length (electrical charge screening distance) in the solution favorable for electrical signal production, which may be, for example, in the range of from about 0.3 nm to about 100 nm, and in certain embodiments, in the range of from about 1 nm to about 10 nm. Such buffers formulated to have larger Debye lengths may be more dilute or have lower ionic strength by a factor of 10, 100, 1000, 100,000 or 1 million relative to the buffer concentrations routinely used in standard molecular biology procedures such as PCR. Buffer compositions, concentrations and conditions (pH, temperature, or ionic strength, for example) may also be also selected or optimized to alter the enzyme kinetics to favorably increase the signal-to-noise ratio (SNR) of the sensor, the overall rate of signal production, or overall rate of information production, in the context of reading data stored in DNA molecules. This may include slowing down or speeding up the polymerase activity by these methods, or altering the fidelity or accuracy of the polymerase. This optimal buffer selection process consists of selecting trial conditions from the matrix of all such parameter variations, empirically measuring a figure of merit, such as related to the discrimination of the distinguishable features, or to the over speed of feature discrimination when processing a template, and using various search strategies, such as those applied in statistical Design Of Experiment (DOE) methods, to infer optimal parameter combinations.

The use of a sensor such as the sensor of FIG. 18 to measure distinguishable features of a DNA molecule requires the polymerase be provided with a supply of dNTPs so that the polymerase can act processively on a template single-stranded DNA molecule to synthesize a complementary strand. The standard or native dNTPs are dATP, dCTP, dGTP, and dTTP, which provide the A, C, G, and T base monomers for polymerization into a DNA strand, in the form required for the enzyme to act on them as substrates. Polymerase enzymes, native or mutant, may also accept analogues of these natural dNTPs, or modified forms, that may enhance or enable the generation of the distinguishable signals.

In various aspects of DNA reading herein, if a system reads a DNA molecule at a speed of 1 base per 10 minutes, as is representative of current next generation, optical dye-labeled terminator sequencers, then reading a 300 base DNA molecule takes at least 3,000 minutes (50 hours), aside from any time required to prepare the sample for reading. Such relatively slower systems therefore favor storing information in a larger number of shorter reads, such as 30 base reads that could be read in 5 hours. However, this requires a larger number of total reads, so the system must support billions or more such reads, as it the case on such sequencers. The current generation of optical massively parallel sequencers, read on the order of 3 billion letters of DNA per 6-minute cycle, or roughly the equivalent of 1 billion bits per minute, or 2 MB per second, although for data stored as 100 base DNA words, this would also require 600 minutes (5 hours). This can be seen to be a relatively low rate of data reading, although within a practical realm, as a typical book may contain 1 MB of textual data. The overall rate is practical, but the slow per base time makes this highly inefficient for reading a single book of data, and ideally matched to bulk reading of 36,000 books in parallel, over 5 hours. Thus, there is also a lack of scalability in this current capability, and also a high capital cost of the reading device (optical DNA sequencers cost in the $100,000 to $1,000,000 range presently). More critically, on such current systems, the cost of sequencing a human genome worth of DNA, 100 billion bases, is roughly $1,000, which means the cost of reading information is $1,000 per 200 Giga-bits, or $40 per GB. This is radically higher than the cost of reading information from magnetic tape storage or CDs, which is on the order of $1 per 10,000 GB, or $0.0001 per GB, 400,000 fold less costly. Thus the cost of reading DNA should be reduced by several orders of magnitude, even by 1,000,000 fold, to make this attractive for large scale, long term archival storage, not considering other advantages. Such improvements may indeed be possible, as evidenced by the million-fold reduction in costs of sequencing that has already occurred since the first commercial sequencers were produced.

In various embodiment, the DNA reader of the present system comprises substantially lower instrument capital costs, and higher per-base reading speed, and greater scalability in total number of reads per run, compared to currently available optical next generation sequencing instruments. In various aspects, the reading device for use herein is based on a CMOS chip sensor array device in order to increase the speed and scalability and decrease the capital costs. An embodiment of such a device comprises a CMOS sensor array device, wherein each sensor pixel contains a molecular electronic sensor capable of reading a single molecule of DNA without any molecular amplification or copying, such as PCR, required. In various embodiments, the CMOS chip comprises a scalable pixel array, with each pixel containing a molecular electronic sensor, and such a sensor comprising a bridge molecule and polymerase enzyme, configured so as to produce sequence-related modulations of the electrical current (or related electrical parameters such as voltage, conductance, etc.) as the enzyme processes the DNA template molecule.

An exemplary molecular sensor and chip combination usable as a DNA reader device in the present DNA data storage system is depicted in FIGS. 18, 19, 30A, 30B, and 31-33. As discussed, FIG. 18 illustrates an exemplary molecular sensor comprising a bridge and probe molecule structure further comprising a bridge of double stranded DNA having about a 20 nm length (~60 bases), with thiol groups at both 5' ends for coupling to gold contacts on a metal electrode. The embodiment of FIG. 18 comprises a polymerase enzyme coupled to a molecular wire comprised of DNA, which plugs into a nano-electrode pair to form a sensor capable of producing sequence-related signals as the polymerase enzyme processes a primed DNA template.

Figure 19:
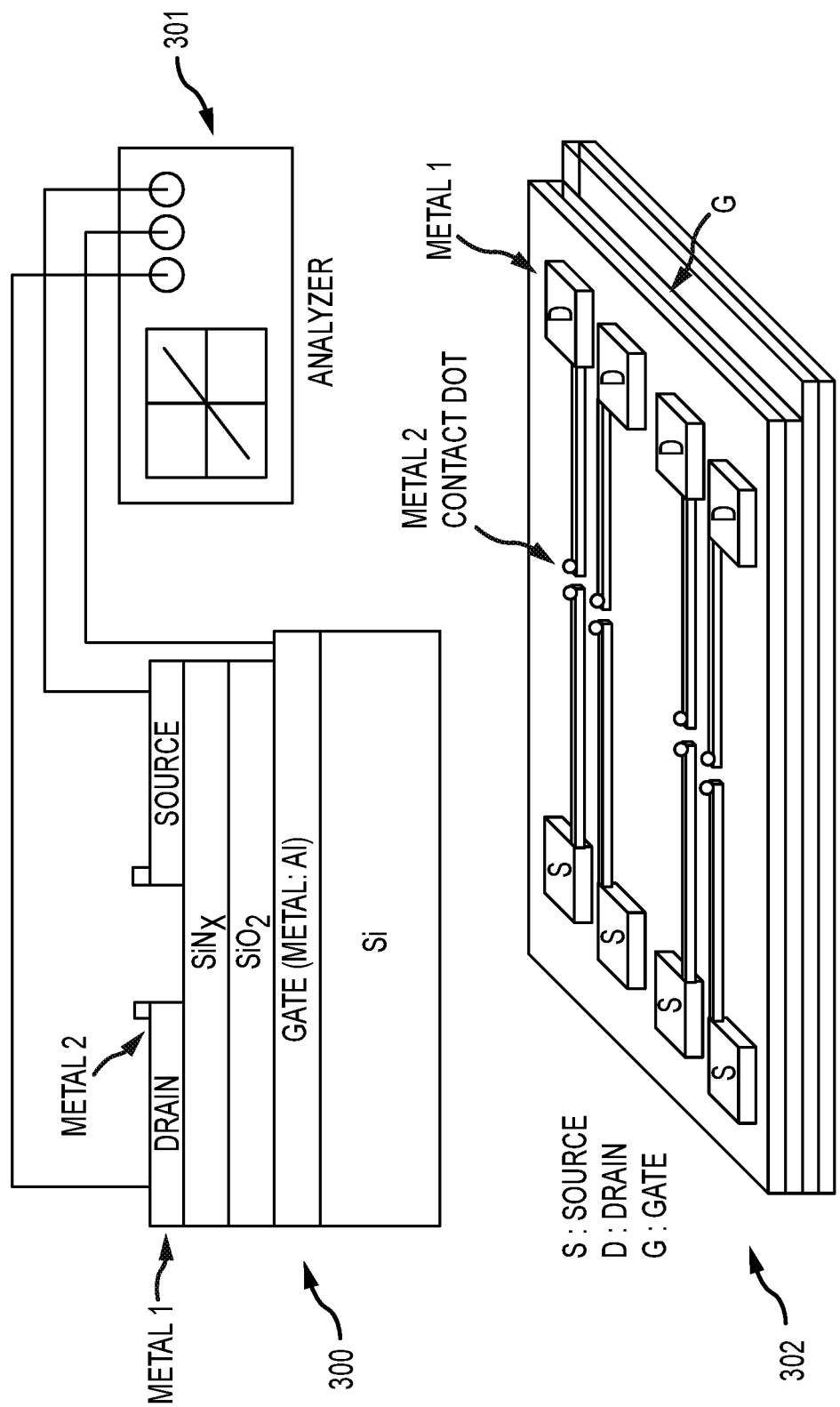
FIG. 19 illustrates a schematic of a test set-up for electrical measurements on molecular sensors for DNA sequence comprising a molecular sensor post-processed onto the pixels of a CMOS pixel array.

As illustrated in FIG. 19, such a nano-sensor can be placed by post-processing onto the pixels of a CMOS sensor pixel array, which further comprises all the supporting measurement, readout and control circuitry needed to produce these signals from a large number of sensors operating in parallel. FIG. 19 illustrates an embodiment of various electrical components and connections in molecular sensors. In the upper portion of the figure, a cross-section of an electrode-substrate structure 300 is illustrated, with attachment to an analyzer 301 for applying voltages and measuring currents through the bridge molecule of the sensor. In the lower portion of the figure, a perspective view of electrode array 302 is illustrated, usable for bridging circuits. Each pair of electrodes comprises a first metal (e.g., "Metal-1"), and a contact dot or island of a second metal (e.g., "Metal-2") at each electrode end near the gap separating the electrodes. In various examples, Metal-1 and Metal-2 may comprise the same metal or different metals. In other aspects, the contact dots are gold (Au) islands atop metal electrodes comprising a different metal. In various experiments, contact dots comprise gold (Au) beads or gold (Au)-coated electrode tips that support self-assembly of a single bridge molecule over each gap between electrode pairs, such as via thiol-gold binding.

FIG. 20 shows electron micrograph (EM) images of electrodes comprising gold metal dot contacts for bridge binding in DNA sensors. In this example, electrodes are on a silicon substrate, and were produced via e-beam lithography. To the left portion of FIG. 20 is shown an array of titanium electrodes with gold dot contacts. In the middle of FIG. 20, a close-up EM shows an electrode gap of about 7 nm with gold dot contacts and with about a 15 nm gold-togold spacing. At the right of FIG. 20, a close-up EM shows gold dots of approximately 10 nm in size positioned at the tips of the electrodes.

FIG. 21 sets forth current versus time plots obtained by measuring DNA incorporation signals with the sensor of FIG. 18. The plots show the current signals resulting from the sensor being supplied with various primed, single stranded DNA sequencing templates and dNTPs for incorporation and polymerization. In each case, the major signal spikes represent signals from discrete incorporation events, wherein the polymerase enzyme adds another base to the extending strand. At the upper left of FIG. 21, the template is 20 T bases; at the upper right, the template is 20 G bases; at the lower left, the template is 20 A bases; and at the lower right, the template is 20 C bases. The approximate rate of incorporation observed is about 10-20 bases per second, consistent with standard enzyme kinetics except for the lower rate of ~1 base per second due to rate limiting factors (e.g., lower dNTP concentration).

FIG. 22 illustrates the principle of using modified forms of dNTPs to produce distinguishable signals, showing an example wherein all 4 dNTPs carry distinct modifications that result in 4 distinguishable signals from the four bases of the template DNA. Many such modified forms are well known to those skilled in the field of nucleic acid biochemistry, and all such forms may be enabling for signal production in various embodiments. This includes dNTPs that have modification to the base, the sugar, or the phosphate group. For example, common modified forms of dNTPs include deaza-, thio-, bromo- and iodo-modifications at various sites on the molecule, or the inclusion of metal ions or different isotopes at various sites, the inclusion of diverse dye molecules at various sites, or methylation of various sites, or biotinylation of various sites. Various modifications include forms that have an extended phosphate chain, beyond the native tri-phosphate, to lengths such as tetra-, penta-, hexa-, hepta- or more (4 or more, up to 11 or more) phosphates. Other examples of modification comprise a chemical group added to the terminal phosphate of the phosphate chain, or any of the phosphates which are cleaved off during incorporation (all but the alpha-phosphate or first in the chain). Polymerases are highly tolerant of such groups, and retain a high level of activity in their presence. Thus, such groups provide a great capacity for modified dNTPs that aid in forming distinguishable signals. In various embodiments, such groups may have different charge states, or different sizes, or different degrees of hydrophobicity, which may aid in producing different signals, or such added groups may interact selectively with the sites on the bridge molecule or on the polymerase or the template DNA to produce distinguishable signals. FIG. 22 illustrates the addition of such groups onto the phosphate chain, to produce distinguishable signals of incorporation for the four bases of the template.

FIG. 23 illustrates the use of two distinct modified dNTPs, a modified dATP, indicated as A*, and a modified dCTP, indicted as C*, to provide two distinguishable signals resulting from their incorporation against the respective complementary standard bases T and G of the template DNA. The use of the two modified dNTPs provides a method to encode binary bits 0/1 into the template DNA. Thus the T and G features of the DNA template produce distinguishable signals, and can be used to encode information readable by this sensor.

FIG. 24 illustrates the use of two different sequence motifs, here homopolymers AA and CCC, to produce two distinguishable signals, which provides a means to encode binary bits 0/1 into the template DNA. In this case, AA and CCC provide two distinguishable sequence motifs that can be used for information encoding and recovery. Thus, useful information encoding and reading is possible even without single base resolution of DNA sequences, by instead relying on distinguishable sequence motifs.

FIG. 25 shows experimental data obtained from the sensor of FIG. 18 in which specific sequence motifs produced signals that are usable to encode 0/1 binary data. The sensor of FIG. 18 comprises the Klenow polymerase conjugated to a DNA bridge, which produces distinguishable signals from the encoding DNA sequence motifs 20A, 3C and 30A in the experimental template DNA. Such signals were produced by using the sensor of FIG. 18 in conjunction with a standard 1× Klenow buffer and relatively high concentration of dTTP, (10 µM), and 100 times lower concentration of the other dNTPs. The lower concentration of the other dNTPs, notably the low dGTP concentration, facilitates the distinguishable signal from the CCC region via the concentration-limited rate of incorporation. The result is that the poly-A tract has a high spike signal feature, and the poly-C tract has a low trough signal feature, which are readily distinguishable. The peaks and trough are usable to encode 0/1 binary data in the simple manner illustrated, with 0 encoded by the poly-A tract and read from the high peak signals having several seconds duration, and 1 encoded by the CCC tract and read from the low trough features having several seconds duration.

FIG. 26A illustrates an embodiment of binary encoding wherein two different sequence motifs, GATT and ACA, produce two distinguishable signals that provide a method to encode binary bits 0/1 into the template DNA.

FIG. 26B illustrates another embodiment of binary encoding wherein three different sequence motifs, GATT, ACA and AGG, produce three distinguishable signals that provide a method to encode digital data with a three-state encoding.

The use of the sensors of the present disclosure to measure distinguishable features of a DNA molecule requires the polymerase be provided with primed, single-stranded template DNA molecules as a substrate for polymerization of a complementary strand, in the course of generating the associated signals. In the context of encoding information in synthetic DNA molecules, these template molecules may be wholly chemically synthetic, and can therefore be provided with chemical or structural modifications or properties beyond those of native DNA, which may be used to enable or enhance the production of distinguishable signals for various embodiments. The polymerase, native or an engineered mutant, can accept as a substrate a great many such modified or analogue forms of DNA, many of which are well known to those skilled in the field of molecular biology. The use of such modifications to the template DNA can be used to create features with distinguishable signals. FIG. 26C shows a case where the template DNA is synthesized from two base analogues, X and Y, analogs of A and C. The dNTPs provided are the standard dATP and dCTP, which produce enhanced, distinguishable signals when incorporated against the modified bases X and Y in the template. Thus the DNA template synthesized using X and Y analogs can be used to encode information that can be read with this sensor. FIG. 26D shows a further extension of this, wherein the encoding DNA is synthesized with 8 different bases and base analogues, namely the four standard bases A, C, G, T, and the modified base analogs of these, X, Y, Z, W, respectively, to produce 8 distinguishable signals when the standard dNTPs incorporate against them in complementary fashion. Thus, template DNA synthesized from these 8 bases and analogs, A, C, G, T, X, Y, Z, W, provide 8 distinguishable signals, and thus can be used for 8 state encoding (such as shown in FIG. 29, scheme BES5).

In various embodiments, the DNA supplied to the polymerase as a template comprises some form of primed (double stranded/single stranded transition) site to act as an initiation site for the polymerase. For the purpose of storing digital data in DNA, in various embodiments, this priming will be pre-assembled into the encoding molecule, so that no further sample preparation is needed to prime the DNA template molecules. FIGS. 27A and 27B show embodiments wherein DNA data storage molecules have a universal priming structure, pre-assembled.

FIG. 27A sets forth four embodiments of primer configuration usable for storage templates. These include, in descending order in the illustration: (1) primed strand, with oligo primer hybridized to the template; (2) primer cross-linked to the strand for stability; (3) hairpin primer, with a hairpin bend of DNA or other linker molecule, such as PEG polymer linker; and (4) hairpin primer cross-liked in place. FIG. 27B sets forth embodiments of strand architecture that enable the polymerase-based sensor to interrogate the same data payload multiple times. Further considerations of these four embodiments are detailed herein.

In various embodiments, primer constructs comprise any of:

(1) a pre-hybridized universal primer oligo, e.g., of native DNA, optionally having a high melting point or high GC content, or a more stably hybridizing form such as PNA or LNA;

(2) a primer oligo modified with additional cross-linked bases (e.g., bromodeoxyuridine), covalently bound or otherwise strongly chemically coupled in place, so that there is greatly reduced chance of the primer not being in place;

(3) a hairpin primer as part of the DNA template, so that the molecule is preferentially self-priming, wherein the hairpin primer may either be composed entirely of DNA, or a hairpin loop (which in various examples is DNA, or an alternative flexible molecule such as a PEG polymer strand or multi-carbon linker, such as a C3, C6, or longer linker) that allows a hairpin bend, attached to a hybridizing oligo portion, which can be DNA, e.g., having a high melting point or high GC content, or a more stably hybridizing analog such as PNA or LNA;

(4) a hairpin primer, wherein the hybridizing oligo is modified with additional cross-linked bases, covalently bound or otherwise strongly chemically coupled in place, so that there is greatly reduced chance of the primer not being in place. In various embodiments, halogenated thiopyrimidines and bromodeoxyuridines (e.g., 5'-bromo-2'-deoxyuridine as substitute for thymidine) are photoreactive halogenated bases that can be incorporated into oligonucleotides to crosslink them to DNA, RNA or proteins with exposure to UV light. In various examples, crosslinking is maximally efficient with light at a wavelength of 308 nm. See, e.g., Cleaver, J. E., *Biophys. J.*, 8, 775-91 (1968); Zeng, Y., et al., *Nucleic Acids Res.*, 34(22), 6521-29 (2006); and Brem, H., et al., *J. of Photochemistry and Photobiology B: Biology*, 145, 216-223 (2015).

Since the secondary structure in a DNA template can interfere with the processive action of a polymerase, it may be advantageous to reduce, avoid or eliminate secondary structure in the DNA data encoding template molecules used in DNA data reader sensors. Many methods to reduce secondary structure interference are known to those skilled in the field of molecular biology. Methods to reduce, avoid or eliminate secondary structure include, but are not limited to: using polymerases that possess strong secondary structure displacing capabilities, such as Phi29 or Bst or T7, either native or mutant forms of these; adding to the buffer solvents such as betaine, DMSO, ethylene glycol or 1,2-propanediol; decreasing the salt concentration of the buffer; increasing the temperature of the solution; and adding single strand binding protein or degenerate binding oligos to hybridize along the single strand. Methods such as these can have the beneficial effect of reducing secondary structure interference with the polymerase processing the encoding DNA and producing proper signals.

Additional methods available to reduce unwanted secondary structure for DNA data reading in accordance to the present disclosure comprise adding properties to DNA molecules produced by synthetic chemistry. For example, in some embodiments of the present disclosure, the data encoding the DNA molecule itself can be synthesized from base analogues that reduce secondary structure, such as using deaza-G (7-deaza-2'-deoxyguanosine) in place of G, which weakens G:C base pairing, or by using a locked nucleic acid (LNA) in the strand, which stiffens the backbone to reduce secondary structure. A variety of such analogues with such effects are known to those skilled in the field of nucleic acid chemistry.

Further methods are available in the present disclosure to reduce unwanted secondary structure for the DNA data reading sensor, because the DNA data encoding scheme determines the template sequence, and thus there is potential to choose the encoding scheme to avoid sequences prone to secondary structure. Such Secondary Structure Avoiding ("SSA") encoding schemes are therefore a beneficial aspect of the present disclosure. In general, for encoding schemes as described herein, which use distinguishable signal sequence features as the encoding elements, to the extent there are options in the choice of encoding rules (such as exemplified in FIG. 29), all such alternative schemes could be considered, and the schemes that produce less (or the least) secondary structure would be favored for use. The alternative schemes are assessed relative to a specific digital data payload, or statistically across a representative population of such data payloads to be encoded.

For example, the importance of SSA encoding is illustrated in the embodiment where the sensor provides three distinguishable signal sequence features: AAAAA, TTTTT, and CCCCC. If all three features are used in encoding in the same strand (or on other strands), there is a strong potential for the AAAAA and TTTTT encoding elements, being complementary, to hybridize and lead to secondary structure, either within the strand or between DNA strands. Thus, if the data were instead encoded entirely by the scheme wherein 0→AAAAA and 1→CCCCC, i.e., ignoring the use of TTTTT completely, all such potential secondary structure is avoided. Thus, this encoding (or the other SSA choice, 0→TTTTT and 1→CCCCC) is preferred over a scheme that uses self-complementary sequences, even though information density is reduced by giving up one of the three available encoding elements. Thus, in general, SSA codes can be used when there are encoding options and when there is a potential for DNA secondary structure to form. As shown in this embodiment, desirable SSA codes to reduce DNA secondary structure may be less information dense than what is theoretically possible for the distinguishable signal states. However, this tradeoff can result in a net gain of information density, or related overall cost or speed improvements, by avoiding data loss related to DNA secondary structure.

In various embodiments, methods for reducing secondary structure comprises the use of binding oligos to protect the single strand, wherein the oligos are chosen with sequence or sequence composition that will preferentially bind to the encoding features. Such binding oligos may more effectively protect the single strand and general degenerate oligos. For example, in the case described above with three distinguishable signal sequence features AAAAA, TTTTT, and CCCCC, all three could be used as encoding features, and they could be protected in single stranded form by binding the template to the oligos TTTTT, AAAAA, and GGGGG, or to enhanced binding analogues of these, such as RNA, LNA or PNA forms, instead of DNA. Thus, use of binding oligos that preferentially bind to the encoding features is another means to mitigate unwanted secondary structure effects, although such binding oligos must be used with strand-displacing polymerases, such as native or mutant forms of Klenow, Bst or Phi29, such that the oligos themselves do not interfere. A further method for avoiding secondary structure is to prepare the information encoding DNA in primarily double stranded form, with a nick or gap at the primer site for polymerase initiation, and the rest of the molecule in duplex form, such as is illustrated by the second strand in FIG. 27B (with or without a hairpin bend) so that the DNA molecule exists in solution in a substantially duplex form, free of secondary structure due to single-strand interactions, within or between molecules.

In various embodiments, DNA molecules used to encode information for reading by the cognate molecular sensor can be prepared with an architecture that facilities the reading process as well as the encoding and decoding processes. Various embodiments of DNA architecture are illustrated in FIG. 28. Illustrated is a representative physical form of a primed single-stranded DNA template (at the top of the drawing), along with the logical forms of an information encoding molecule for use in a digital data storage system. Exemplary forms may include Left and Right Adapters (shown as "L ADAPTOR" and "R ADAPTOR"), to facilitate manipulation of the information coding DNA molecules, a primer (e.g., pre-primed or self-priming, shown as "PRIMER"), left and right buffer segments (shown as "L-BUFFER" and "R-BUFFER") and a data payload segment ("DATA PAYLOAD").

With continued reference to FIG. 28, the adapters may comprise, for example, primers for universal amplification processes, used to copy the stored data, or may comprise hybridization capture sites or other selective binding targets, for targeted selection of molecules from a pool. In various embodiments, a primer segment contains primer target/structure, the L-BUFFER segment may contain a signal calibration sequence for the reader, or a buffering sequence prior to the DATA PAYLOAD segment, which contains information storing encoded sequence and related error correction sequence such as parity bits. In various aspects, the R-BUFFER may contain an additional calibration sequence, as well as a buffer sequence preventing the polymerase enzyme getting too close to the end of the template when reading data. In various embodiments, the L-ADAPTER and R-ADAPTER may be sequence elements related to the storage or manipulation of the associated DNA segment, such as adapters for outer priming cites for PCR amplification, or hybridization based selection, or representing a surrounding carrier DNA for this insert, including insertion into a host organism genome as a carrier. In various embodiments, the adapters may comprise surrounding or carrier DNA, for example in the case of DNA data molecules stored in live host genomes, such as in bacterial plasmids or other genome components of living organisms.

With further reference to FIG. 28, the L-BUFFER and R-BUFFER segments may comprise DNA segments that support the polymerase binding footprint, or various calibration or initiation sequences used to help interpret the signals coming from the data payload region. These buffer segments may contain molecular barcode sequences that are used to distinguish unique molecules, or to identify replicate molecules that are derived from the same originating single molecule. One such method of barcoding, known to those skilled in DNA oligo synthesis, comprises the addition of a short random N-mer sequence, typically 1 to 20 bases long, made for example by carrying out synthesis steps with degenerate mixtures of bases instead of specific bases.

With continued reference to FIG. 28, DNA logical structures comprise a data payload segment wherein specific data is encoded. In various embodiments, a data payload segment comprises the actual primary digital data being stored along with metadata for the storage method, which may comprise data related to proper assembly of such information fragments into longer strings, and/or data related to error detection and correction, such as parity bits, check sums, or other such information overhead.

In various embodiments, a data payload DNA structure results from a sensor-specific information encoding scheme applied to a source digital data payload, such as binary data, as illustrated in FIG. 29. In this scenario, the originating digital data that is to be stored as DNA will typically have a prior representation as electronic binary data (1/0 bits). In various embodiments of encoding, this originating data will be: (i) divided into segments, (ii) augmented by re-assembly data, and (iii) transformed by error correcting encodings appropriate for DNA data storage to produce the actual binary data payload segments, such as illustrated in the examples of FIG. 29. These actual binary data payload segments then require translation into DNA payload sequences usable in the subsequent synthesis of the DNA physical storage molecules. In various embodiments, the primary translation is performed by Binary Encoding Schemes ("BES"), such as, for example, shown in FIG. 29. These encoding schemes provide primary translation from a digital data format, such as binary, to a DNA molecular sequence format.

Which BES is appropriate is directly related to the distinguishable signal feature sets of the sensor, as exemplified in FIG. 11. FIG. 29 illustrates several such primary encodings, using an exemplary binary data payload, namely the 32-bit word shown at the top of the drawing figure. Exemplary binary encoding schemes (BES) shown are:

BES1: a standard encoding of four 2 bits into four standard DNA letters (one DNA letter per two binary bits), for use with a reader sensor that can distinguish these features, (e.g., FIG. 22);

BES2: the encoding of two binary digits into two bases (one DNA letter per one binary bit), for use with a reader sensor that can distinguish these, (such as distinguishing between T and G in FIG. 23);

BES3: encoding two binary digits into two runs of bases, AA and CCC, (one run of DNA letters per one binary bit), to encode two binary states for use with a reader sensor that can distinguish these features, (such as distinguishing between AA and CCC in FIG. 24);

BES4: using DNA molecules composed of two modified bases, X, Y, (one modified base per one binary bit), to encode the two binary states, for use with a reader sensor that can distinguish these modified bases in the template, (such as distinguishing X and Y in FIG. 26C);

BES5: using DNA molecules composed of 4 native bases and 4 modified bases, to encode the eight possible 1/0 3-bit states, (one DNA base or modified base per 3-bits of data), for use with a sensor that can distinguish between all eight base features, (such as distinguishing between A, C, G, T, X, Y, Z, and W in FIG. 26D); and BES6 using two DNA sequence motifs, to encode two binary states, (one DNA sequence motif per one binary bit), for use with a reader sensor that can distinguish the signals of these motifs, (such as distinguishing between GATT and ACA in FIG. 26A).

As seen in the examples of FIG. 29, the encoding of the binary data payload for the multi-bit encoding schemes BES1 and BES5 shorten the length of the encoding string in passing from binary to DNA sequence, while the multi-base encoding schemes BES3 and BES6 lengthen the length of the encoding string upon encoding. Code schemes that produce shorter sequences are preferred when reducing the length of synthesized DNA information encoding molecules is a high priority, e.g., for example, when there are practical limitations on oligo length for the writing technology. Further as seen in the examples of FIG. 29, BES2 and BES4 schemes retain the length of the encoding string in passing from binary to DNA sequence. With further reference to FIG. 29, the lower portion of the Figure sets forth the DNA sequences obtained when converting the exemplary binary data payload word (at the top of the drawing figure) with the encoding schemes BES1, BES2, BES3 and BES5.

Binary encoding schemes for use herein are not limited to the examples set forth in FIG. 29, and many variations or similar encoding schemes to those shown in FIG. 29 are also implicit in these examples, such as by permuting the letters used, or changing the lengths of sequencing motifs, the composition of sequence motifs, and/or the choice of modified or analog bases. It is also understood that all such encoding schemes have a cognate sensor that is capable of distinguishing the signals of the encoding features, so that the choices of BES are directly related to the properties of the sensor in distinguishing features. It is also understood that, even though the examples of FIG. 29 exemplify cases with 2, 4 or 8 distinguishable features, for convenience in describing bit encodings of 1, 2 or 4 bits, encodings of binary data can be done based on any number of distinguishable signal features, such as 3 distinguishable features as in the sensor of FIG. 26B.

In various embodiments, information as binary data such as 010011100010 may be encoded using three states A, B, C, wherein 0 is encoded as A, 1 is encoded as B, and 00 is encoded as C whenever 00 occurs, (i.e., to not encode 00 as AA). In accordance to this scheme, the binary word 010011100010 is equivalent to the encoded form ABCBBB-CABA. Similarly, digital data formats or alphabets other than binary, such as hexadecimal, decimal, ASCII, etc., can be equally encoded by similar schemes as those exemplified in FIG. 29. Such methods are well known to those skilled in the field of computer science. Schemes more sophisticated than those shown, in terms of optimal information density, such as Lempel-Ziv encoding, can highly efficiently convert and compress data from one alphabet into another.

In general, for converting a binary or other digital data payload string or collection of strings into a DNA sequence string or collection of such strings, many of the methods of lossless and lossy encoding or compression, e.g., those well known in computer science, can be used to devise schemes for the primary conversion of input digital data payloads to DNA sequence data payloads, as strings of distinguishable feature DNA segments, generalizing the examples of FIG. 29. In this broader context, the BES schemes exemplified in FIG. 29 illustrate the type of feature elements that could become symbols of an alphabet for data encoding, such as standard bases, modified bases, or sequence motifs or runs, and that such elements must have a cognate reader sensor.

In an illustrative embodiment, a sensor distinguishes between the sensor motifs CCC, AA, and G, represented herein as "a," "b," and "c," respectively, wherein a binary data string is encoded into these symbols in accordance with a lossless or lossy data encoding or compression scheme as string "aabcacb." In this embodiment, the string aabcacb would be directly translated into DNA sequences CCC, CCC, AA, G, CCC, G, and AA. These segments can then be directly converted into a DNA data payload sequence, in this case CCCCCCAAGCCCGAA (SEQ ID NO: 2).

In certain variations, there may be "punctuation" sequences inserted between distinguishable signal features, which do not alter the distinguishable features but that may provide benefits such as accommodating special properties or constraints of the DNA synthesis chemistry, or to provide spacers for added time separation between signal features, or to improve the secondary structure of the DNA molecule. For example, if T were such a punctuation sequence, the DNA encoding sequence in the above example would become TCCCTCCCTAATGTCCCTGTAAT (SEQ ID NO: 3), (i.e., a punctuating "T" inserted between each of the sequence segments CCC, CCC, AA, G, CCC, G, and AA). In general, such insertion of punctuation sequences or filler sequences may be part of the process of translating from a digital data payload to the DNA encoding sequence to be synthesized.

In various aspects of the present disclosure, a DNA data payload of interest is processed by a polymerase sensor multiple times to provide a more robust recovery of digital data from DNA storage. In other aspects, a collection of such payloads on average are processed some expected number of multiple times. These examples benefit from a more accurate estimation of the encoding distinguishable features by aggregating the multiple observations. Multiple processing also has the benefit of overcoming fundamental Poisson sampling statistical variability to ensure that, with high confidence, a data payload of interest is sampled and observed at least once, or at least some desirable minimal number of times.

In various embodiments, the number of such repeat interrogations is in the range of 1 to about 1000 times, or in the range of about 10 to 100 times. Such multiple observations may comprise: (i) observations of the same physical DNA molecule by the polymerase sensor, and/or (ii) one or more polymerase sensors processing multiple, physically distinct DNA molecules that carry the same data payload. In the latter case, such multiple, physically distinct DNA molecules with the same data payload may be the DNA molecules produced by the same bulk synthesis reaction, the molecules obtained from distinct synthesis reactions targeting the same data payload, or replicate molecules produced by applying amplification or replication methods such as PCR, T7 amplification, rolling circle amplification, or other forms of replication known to those skilled in molecular biology. The aggregation of such multiple observations may be done through many methods, such as averaging or voting, maximum likelihood estimation, Bayesian estimation, hidden Markov methods, graph theoretic or optimization methods, or deep learning neural network methods.

In various aspects of the present disclosure, molecular biology methods enable the polymerase sensor to interrogate the same DNA molecule data payload multiple times. Three such embodiments of template architectures are shown in FIG. 27B. One such method is to circularize the molecule (upper figure), such as via ligation of the ends, and use a strand displacing polymerase that can repeat the process around the circle multiple times, thereby generating multiple reads of the same molecule. Another method is to have a hairpin duplex (middle figure), and use a strand displacing polymerase that processes the lower strand, wraps around the hairpin feature, and processes the upper strand of the molecule that comprises a complementary sequence, which, in some embodiments, may also provide distinguishable signals related to the lower strand distinguishable signals. One other embodiment, illustrated in the lower figure of FIG. 27B, is to construct the template molecule with a tandem repeat of the data payload, repeated one or more times, so that the processive enzyme will process through multiple instances of the same data payload.

In various embodiments of the present disclosure, digital data stored in DNA is read at a high rate, such as approaching 1 Gigabyte per second for the recovery of digital data, as is possible with large scale magnetic tape storage systems. Because the maximum processing speed of a polymerase enzyme is in the range of 100-1000 bases per second, depending on the type, the bit recovery rate of a polymerase-based sensor is limited to a comparable speed. Thus, in various embodiments millions of sensors are deployed in a cost effective format to achieve the desired data reading capacity.

In various embodiments, many individual molecular sensors are deployed herein in a large scale sensor array on a CMOS chip, which is the most cost-effective, semiconductor chip manufacturing process. FIG. 30A illustrates an embodiment of a fabrication stack usable to create a massively parallel array of molecular sensors on a chip. In this example, the sensor measurement circuitry is deployed as a scalable pixel array as a CMOS chip, a nano-scale lithography process is used to fabricate the nano-electrodes, and molecular self-assembly chemical reactions, in solution, are used to establish the molecular complex on each nano-electrode in the sensor array. The result of this fabrication stack is the finished DNA reader sensor array chip indicated at the bottom of FIG. 30A. In various embodiments, the nanoscale lithography is done using a high resolution CMOS node, such as a 28 nm, 22 nm, 20 nm, 16 nm, 14 nm, 10 nm, 7 nm or 5 nm nodes, to leverage the economics of CMOS chip manufacturing. In contrast, the pixel electronics may be done at a coarser node better suited to mixed signal devices, such as 180 nm, 130 nm, 90 nm, 65 nm, 40 nm, 32 nm or 28 nm. Alternatively, the nano-electrodes may be fabricated by any one of a variety of other fabrication methods known to those skilled in the art of nanofabrication, such as e-beam lithography, nano-imprint lithography, ion beam lithography, or advanced methods of photolithography, such as any combinations of Extreme UV or Deep UV lithography, multiple patterning, or phase shifting masks.

FIG. 30B illustrates an embodiment of a high-level CMOS chip pixel array architecture for a DNA sequencing chip (at the left side of the figure), comprising a scalable array of sensor pixels, with associated power and control circuitry and major blocks such as Bias, Analog-to-Digital convertors, and timing. The inset in the figure shows an individual sensor pixel as a small bridged structure and where this individual electronic sensor is located in the array of sensor pixels. FIG. 30B also illustrates (at the right side of the figure) the details of an embodiment of a molecular electronics sensor circuit pixel in the array. As illustrated in FIG. 30B, the sensor pixel comprises an amplifier, a reset switch, and circuitry for supplying the source, gate and drain voltages, and readout of results. In various embodiments, the single pixel circuitry comprises a trans-impedance current amplifier, a voltage-biasable source, reset switches. FIG. 31 shows an embodiment of a circuit schematic of the pixel amplifier in detail at the left side of the figure, along with simulation results at the right side of the figure showing the voltage signal vs time when used to measure a 10 pA current, and with a reset applied periodically as indicated in the plot. This embodiment exemplifies one non-limiting selection of circuit components and parameters (transistor, resistors, capacitors, etc.).

FIG. 32 illustrates an embodiment of an annotated chip design layout file and the corresponding finished chip for comparison. At the left of FIG. 32 is an annotated image of the rendered layout (GDS) file for the chip design comprising the CMOS pixel array of FIG. 30B with 256 pixels, and annotated to show the location of the Bias, Array and Decoder regions of the chip. At the right of FIG. 32 is an optical microscope image of the corresponding finished chip based on the final design, produced at TSMC, Inc. semiconductor foundry (San Jose, Calif.) with the TSMC 180 nm CMOS process, with no passivation layer.

FIG. 33 shows SEM images of the finished CMOS chip of FIG. 32, with high-resolution images further showing an 80 μm pixel for a reader system comprising nanoelectrodes and a polymerase molecular complex in place between the electrodes. At the left of FIG. 33 is a SEM image of the CMOS chip, with no top passivation layer and exposed planarized metal 6 layer. The middle higher resolution image clearly showing the sub-optical surface features of an 80 μm pixel, and notably the exposed vias (source, gate, and drain) where the nanoelectrodes are to be deposited by post-CMOS nanofabrication processing steps and electrically connected into the amplifier circuit, as shown in the right portion of FIG. 30B. The furthest right SEM image in FIG. 33 shows an e-beam lithography fabricated pair of spaced apart nanoelectrodes with a molecular complex in place. The sketch at the bottom right of FIG. 33 is an illustration of the molecular electronics sensor comprising a polymerase molecular complex, which is labeled by the gold dot.

In various embodiments of a DNA reader device, use of a CMOS chip device in conjunction with nano-scale manufacturing technologies, ultimately yield a much low cost, high throughput, fast, and scalable system. For example, sensors such as this can process DNA templates at the rate of 10 or more bases per second, 100 or more times faster than current optical sequencers. The use of CMOS chip technology ensures scalability and low system cost in a mass-producible format that leverages the enormous infrastructure of the semiconductor industry. As noted, whatever error modes or accuracy limitations may exist in a DNA sensor, or that may arise at faster reading speed (e.g. by modifying the enzyme or buffer or temperature or environmental factors, or sample data at lower time resolution) can be compensated for in the overall encoder/decoder-reader-writer framework described.

In various embodiments of the present disclosure, a DNA reader chip for use herein comprises at least 1 million sensors, at least 10 million sensors, at least 100 million sensors, or at least 1 billion sensors. Recognizing that at a typical sensor data sampling rate of 10 kHz, and recording 1 byte per measurement, a 100 million sensor chip produces raw signal data at a rate of 1 Terabyte (TB) per second. In considering how many sensors are desirable on a single chip, one critical consideration is the rate at which such a chip can decode digital data stored in DNA compared to the desirable digital data reading rates. It is, for example, desirable to have digital data read out at a rate of up to about 1 Gigabyte per second. Note that each bit of digital data encoded as DNA will require multiple signal measurements to recover, given that a feature of the signal use used to store this information, so this raw signal data production rate for the measured signal will be much higher that the recovery rate of encoded digital data. For example, if 10 signal measurements are required to recover 1 bit of stored digital data, as might be the case for signal features such as in FIG. 11, and each measurement is an 8-bit byte, that is a factor of 80 bits of signal data to recover 1 bit of stored digital data. Thus, digital data reading rates are anticipated to be on the order of 100 times slower than the sensor raw signal data acquisition rate. For this reason, achieving desirable digital data reading rate of 1 Gigabyte/sec would require nearly 0.1 TB/sec of usable raw signal data. Further, given that not all the sensors in a single chip may be producing usable data, the need for chips that produce up to 1 TB/sec of raw data is desirable, based on the desired ultimate digital data recover rates from data stored as DNA. In various embodiments, such recovery rates correspond to a 100 million sensor pixel chip.

In various embodiments of the present disclosure, multiple chips are deployed within a reader system to achieve desired system-level digital data reading rates. The DNA data reader chip of FIG. 30A is, in various embodiments, deployed as part of a complete system for reading digital data stored in DNA. The features of an embodiment of a complete system are illustrated in FIG. 34. In various aspects, and with reference to FIG. 34, a complete digital data reading system comprises a motherboard with a staging area for an array of multiple chips, in order to provide data reading throughput beyond that of the limitations of a single chip. Such chips are individually housed in flow cells, with a fluidics liquid handling system that controls the addition and removal of the sensor system liquid reagents. In addition, the fluidics system receives DNA encoding data in solution form, originating from a data repository source. In various aspects, the motherboard further comprises a suitable first stage data processing unit capable of receiving and reducing raw signal data at very high rates, e.g., exceeding 1 TB/sec, exceeding 10 TB/sec, or exceeding 100 TB/sec, indicated as a primary signal processor. This primary processor may comprise one, multiple, or combinations of a FPGA, GPU, or DSP device, or a custom signal processing chip, and this may optionally be followed by stages of similar such signal processors for a processing pipeline. Data output of this primary pipeline is typically transferred to a fast data storage buffer, such as a solid state drive, with data from here undergoing further processing or decoding in a CPU-based sub-system, from which data is buffered into a lower speed mass storage buffer, such as a hard drive or solid state drive or array of such drives. From there it is transferred to an auxiliary data transfer computer sub-system that handles the subsequent transfer of decoded data to a destination. All these system operations are under the high-level control of an auxiliary control computer that monitors, coordinates and controls the interplay of these functional units and processes.

In various embodiments, chips within the reader system may be disposable and replaced after a certain duty cycle, such as 24 hours to 48 hours. In other embodiments, the chips may be reconditioned in place after such a usage period, whereby the molecular complex, and possibly conjugating groups, are removed, and then replaced with new such components through a serious of chemical solution exposures. The removal process may comprise using voltages applied to the electrodes to drive removal, such as an elevated voltages applied to the electrodes, an alternating voltage applied to the electrodes, or a voltage sweep. The process may also comprise the use of chemicals that denature, dissolve or dissociate or otherwise eliminate such groups, such as high molarity urea, or guanidine or other chaotropic agents, proteases such as Proteinase K, acids such as HCl, bases such as KOH or NaOH, or other agents well known in molecular biology and biochemistry for such proposes. This process may also include the use of applied temperature or light to drive the removal, such as elevated temperature or light in conjunction with photo-cleavable groups in the molecular complex or conjugation groups.

FIG. 35 illustrates an embodiment of a cloud based DNA data archival storage system, in which the complete reader system, such as exemplified in FIG. 34, is, in certain embodiments, deployed in aggregate format to provide the cloud DNA reader server of the overall archival storage and retrieval system. The system of FIG. 35 comprises a cloud computer system, with a standard storage format (depicted at the upper left of the figure). Such as standard cloud computer system comprises a DNA archival data storage capability as indicated. In various aspects, a cloud-based DNA synthesis system can accept binary data from the cloud computer and produce the physical data encoding DNA molecules. This server stores the output molecules in a DNA data storage archive (depicted at the lower right of the figure) wherein the physical DNA molecules that encode data are stored in a dried or lyophilized form, or in solution, at ambient temperature, cooled temperature, or frozen. When data is to be retrieved, a sample of the DNA from the archive is provided to the DNA data reader server, which outputs decoded binary data back to the primary cloud computer system. This DNA data reader server is, in certain embodiments, powered by a multiplicity of DNA reader chip-based systems, such as indicated in FIG. 34, in combination with additional computers that perform the final decoding of the DNA derived data back to the original data format of the primary cloud storage system.

In various embodiments, a molecular electronics sensor comprises the configuration illustrated in FIG. 36. In this case, fundamental electronic measurements are made by a nanopore ionic current sensor that consists of electrodes on either side of a membrane, a pore localized in the membrane, and an aqueous solution phase residing on both sides of the pore. In this embodiment, the pore regulates the passage of ionic current (indicated by the dashed arrow and the "i"). The pore may comprise a biological protein nanopore, native or mutated, and the membrane may comprise a lipid membrane, or synthetic analogue thereof. The pore may also comprise a solid state pore, with the membrane comprising a thinned membrane composed of a solid material such as SiN, or Teflon. The pore may have electrodes of the same polarity, or, as illustrated, opposite polarity. As shown in FIG. 36, the polymerase molecule is further complexed with the pore, as part of a molecular complex involving a small number of molecules embedded through the membrane as part of the pore and to provide a conjugation to the polymerase. As the polymerase processes a DNA template, the ionic current through the pore is modulated by this activity, producing distinguishable signal features that correspond to distinct sequence features. Aside from a different geometry of the nano-electrical measurement, the considerations are otherwise identical to those already reviewed herein. That is, nano-pore current sensor versions of the polymerase-based DNS digital data reader are of similar use herein.

In various embodiments, a molecular electronics sensor comprises the configuration shown in FIG. 37, wherein the polymerase is directly and specifically conjugated to the pore, and wherein modified dNTPs are used to produce distinguishable signals from DNA sequence features, which is a situation comparable to that of FIG. 23 for the nanoelectrode sensor. For producing signals in a nanopore sensor, such dNTP modifications may comprise groups on the γ-phosphate of the dNTP, which can occlude the pore while the dNTP is undergoing incorporation by the polymerase, thereby resulting in current suppression features. In various embodiments, such modifications comprise extending the tri-phosphate chain to 4, 5, 6 or up to 12 phosphates, and adding terminal phosphate groups, or groups to any of phosphates at position 2 or more, which are removed by polymerase incorporation, such groups including polymers that may occlude the pore by entering pore, such as comprising PEG polymers or DNA polymers. The polymerase conjugation to the pore may comprise any one of possible conjugation chemistries, such as a molecular tether, or Spy-SpyCatcher protein-based conjugation system, or the like. For the nanopore sensor embodiments indicated in FIG. 36 and FIG. 37, all the aspects of the disclosure put forth above in the context of FIG. 10B also apply in this instance, to provide a nanopore ion current sensor-based sensor for reading digital data stored in DNA molecules, and the related beneficial aspects, encoding schemes, chip formats, systems and cloud based DNA digital data storage systems.

One embodiment of the molecular electronic sensor of FIG. 10B, illustrated conceptually in FIG. 15, comprises a carbon nanotube as the bridge molecule (represented by the bold horizontal bar in FIG. 15 bridging the gap between positive and negative electrodes). This embodiment is illustrated in FIG. 38. In various aspects, the carbon nanotube bridge comprises a single or multi-walled carbon nanotube, and is conjugated to the polymerase molecule at a specific site using any of many possible conjugation chemistries. Such a conjugation may, for example, comprise a pyrene linker to attach to the nanotube via n-stacking of the pyrene on the nanotube, or may comprise attachment to a defect site residing in the carbon nanotube. In this case, the current passing through a carbon nanotube molecular wire is known to be a highly sensitive other molecules in the surrounding environment, such as indicated in FIG. 10A. It is further known that current passing through a carbon nanotube is sensitive to the activity of an enzyme molecule properly conjugated to that nanotube, including polymerase enzymes. For this particular embodiment, all the aspects of the present disclosure put forth above apply in this instance, to provide a carbon nanotube based sensor for reading digital data stored in DNA molecules, including the related beneficial aspects, encoding schemes, chip formats, systems and cloud based DNA digital data storage systems.

An alternative sensor that produces optical signals is a Zero Mode Waveguide sensor, such as the sensor illustrated in FIG. 39. Such a sensor may comprise a single polymerase as shown, conjugated to the bottom of the metallic well, in the evanescent zone of the excitation field applied to the thin substrate, in a Total Internal Reflection mode. The polymerase is provided with primed template and dNTPs with dye labels on the cleavable phosphate group. When such a dNTP is incorporated, the dye label is held in the evanescent field, and is stimulated to emit photons of the corresponding dye energy spectrum or color. The result is that, under appropriate conditions, such a sensor may produce distinguishable optical signals as indicated, which can be used to encode digital information into DNA molecules. The distinguishable signals here may be photon emissions of a different energy distribution, or color, or emissions with different distinguishable spectra, or different duration or intensity or shape of the spectra versus time, or any combination of such elements that result in distinguishable features. For this Zero Mode Waveguide sensor embodiment indicated in FIG. 39, all the aspects of the disclosure put forth above in the context of FIG. 10B also apply in this instance, to provide a Zero Mode Waveguide-based sensor for reading digital data stored in DNA molecules, and the related beneficial aspects, encoding schemes, chip formats (in this case, optical sensor chips, such as image sensor chips), systems and cloud based DNA digital data storage systems may apply to such a sensor.

Optimization of the DNA Writing Device

In various embodiments, the DNA information storage system of the present disclosure further comprises a DNA writing device capable of writing a large number of DNA sequences in parallel as synthesized molecules, with each desired sequence embodied in multiple synthesized molecules, and the rate of synthesis, or time per base, as fast as possible such that the overall rate of writing DNA information is fast enough, and at high enough volume, for practical use in large scale archival information storage.

Current commercial DNA synthesis based on the classical phosphoramidite chemistry cycle is relatively slow, requiring on the order of 30 minutes per base addition. The bulk of the 30 minute base addition cycle is the acid-mediated deprotection of the 5'-OH on the distal end of the extending oligonucleotide chain. The prolonged exposure of the incipient sequences to these acid conditions also creates a major source of sequence error via de-purination. This method also suffers from relatively low parallelism, being performed in 384 well-plates on an expensive instrument. The process is also limited to making sequences of at most several hundred bases in length due to efficiency yield limitations in a stepwise synthesis. Therefore, this method is best suited to make larger quantities of each of a small number (1 to thousands) of relatively short (<~200 base) DNA sequences.

Higher throughput commercial DNA synthesis systems have been developed to support the in-situ synthesis of DNA microarrays. Such systems in effect print a large array of micro-spots of in-situ synthesized DNA, adding one base at a time in a highly parallel way across the spots. For example, the Agilent ink-jet-based DNA oligo array printer can print an array of up to 1 million DNA spots on a glass microscope slide, where each spot is on the order of 20 microns in diameter, with a 30-micron spot-to-spot pitch for the rectangular array of spots. The synthesis reaction is still relatively slow, on the order of 1 base per hour, and the DNA length is even more limited than classical well-plate synthesis, to practical lengths of up to ~100 bases. Nonetheless, systems such as this can synthesize a total of ~100 million letters of DNA sequence (~25 MB), in several days, at a cost of several hundred dollars for the finished array—although the writing instrument has a high capital cost and complexity such that it has never been commercialized, and production of such DNA arrays is done in a centralized factory format with limited capacity. Furthermore, future upscaling of this technology in terms of spots/array may be at the asymptotic limit already, given that it leverages existing ink-jet technology which may itself have reached its asymptotic limit.

Thus, for large scale archival DNA storage, substantially lower costs, faster speed, and lower capital cost of the DNA writing device are highly desirable. In particular, the storage writing cost is still near $10 per MB, which is far above the estimated $0.02 per GB (500,000 fold more) for magnetic tape storage writing. Thus the costs of writing DNA need to come down dramatically to make common long term storage applications practical, preferably by several orders of magnitude, and preferably by 1,000,000 fold.

To achieve this goal, and in certain embodiments of the present disclosure, a DNA writing system for use herein comprises a CMOS-chip based array of actuators for DNA synthesis. The DNA writer consists of a CMOS chip, with an array of actuator pixels that direct actuator specific voltage/current or light mediated 5'-OH deprotection, whereby novel voltage or light sensitive protecting groups enable faster deprotection kinetics and no de-purination errors. In various aspects, the chip includes millions up to billions of actuator pixels. Such pixels may comprise a nanoelectrode and/or selectable light source, around which DNA synthesis takes place. Voltage applied to this electrode, or current sourced to it, or localized light actuation would control each 5'-OH deprotection reaction, as a series of A, C, G, T, . . . cyclical addition reactions take place globally across the chip, and wherein each pixel controls the addition or not of the supplied base during each cycle via voltage or current or light.

The use of CMOS chip scaling supports the ability to ultimately provide billions of such synthesis sites on a standard, low cost, mass-produced chip. Localized voltage/light actuation can also be used to accelerate the synthesis chemistry and shorten the cycle time, such as from ~30 minutes down to seconds. The actuator electrodes may be derivatized with chemical layers that transduce voltage or current to other useful electrochemical local environment changes, such as, for example, to provide for voltage-generated acids as the means to modulate non-classical phosphoramidite synthesis chemistry. In other aspects, a voltage/current may modulate a conformational or steric or mechanical change of local polymer/molecular matrix structure in which the synthesis takes place, that physically impedes or allows the base addition. In particular, one embodiment of such a system could have micro- or nano-wells or containers at each site, which contain the growing DNA oligos and which can be actuated to open/close to physically selectively control the base addition reactions. The added bases may also contain charge or other modifications that facilitates the use of voltage or light to direct and control the process. Through CMOS chip scaling and voltage or current or light-directed synthesis augmentation of a phosphoramidite synthesis cycle, there is the potential for large increases in scale, and reductions in cost of the process and instrument used to perform synthesis. The finished DNA fragments, consisting of multiple exemplars of each target sequence for a given pixel as each site, can be released from the support post-synthesis, and pooled in solution to form the physical archive.

In the context of this and other DNA writer embodiments, selection of the encoding/decoding algorithm may minimize system costs, especially time costs. For example, dephosphorylating is a slow process, and some of the bases and sequences (e.g., purine versus amine, homogenous runs of G and C) are more difficult to synthesis due to chemical or secondary structure effect. This presents the option to not drive the dephosphorylating to completion, to save time, at the cost of more error, and also avoid the use of certain base compositions in the encoded sequence (e.g. do not use purines, or do not use runs of G, etc., in the encoding) to allow faster chemical processing without major added error burden. In this way the synthesis reaction can be accelerated, and the encoding/decoding algorithm can compensate in terms of the error corrective or error avoiding encoding.

Aside from avoiding high error sequence modes, standard error correcting code algorithms can correct extremely high rates of error in the DNA sequence, even extreme error rates of up to 50% or more. In various aspects, the encoding/decoding is co-optimized with the properties of the DNA reader and DNA writer, so as to optimize overall system performance, and/or to reduce overall system cost by some cost measure of interest such as time of financial cost.

Optimization of the DNA Storage Archive Operations

In certain aspects, the DNA information storage system further comprises a DNA storage archive. In various embodiments of the DNA information storage system, novel ways are provided to achieve desirable operations related to managing storage archives. In various embodiments of the present system, the following types of operations may be performed:

Create a copy of the archive;
Append data to the archive;
Readout a targeted volume from the archive;
Delete a volume from the archive; or
Search the Archive.

In various embodiments, a DNA archive comprises a pool of DNA molecules, with each desired DNA sequence represented by a number of molecular exemplars. This pool of DNA molecules may be stored in a dry state, or in solution phase such as maintained at low temperature or frozen in storage. In certain examples, the archive can temporarily be brought up to working temperatures in a compatible buffer solution to perform these operations. These operations would be performed efficiently by the physical storage system, which may include freezers, refrigerators, and automation for handling of tubes, liquid handling, performing reactions, and the other procedures related to maintaining and manipulating the physical archive material.

In various embodiments, storage-related operations in a DNA storage archive can be achieved as follows:

Copying:

Copying an archive may comprise taking an aliquot of a stock solution, or, for copy without depletion, by including in the molecular encoding amplification primer sites, and priming and amplifying, in linear or exponential amplification reactions, the archive prior to taking an aliquot as a copy.

Appending:

Appending data to the archive or merging archives can be achieved by pooling in and mixing with the additional DNA or archive material.

Targeted Reading/Deleting:

Working with individual "volumes" within an archive can be performed by encoding into the DNA molecules sequence-specific oligo binding sites, with a different identifier/binding sequence for each volume to be made so accessible. Then, to readout a specific volume, hybridization-based capture could be used to select out just DNA fragments with desired binding sequences. Deleting of a volume could be performed by a subtractive-hybridization processes to remove all DNA fragments with a given binding sequence. In another embodiment, the deletion could be performed by using oligo-directed DNA cleavage/degradation, in particular enzymatic methods that use Cleavase, DICER or CRISPER for oligo-binding directed destruction of the targeted molecules. In yet another embodiment, primer binding followed by a synthesis or ligation reaction may be used to incorporate bases or oligos that allow selective destruction or removal, such as through biotinylated elements removed by a streptavidin column. Volume identifiers could also be added by synthesizing DNA with nucleotide modifications, so the relevant binding targets are not via DNA-sequence specific hybridization per se, but in other modifications on the bases used in the synthesis. For example, use of biotinylated bases, or bases with various hapten modifications, etc., similarly provide selective ability to bind or manipulate subsets of the DNA via the corresponding interaction partners for these modifications intentionally introduced in the synthesis.

Searching:

Search of an archive for a literal input string can be achieved by encoding the search string or strings of interest into DNA form, synthesizing a complementary form or related primers for the desired DNA sequences, and using hybridization or PCR amplification to assay the archive for the presence of these desired sequence fragments, according to such standard assays are used by those skilled in the art of molecular biology to ascertain the presence of a sequence segment in a complex pool of DNA fragments. The search could report either presence or absence, or could recover the associated fragments containing the search string for complete reading.

We claim:

1. An information storage system comprising:
   a writing device that synthesizes a nucleotide sequence that encodes a set of information; and
   a reading device that interprets the nucleotide sequence by decoding the interpreted nucleotide sequence into the set of information,
   wherein the reading device comprises a molecular electronics sensor, the sensor comprising a pair of spaced apart electrodes and a molecular complex attached to each electrode to form a molecular electronics circuit, wherein the molecular complex comprises a bridge molecule and a probe molecule, and
   wherein the molecular electronics sensor produces distinguishable signals in a measurable electrical parameter of the molecular electronics sensor, when interpreting the nucleotide sequence.

2. The system of claim 1, wherein the set of information is binary.

3. The system of claim 1, wherein the nucleotide sequence comprises a DNA sequence.

4. The system of claim 3, further comprising at least one of error detecting schemes or error correction schemes for minimizing errors within the DNA sequence.

5. The system of claim 4, wherein the error detecting schemes are selected from repetition code, parity bits, checksums, cyclic redundancy checks, cryptographic hash functions and hamming codes, and the error correction schemes are selected from automatic repeat request, convolutional codes, block codes, hybrid automatic repeat request and Reed-Solomon codes.

6. The system of claim 1, wherein the writing device comprises a CMOS chip based array of actuator pixels for DNA synthesis, the actuator pixels directing voltage/current or light-mediated deprotection within a DNA synthesis reaction comprising a phosphoramidite or ligation chemistries.

7. The system of claim 1, wherein the probe molecule comprises a polymerase enzyme, and wherein the measurable electrical parameter of the sensor is modulated by enzymatic activity of the polymerase enzyme.

8. The system of claim 7, wherein the polymerase enzyme comprises a native polymerase enzyme or a genetically engineered polymerase enzyme selected from Klenow, Phi29, TAQ, BST, T7, or a reverse transcriptase.

9. The system of claim 7, wherein the reading device further comprises a buffer solution, operating parameters for measuring the measurable electrical parameter, and two or more sequence segments of a DNA template molecule, that, when processed by the polymerase, produce the distinguishable signals in the measurable electrical parameter when performed in the conditions provided by the buffer solution and the operating parameters.

10. The system of claim 9, wherein the buffer solution comprises modified dNTPs.

11. The system of claim 9, wherein the sequence segments of the DNA template molecule that produce the distinguishable signals comprise any one or combination of different DNA bases, modified DNA bases, DNA base analogues, multi-base sequences or motifs, or homopolymer runs of DNA bases.

12. The system of claim 1, wherein the measurable electrical parameter of the sensor comprises a source-drain current between the spaced apart electrodes and through the molecular complex.

13. The system of claim 1, wherein the molecular electronics sensor is part of a CMOS sensor array chip further comprising a plurality of molecular electronics sensors and supporting pixel circuitry that performs measurement of the measurable electrical parameter.

14. The system of claim 1, wherein the molecular electronics sensor further comprises a gate electrode adjacent the spaced apart electrodes.

15. The system of claim 1, wherein the bridge molecule comprises a double stranded DNA oligomer, a protein alpha helix, a graphene nanoribbon, a carbon nanotube, an antibody, or a Fab arm of an antibody.

16. A method of interpreting a set of information encoded in a nucleotide sequence of a polynucleotide molecule, the method comprising:
- supplying the polynucleotide molecule to a molecular electronics sensor capable of producing distinguishable signals in a measurable electrical parameter of the molecular electronics sensor, relating to the set of information;
- generating the distinguishable signals; and
- converting the distinguishable signals into the set of information,
- wherein the molecular electronics sensor comprises a pair of spaced apart electrodes and a molecular complex attached to each electrode to form a molecular electronics circuit, wherein the molecular complex comprises a bridge molecule and a probe molecule.

17. The method of claim 16, wherein the set of information is binary.

18. The method of claim 16, wherein the nucleotide sequence comprises a DNA sequence.

* * * * *

SEQUENCE LISTING

<160> NUMBER OF SEQ ID NOS: 12

<210> SEQ ID NO 1
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 1

Cys Cys Pro Gly Cys Cys
1               5

<210> SEQ ID NO 2
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 2 cccccaagc ccgaa                                                      15

<210> SEQ ID NO 3
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 3
tccctcccta atgtccctgt aat                                            23

<210> SEQ ID NO 4
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 4
aacccaaaac ccccc                                                     15

<210> SEQ ID NO 5
<211> LENGTH: 53
<212> TYPE: DNA
<213> ORGANISM: Artificial Sequence
<220> FEATURE:
<223> OTHER INFORMATION: Synthetic Sequence

<400> SEQUENCE: 5
aaaaaaaaaa aaaaaaaaaa cccaaaaaaa aaaaaaaaaa aaaaaaaaaa aaa           53

<210> SEQ ID NO 6

```
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 6
gattacagat tacaaca                                                    17

<210> SEQ ID NO 7
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 7
gattacaagg gattaggagg aca                                             23

<210> SEQ ID NO 8
<211> LENGTH: 13
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (3)..(3)
<223> OTHER INFORMATION: n = Z = modified base analog of G
<220> FEATURE:
<221> NAME/KEY: modified_base
<222> LOCATION: (4)..(4)
<223> OTHER INFORMATION: n = X = modified base analog of A
<220> FEATURE:
<221> NAME/KEY: modified_base
<222> LOCATION: (6)..(6)
<223> OTHER INFORMATION: n = Z = modified base analog of G
<220> FEATURE:
<221> NAME/KEY: modified_base
<222> LOCATION: (9)..(9)
<223> OTHER INFORMATION: n = Y = modified base analog of C
<220> FEATURE:
<221> NAME/KEY: modified_base
<222> LOCATION: (11)..(11)
<223> OTHER INFORMATION: n = W = modified base analog of T
<220> FEATURE:
<221> NAME/KEY: modified_base
<222> LOCATION: (13)..(13)
<223> OTHER INFORMATION: n = X = modified base analog of A

<400> SEQUENCE: 8
ganntntanc nan                                                        13

<210> SEQ ID NO 9
<211> LENGTH: 16
<212> TYPE: DNA
<213> ORGANISM: Artificial Sequence
<220> FEATURE:
<223> OTHER INFORMATION: Synthetic Sequence

<400> SEQUENCE: 9
aggcgctatt ggagtc                                                     16

<210> SEQ ID NO 10
<211> LENGTH: 32
<212> TYPE: DNA
<213> ORGANISM: Artificial Sequence
<220> FEATURE:
<223> OTHER INFORMATION: Synthetic Sequence

<400> SEQUENCE: 10
```

```
aacacaacca acccaacccc cacaaacacc ac                              32

<210> SEQ ID NO 11
<211> LENGTH: 81
<212> TYPE: DNA
<213> ORGANISM: Artificial Sequence
<220> FEATURE:
<223> OTHER INFORMATION: Synthetic Sequence

<400> SEQUENCE: 11
aaaacccaac ccaaaacccc ccaaaacccc ccccaaaac cccccccc cccaaccca    60 aaaaacccaa cccccaacc c                                           81

<210> SEQ ID NO 12
<211> LENGTH: 11
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (5)..(5)
<223> OTHER INFORMATION: n = W = modified base analog of T
<220> FEATURE:
<221> NAME/KEY: modified_base
<222> LOCATION: (7)..(7)
<223> OTHER INFORMATION: n = Z = modified base analog of G

<400> SEQUENCE: 12
cgtcntngct t                                                     11
```